United States Patent
Allen et al.

(10) Patent No.: US 6,867,200 B1
(45) Date of Patent: Mar. 15, 2005

(54) (HETERO)ARYL-BICYCLIC HETEROARYL DERIVATIVES, THEIR PREPARATION AND THEIR USE AS PROTEASE INHIBITORS

(75) Inventors: Darin A. Allen, Moutain View, CA (US); Jason M. Hataye, San Francisco, CA (US); Witold N. Hruzewicz, San Francisco, CA (US); Aleksandr Kolesnikov, San Francisco, CA (US); Richard L. Mackman, San Francisco, CA (US); Roopa Rai, San Carlos, CA (US); Spencer R. Jeffrey, So. San Francisco, CA (US); Erik J. Verner, Foster City, CA (US); Wendy B. Young, San Mateo, CA (US); William Dvorak Shrader, Belmont, CA (US)

(73) Assignee: Axys Pharmaceuticals, Inc., So. San Francisco, CA (US)

( * ) Notice: Subject to any disclaimer, the term of this patent is extended or adjusted under 35 U.S.C. 154(b) by 0 days.

(21) Appl. No.: 09/868,276

(22) PCT Filed: Dec. 17, 1999

(86) PCT No.: PCT/US99/30302

§ 371 (c)(1),
(2), (4) Date: Jan. 18, 2002

(87) PCT Pub. No.: WO00/35886

PCT Pub. Date: Jun. 22, 2000

Related U.S. Application Data

(60) Provisional application No. 60/113,007, filed on Dec. 18, 1998.

(51) Int. Cl.$^7$ .................. A61K 31/33; A61K 31/404; C07D 209/00; C07D 209/04

(52) U.S. Cl. ............ 514/183; 514/80; 514/410; 514/415; 514/429; 548/400; 548/452; 548/469; 548/503; 548/511; 548/509

(58) Field of Search ................ 514/80, 183, 410, 514/415, 429; 548/400, 452, 469, 503, 511, 509

(56) References Cited

FOREIGN PATENT DOCUMENTS

| EP | 273418 | * | 7/1988 |
|---|---|---|---|
| HU | 192152 | | 4/1984 |
| JP | 02306916 | | 12/1990 |
| WO | WO 9822619 | | 5/1998 |
| WO | 9822619 | * | 5/1998 |
| WO | WO 9926933 | | 6/1999 |
| WO | WO 9926941 | | 6/1999 |

OTHER PUBLICATIONS

Chem. Abstract DN 110:85613, aslo cited as EP 273418.*
Chem. Abstract DN 10(:190304.*
Iwanowicz et al, Bioorg & Med. Chem. Letters 6/12, 1339–44(1996).*
Cecil Textbook of Medicine, Edited by Bennett & Plum, 1996, pp. 1004–1010.*
Uckum, et al,"Structure–based Design of Novel Anti–cancer Agts", Current Drg Targets,1,59–71(2001).*
Kaneko et al,PubMed.Abstract12708473, also cites as Cancer Sci., Urokinase–type plasminogen activator expr . . . , 94/1, 43–9(2003).*
Gronefeld et al, "Thromboempolic risk of Patients referred for radiofrequency.", PubMed Abstract 12687838, also cited as Pacin Clin. Electrophysiol., 26/1, 323–7(2003).*
De Lorenzo et al, PubMed Abstract 12656654, also cited as Drugs., :Blood Coagulation in patients., 63/6,565–76 (2003).*
Chemical Abstrac DN 110:85613, also cited as EP 273418 See CAS RN # 118234–55–2.*
McKinnon et al, Chemical Abstract DN 109:190304, also cited as Canadian J. Chem. 66/6, 1405–9(1988).*
Iwanowicz et al, Boorg & Med Chem Letr. 6/12, 1339–44 (1996).*
Tidwell R.R. et al. "Diarylamidine derivatives with one or both of th earyl moieties consisting of an indole or indole–like ring. Inhibitors of arginine–specific esteroproteases" *J. Med. Chem.* 1978, 21(7), 613–623.
Nishi T. et al. "Preparation of benzothiazoles and benzimidazoles as blood platelet aggregation inhibitors" Chemical Abstracts 1991, 114(21), 832.
Iwanowicz E.J. et al. "Derivatives of 5–amidine indole as inhibitors of thrombin catalytic activity" *Bioorganic & Medicinal Chemistry Letters* 1996, 6(12), 1339–1344.
Katz B.A. et al. "Design of potent selective zinc–mediated serine protease inhibitors" *Nature* 1998, 391, 608–612.

* cited by examiner

Primary Examiner—Richard L. Raymond
Assistant Examiner—Sudhaker B. Patel
(74) Attorney, Agent, or Firm—Townsend and Townsend and Crew LLP

(57) ABSTRACT

The present invention provides novel compounds of the Formula (I): A–B, its prodrug forms, or pharmaceutically acceptable salts thereof, wherein A represents a saturated, unsaturated, or a partially unsaturated bicyclic heterocyclic ring structure, and B represents an aryl or a heteroaryl group. Preferred compounds of the present invention comprise a benzimidazole or indole nucleus. The compounds of this invention are inhibitors of serine proteases, Urokinase (uPA), Factor Xa (FXa), and/or Factor VIIa (FVIIa), and have utility as anti cancer agents and/or as anticoagulants for the treatment or prevention of thromboembolic disorders in mammals.

13 Claims, No Drawings

(HETERO)ARYL-BICYCLIC HETEROARYL DERIVATIVES, THEIR PREPARATION AND THEIR USE AS PROTEASE INHIBITORS

FIELD OF INVENTION

The present invention relates to novel protease inhibitors.

BACKGROUND OF THE INVENTION

One of the most active areas in cancer research is the field of proteolytic enzymes and their role in the spread of cancer. One such class of protease that plays a significant role in the progression of cancer are the serine proteases, in particular Urokinase-type plasminogen activator (uPA). Inhibitors of uPA have been postulated to be of therapeutic value in treating cancer. Inhibitors of these serine proteases also tend to be inhibitors of the closely related blood-clotting enzymes. One such blood-clotting enzyme is Factor Xa.

Factor Xa (herein after "FXa"), the converting enzyme of pro-thrombin to thrombin, has emerged as an alternative (to thrombin) target for drug discovery for thromboembolic disorders. A variety of compounds have been developed as potential FXa inhibitors.

Kunitada and Nagahara in Current Pharmaceutical Design, 1996, Vol. 2, No.5, report amidinobenzyl compounds as FXa and thrombin inhibitors. Disclosed in U.S. Pat. No. 5,576,343 are aromatic amidine derivatives and salts thereof, as reversible inhibitors of FXa. These compounds comprise amidino substituted indolyl, benzofuranyl, benzothienyl, benzimidazolyl, benzoxazoyl, benzothiazolyl, naphthyl, tetrahydronaphthyl and indanyl groups, attached to a substituted phenyl ring by an alkylene group having from 1 to 4 carbon atoms.

In spite of the above discussed efforts, desirable treatment of cancer and thromboembolic disorders still remains elusive. There is thus a need for new compounds that will be effective in inhibiting serine proteases, such as Urokinase, and blood-clotting enzymes such as FXa. Keeping these needs in mind, the present invention provides novel inhibitors as discussed below.

SUMMARY OF THE INVENTION

The present invention relates to compounds of Formula I:

A—B its prodrug forms, or pharmaceutically acceptable salts thereof, wherein

A represents a saturated, unsaturated, or a partially unsaturated bicyclic heterocyclic ring structure substituted with $R^6$, $R^7$, $R^8$, $R^9$, and $R^{20}$;

B represents

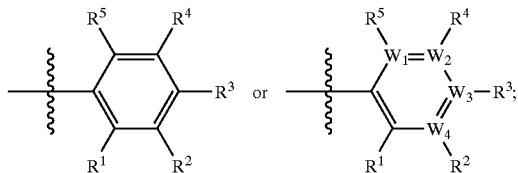

$R^1$ represents OH, halogen, COOH, COO—$O_{1-4}$ alkyl, O—$(CH_2)_{0-1}$—Ph, N($R^{10}$)$_2$, $CH_2OR^{10}$, $C_{1-6}$ halogenated alkyl, O—$(CH_2)_{1-4}$—CO—N($R^{10}$)$_2$, $SC_{1-4}$ alkyl, $NHSO_2C_{1-4}$alkyl, $SO_2$—OH, O—$SO_2$—OH, O—$SO_2$—O—$C_{1-4}$ alkyl, OP(O)(OH)$_2$, or $OPO_3C_{1-4}$ alkyl;

$R^2$, $R^3$, $R^4$, and $R^5$ independently at each occurance represent H, SH, $OR^{10}$, halogen, $COOR^{10}$, $CONR^{11}R^{12}$, optionally substituted aryl, optionally substituted heterocyclyl, $C_{4-14}$ cycloalkyl-$C_{1-4}$ alkyl, $C_{1-4}$ alkyl aryl, optionally substituted $C_{1-14}$ straight chain, branched or cyclo alkyl, O—$(C_2)_{2-6}$—$NR^{10}$—$(CH_2)_{0-3}$—$R^{24}$, $NR^{10}R^{24}$, $(CH_2)_{1-4}$—$NR^{33}R^{34}$, $(CH_2)_{1-4}$—$COOR^{33}$, O—$(CH_2)_{1-3}$—CO-het, O—$(CH_2)_{1-2}$—NH—CO-aryl, O—$(CH_2)_{1-2}$—$NR^{10}$—CO—$NR^{10}R^{33}$, O—$(CH_2)_{0-2}$—C(O)—$NR^{33}R^{34}$, O—$(CH_2)_{1-4}$—$COOR^{10}$, O—$(CH_2)_{1-3}$-het-$R^{32}$, O-optionally substituted cycloalkyl, O—$(CH_2)_{1-4}$—$NR^{10}$—COO-t-butyl, O—$(CH_2)_{1-4}$—$NR^{10}R^{33}$, O—$(CH_2)_{1-4}$—$NR^{10}$—C(O)—$C_{0-3}$-alkyl-optionally substituted aryl, O-substituted cycloalkyl, O—$(CH_2)_{0-6}$-optionally substituted aryl, $(CH_2)_{1-4}$—NH—C(O)O—$(CH_2)_{1-4}$—$PhR^{13}R^{14}$, $NO_2$, O—$(CH_2)_{0-4}$—C(O)—NH-tetrahydro carboline, $NR^{10}R^{28}$, O—$(CH_2)_{1-3}$-optionally substituted het, $CH_2COOCH_3$, CH=CH—$COOCH_3$, 5-amidino benzimidazole,

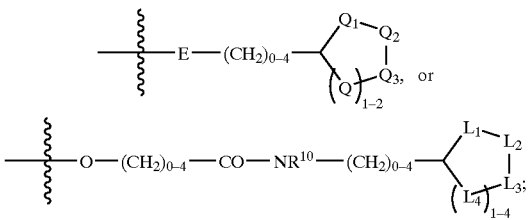

alternatively $R^2$ and $R^3$ taken together form

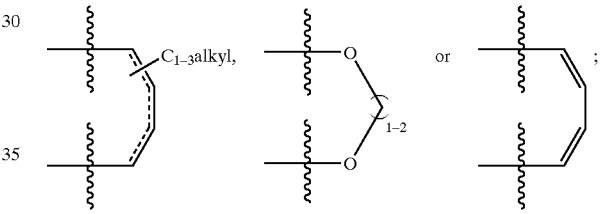

$R^6$ and $R^9$ independently at each occurance represents H, halogen, cyano, $C_{1-4}$ alkyl, $C_{1-4}$ halogenated alkyl, $NO_2$, O-aryl or $OR^{11}$;

$R^7$ and $R^8$ independently at each occurance represent OH, $CF_3$, H, $NO_2$, $C_{1-4}$ alkyl, $OC_{1-4}$ alkyl, or O-aryl, halogen, cyano, or a basic group selected from guanidino, C(=NH) N($R^{10}$)$_2$, C(=NH)—NH—$NH_2$, C(=O)$NH_2$, 2-imidazoline, N-amidinomorpholine, N-amidino piperidine, 4-hydroxy-N-amidino piperidine, N-amidino pyrrolidine, tetrahydro pyrimidine, and thiazolidin-3-yl-methylideneamine; with the proviso that only one of $R^7$ and $R^8$ represent a basic group;

$R^{10}$ independently at each occurance represents H, $(CH_2)_{0-2}$-aryl, $C_{1-4}$ halo alkyl, or $C_{1-14}$ straight chain, branched or cyclo alkyl, and alternatively, when one atom is substituted with two $R^{10}$ groups, the atom along with the $R^{10}$ groups can form a five to 10 membered ring structure;

$R^{11}$ and $R^{12}$ independently at each occurance represent H or $C_{1-4}$ alkyl;

$R^{20}$ represents $R^{24}$, $C_{1-4}$-alkyl, $(CH_2)_{1-3}$-biphenyl, $(CH_2)_{1-4}$—Ph—N($SO_2$—$C_{1-2}$-alkyl)$_2$, $(CH_2)_{1-4}$—NH—C(O)—$R^{24}$, $(CH_2)_{1-4}$—NH—$SO_2$—$R^{24}$, halogen, $COOR^{10}$, $(CH_2)_{1-4}$—Ph—N($SO_2$—$C_{1-2}$alkyl), $(CH_2)_{1-4}$—$NR^{10}$—C(O)—$R^{24}$, $(CH_2)_{1-4}$—$NR^{10}$—$SO_2$—$R^{24}$, $(CH_2)_{1-4}$-het, $(CH_2)_{1-4}$—CON($R^{10}$)$_2$, $(CH_2)_{1-4}$—N($R^{10}$)—C(O)—$NR^{10}R^{24}$, $(CH_2)_{1-4}$—N($R^{10}$)—C(S)—$NR^{10}R^{24}$, or $(CH_2)_{1-3}$—COOH;

$R^{24}$ represents $R^{10}$, $(CH_2)_{1-4}$-optionally substituted aryl, $(CH_2)_{0-4}OR^{10}$, CO—$(CH_2)_{1-2}$—N($R^{10}$)$_2$, CO($CH_2$)$_{1-4}$—

$OR^{10}$, $(CH_2)_{1-4}$—$COOR^{10}$, $(CH_2)_{0-4}$—$NR(R^{10})_2$, $SO_2R^{10}$, $COR^{10}$, $CON(R^{10})_2$, $(CH_2)_{0-4}$-aryl-$COOR^{10}$, $(CH_2)_{0-4}$-aryl-$N(R^{10})_2$, or $(CH_2)_{1-4}$-het-aryl;

$R^{28}$ represents $(CH_2)_{1-2}$—Ph—O—$(CH_2)_{0-2}$-het-$R^{30}$, C(O)-het, $CH_2$—Ph—$CH_2$-het-$(R^{30})_{1-3}$; $(CH_2)_{1-4}$-cyclohexyl-$R^{11}$, $CH_2$—Ph—O—Ph—$(R^{30})_{1-2}$, $CH_2$—$(CH_2OH)$-het-$R^{10}$, $CH_2$—Ph—O-cycloalkyl-$R^{31}$, $CH_2$-het-C(O)—$CH_2$-het-$R^{30}$, or $CH_2$—Ph—O—$(CH_2)$—O-het-$R^{30}$;

$R^{30}$ represents $SO_2N(R^{10})_2$, H, NHOH, amidino, or $C(=NH)CH_3$;

$R^{31}$ represents $R^{30}$, amino-amidino, NH—$C(=NH)CH_3$ or $R^{10}$;

$R^{32}$ represents H, C(O)—$CH_2$—$NH_2$, or C(O)—CH(CH($CH_3$)$_2$)—$NH_2$;

$R^{33}$ and $R^{36}$ independently at each occurance represent $R^{10}$, $(CH_2)_{0-2}$—Ar, optionally substituted aryl, $(CH_2)_{0-4}$, optionally substituted heteroaryl, $(CH_2)_{1-4}$—CN, $(CH_2)_{1-4}$—$N(R^{10})_2$, $(CH_2)_{1-4}$—OH, $(CH_2)_{1-4}$—$SO_2$—$N(R^{10})_2$;

alternatively, $R^{33}$ and $R^{34}$ along with the nitrogen atom that they are attached to forms a 4 to 14 atom ring structure selected from tetrahydro-1H-carboline; 6,7-Dialkoxyoxy-2-substituted 1,2,3,4-tetrahydro-isoquinoline,

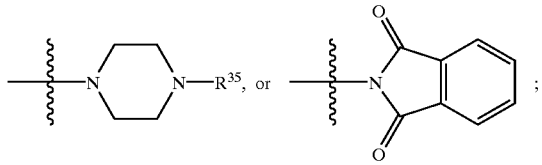

$R^{35}$ represents $R^{10}$, $SO_2$—$R^{10}$, $COR^{10}$, or $CONHR^{10}$;
E represents a bond, $S(O)_{0-2}$, O or $NR^{10}$;
$W_1$, $W_2$, $W_3$ and $W_4$ independently represent C or N; and Q, $Q^1$, $Q^2$, $Q^3$, $L^1$, $L^2$, $L^3$ and $L^4$ independently at each occurance represent N-natural or unnatural amino acid side chain, $CHR^{10}$, O, NH, $S(O)_{0-2}$, N—C(O)—$NHR^{10}$, $SO_2$—$N(R^{10})_2$, N—C(O)—NH—$(CH_2)_{1-4}$—$R^{26}$, $NR^{10}$, N-heteroaryl, N—$C(=NH)$—$NHR^{10}$, or N—$C(=NH)C_{1-4}$ alkyl;

$R^{26}$ represents OH, $NH_2$, or SH;
provided that, (i) when $R^1$=OH; $R^7$=amidine; $R^2$, $R^6$, $R^8$, $R^9$, and $R^{20}$ each represent H; and $R^3$, $R^4$, $R^5$ are independently chosen from H, $CH_3$, and halogen, then only one of $R^3$, $R^4$, and $R^5$ represents H; (ii) when $R^1$=OH; $R^7$=amidine; $R^2$, $R^3$, $R^4$, $R^5$, and $R^{20}$ each represent H; and $R^6$, $R^8$, $R^9$ are independently chosen from H, $CH_3$, and halogen, then only one of $R^6$, $R^8$, and $R^9$ represents H; (iii) at least two of $W_1$, $W_2$, $W_3$ and $W_4$ represent C and at least one of $W_1$, $W_2$, $W_3$ and $W_4$ represent N; and (iv) when $R^1$=OH; $R^7$=amidine; and $R^2$, $R^3$, $R^4$, $R^5$, $R^6$, $R^8$, and $R^9$, represent H, $R^{20}$ cannot be $CH_3$.

Also provided by the present invention is a pharmaceutical composition comprising a pharmaceutically acceptable carrier and a therapeutically effective amount of a compound of Formula I or a pharmaceutically acceptable salt thereof.

The present invention also provides a method for treating or preventing a thromboembolic disorder, comprising administering to a patient in need thereof a therapeutically effective amount of a compound of Formula I or a pharmaceutically acceptable salt thereof.

DETAILED DESCRIPTION OF THE INVENTION

Provided by the present invention is a compound of Formula I:

A—B its prodrug forms, or pharmaceutically acceptable salts thereof, wherein

A represents a saturated, unsaturated, or a partially unsaturated bicyclic heterocyclic ring structure substituted with $R^6$, $R^7$, $R^8$, $R^9$, and $R^{20}$;
B represents

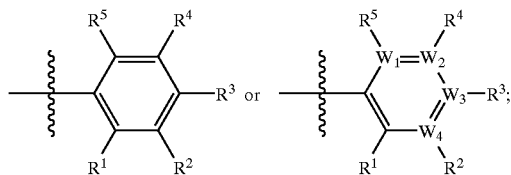

$R^1$ represents OH, halogen, COOH, COO—$O_{1-4}$ alkyl, O—$(CH_2)_{0-1}$—Ph, $N(R^{10})_2$, $CH_2OR^{10}$, $C_{1-6}$ halogenated alkyl, O—$(CH_2)_{1-4}$—CO—$N(R^{10})_2$, $SC_{1-4}$ alkyl, $NHSO_2C_{1-4}$alkyl, $SO_2$—OH, O—$SO_2$—OH, O—$SO_2$—O—$C_{1-4}$ alkyl, $OP(O)(OH)_2$, or $OPO_3C_{1-4}$ alkyl;

$R^2$, $R^3$, $R^4$, and $R^5$ independently at each occurance represent H, SH, $OR^{10}$, halogen, $COOR^{10}$, $CONR^{11}R^{12}$, optionally substituted aryl, optionally substituted heterocyclyl, $C_{4-14}$ cycloalkyl-$C_{1-4}$ alkyl, $C_{1-4}$ alkyl aryl, optionally substituted $C_{1-14}$ straight chain, branched or cyclo alkyl, O—$(CH_2)_{2-6}$—$NR^{10}$—$(CH_2)_{0-3}$—$R^{24}$, $NR^{10}R^{24}$, $(CH_2)_{1-4}$—$NR^{33}R^{34}$, $(CH_2)_{1-4}$—$COOR^{33}$, O—$(CH_2)_{1-3}$CO-het, O—$(CH_2)_{1-2}$—NH—CO-aryl, O—$(CH_2)_{1-2}$—$NR^{10}$—CO—$NR^{10}R^{33}$, O—$(CH_2)_{0-2}$—(O)—$NR^{33}R^{34}$, O—$(CH_2)_{1-4}$—$COOR^{10}$, O—$(CH_2)_{1-3}$-het-$R^{32}$, O-optionally substituted cycloalkyl, O—$(CH_2)_{1-4}$—$NR^{10}$—COO-t-butyl, O—$(CH_2)_{1-4}$—$NR^{10}R^{33}$, O—$(CH_2)_{1-4}$—$NR^{10}$—C(O)—$C_{0-3}$-alkyl-optionally substituted aryl, O-substituted cycloalkyl, O—$(CH_2)_{0-6}$-optionally substituted aryl, $(CH_2)_{1-4}$—NH—$C(O)O$—$(CH_2)_{1-4}$—$PhR^{33}R^{34}$, $NO_2$, O—$(CH_2)_{0-4}$—C(O)—NH-tetrahydro carboline, $NR^{10}R^{28}$, O—$(CH_2)_{1-3}$-optionally substituted het, $CH_2COOCH_3$, CH=CH—$COOCH_2$, 5-amidino benzimidazole,

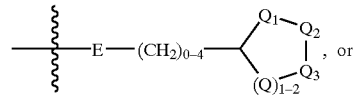

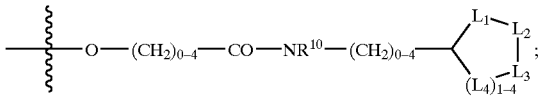

alternatively $R^2$ and $R^3$ taken together form

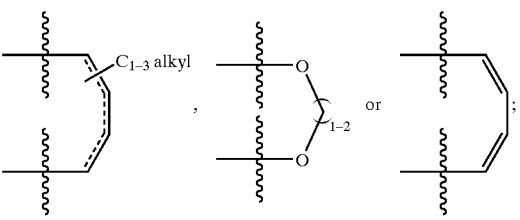

$R^6$ and $R^9$ independently at each occurance represents H, halogen, cyano, $C_{1-4}$ alkyl, $C_{1-4}$ halogenated alkyl, $NO_2$, O-aryl or $OR^{11}$;

$R^7$ and $R^8$ independently at each occurance represent OH, $CF_3$, H, $NO_2$, $C_{1-4}$ alkyl, $OC_{1-4}$ alkyl, or O-aryl, halogen, cyano, or a basic group selected from guanidino, $C(=NH)N(R^{10})_2$, $C(=NH)$—NH—$NH_2$, $C(=O)NH_2$, 2-imidazoline, N-amidinomorpholine, N-amidino piperidine, 4-hydroxy-N-amidino piperidine, N-amidino pyrrolidine, tetrahydro pyrimidine, and thiazolidin-3-yl-methylideneamine; with the proviso that only one of $R^7$ and $R^8$ represent a basic group;

$R^{10}$ independently at each occurance represents H, $(CH_2)_{0-2}$-aryl, $C_{1-4}$ halo alkyl, or $C_{1-14}$ straight chain, branched or cyclo alkyl, and alternatively, when one atom is substituted with two $R^{10}$ groups, the atom along with the $R^{10}$ groups can form a five to 10 membered ring structure;

$R^{11}$ and $R^{12}$ independently at each occurance represent H or $C_{1-4}$ alkyl;

$R^{20}$ represents $R^{24}$, $C_{1-4}$-alkyl, $(CH_2)_{1-3}$-biphenyl, $(CH_2)_{1-4}$—Ph—$N(SO_2$—$C_{1-2}$-alkyl$)_2$, $(CH_2)_{1-4}$—NH—C(O)—$R^{24}$, $(CH_2)_{1-4}$—NH—$SO_2$—$R^{24}$, halogen, $COOR^{10}$, $(CH_2)_{1-4}$—Ph—$N(SO_2$—$C_{1-2}$alkyl), $(CH_2)_{1-4}$—$NR^{10}$—C(O)—$R^{24}$, $(CH_2)_{1-4}$—$NR^{10}$—$SO_2$—$R^{24}$, $(CH_2)_{1-4}$-het, $(CH_2)_{1-4}$—$CON(R^{10})_2$, $(CH_2)_{1-6}$—$N(R^{10})$—C(O)—$NR^{10}R^{24}$, $(CH_2)_{1-4}$—$N(R^{10})$—C(S)—$NR^{10}R^{24}$, or $(CH_2)_{1-3}$—COOH;

$R^{24}$ represents $R^{10}$, $(CH_2)_{1-4}$-optionally substituted aryl, $(CH_2)_{0-4}OR^{10}$, CO—$(CH_2)_{1-2}$—$N(R^{10})_2$, $CO(CH_2)_{1-4}$—$OR^{10}$, $(CH_2)_{1-4}$—$COOR^{10}$, $(CH_2)_{0-4}$—$N(R^{10})_2$, $SO_2R^{10}$, $COR^{10}$, $CON(R^{10})_2$, $(CH_2)_{0-4}$-aryl-$COOR^{10}$, $(CH_2)_{0-4}$-aryl-$N(R^{10})_2$, or $(CH_2)_{1-4}$-het-aryl;

$R^{28}$ represents $(CH_2)_{1-2}$—Ph—O—$(CH_2)_{0-2}$-het-$R^{30}$, C(O)-het, $CH_2$—Ph—$CH_2$-het-$(R^{30})_{1-3}$; $(CH_2)_{1-4}$-cyclohexyl-$R^{31}$, $CH_2$—Ph—O—Ph—$(R^{30})_{1-2}$, $CH_2$—$(CH_2OH)$-het-$R^{30}$, $CH_2$—Ph—O-cycloalkyl-$R^{31}$, $CH_2$-het-C(O)—$CH_2$-het-$R^{30}$, or $CH_2$—Ph—O—$(CH_2)$—O-het-$R^{30}$;

$R^{30}$ represents $SO_2N(R^{10})_2$, H, NHOH, amidino, or C(=NH)$CH_3$;

$R^{31}$ represents $R^{30}$, amino-amidino, NH—C(=NH)$CH_3$ or $R^{10}$;

$R^{32}$ represents H, C(O)—$CH_2$—$NH_2$, or C(O)—CH(CH($CH_3$)$_2$)—$NH_2$;

$R^{33}$ and $R^{34}$ independently at each occurance represent $R^{10}$, $(CH_2)_{0-4}$—Ar, optionally substituted aryl, $(CH_2)_{0-4}$ optionally substituted heteroaryl, $(CH_2)_{1-4}$—CN, $(CH_2)_{1-4}$—$N(R^{10})_2$, $(CH_2)_{1-4}$—OH, $(CH_2)_{1-4}$—$SO_2$—N$(R^{10})_2$;

alternatively, $R^{33}$ and $R^{34}$ along with the nitrogen atom that they are attached to forms a 4 to 14 atom ring structure selected from tetrahydro-1H-carboline; 6,7-Dialkoxyoxy-2-substituted 1,2,3,4-tetrahydro-isoquinoline,

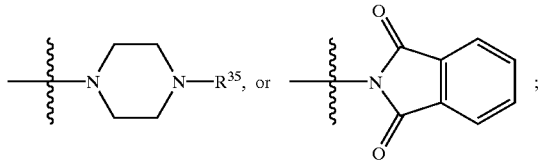

$R^{35}$ represents $R^{10}$, $SO_2$—$R^{10}$, $COR^{10}$, or $CONHR^{10}$;

E represents a bond, $S(O)_{0-2}$, O or $NR^{10}$;

$W_1$, $W_2$, $W_3$ and $W_4$ independently represent C or N; and

Q, $Q^1$, $Q^2$, $Q^3$, $L^1$, $L^2$, $L^3$ and $L^4$ independently at each occurance represent N-natural or unnatural amino acid side chain, $CHR^{10}$, O, NH, $S(O)_{0-2}$, N—C(O)—$NHR^{10}$, $SO_2$—$N(R^{10})_2$, N—C(O)—NH—$(CH_2)_{1-4}$—$R^{26}$, $NR^{10}$, N-heteroaryl, N—C(=NH)—$NHR^{10}$, or N—C(=NH)$C_{1-4}$ alkyl;

$R^{26}$ represents OH, $NH_2$, or SH;

provided that, (i) when $R^1$=OH; $R^7$=amidine; $R^2$, $R^6$, $R^8$, $R^9$, and $R^{20}$ each represent H; and $R^3$, $R^4$, $R^5$ are independently chosen from H, $CH_3$, and halogen, then only one of $R^3$, $R^4$, and $R^5$ represents H; (ii) when $R^1$=OH; $R^7$=amidine; $R^2$, $R^3$, $R^4$, $R^5$, and $R^{20}$ each represent H; and $R^6$, $R^8$, $R^9$ are independently chosen from H, $CH_3$, and halogen, then only one of $R^6$, $R^8$, and $R^9$ represents H; (iii) at least two of $W_1$, $W_2$, $W_3$ and $W_4$ represent C and at least one of $W_1$, $W_2$, $W_3$ and $W_4$ represent N; and (iv) when $R^1$=OH;

$R^7$=amidine; and $R^2$, $R^3$, $R^4$, $R^5$, $R^6$, $R^8$, and $R^9$, represent H, $R^{20}$ cannot be $CH_3$.

A preferred embodiment of the present invention provides a compound of Formula I:

A—B     Formula I its prodrug forms, or pharmaceutically acceptable salts thereof, wherein A represents

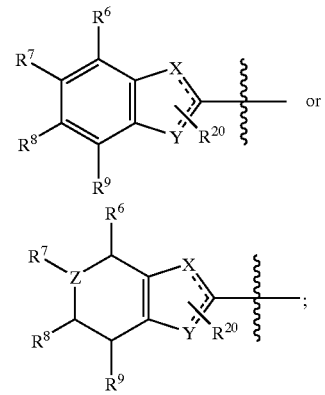

B represents

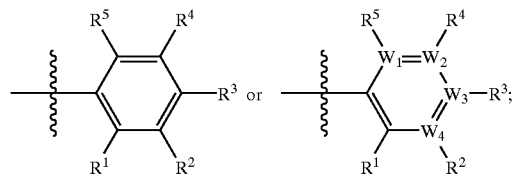

$R^1$ represents OH, halogen, COOH, COO—$O_{1-4}$ alkyl, O—$(CH_2)_{0-1}$—Ph, $N(R^{10})_2$, $CH_2OR^{10}$, $C_{1-6}$ halogenated alkyl, O—$(CH_2)_{1-4}$—CO—$N(R^{10})_2$, $SC_{1-4}$ alkyl, $NHSO_2C_{1-4}$alkyl, $SO_2$—OH, O—$SO_2$—OH, O—$SO_2$—O—$C_{1-4}$ alkyl, $OP(O)(OH)_2$, or $OPO_3C_{1-4}$ alkyl;

$R^2$, $R^3$, $R^4$, and $R^5$ independently at each occurance represent H, SH, $OR^{10}$, halogen, $COOR^{10}$, $CONR^{11}R^{12}$, optionally substituted aryl, optionally substituted heterocyclyl, $C_{4-14}$ cycloalkyl-$C_{1-4}$ alkyl, $C_{1-4}$ alkyl aryl, optionally substituted $C_{1-14}$ straight chain, branched or cyclo alkyl, O—$(CH_2)_{2-6}$—$NR^{10}$—$(CH_2)_{0-3}$—$R^{24}$, $NR^{10}R^{24}$, $(CH_2)_{1-4}$—$NR^{33}R^{34}$, $(CH_2)_{1-4}$—$COOR^{33}$, O—$C(H_2)_{1-3}$—CO-het, O—$(CH_2)_{1-2}$—NH—CO-aryl, O—$(CH_2)_{1-2}$—$NR^{10}$—CO—$NR^{10}R^{33}$, O—$(CH_2)_{0-2}$—C(O)—$NR^{33}R^{34}$, O—$(CH_2)_{1-4}$—$COOR^{10}$, O—$(CH_2)_{1-3}$-het-$R^{32}$, O-optionally substituted cycloalkyl, O—$(CH_2)_{1-4}$—$NR^{10}$—COO-t-butyl, O—$(CH_2)_{1-4}$—$NR^{10}R^{33}$, O—$(CH_2)_{1-4}$—$NR^{10}$—C(O)—$CO_{0-3}$-alkyl-optionally substituted aryl, O-substituted cycloalkyl, O—$(CH_2)_{0-6}$-optionally substituted aryl, $(CH_2)_{1-4}$—NH—C(O)O—$(CH_2)_{1-4}$—$PhR^{13}R^{14}$, $NO_2$, O—$(CH_2)_{0-4}$—C(O)—NH-tetrahydro carboline, $NR^{10}R^{28}$, O—$(CH_2)_{1-3}$-optionally substituted het, $CH_2COOCH_3$, CH=CH—$COOCH_3$, 5-amidino benzimidazole, , or

;

alternatively $R^2$ and $R^3$ taken together form

;

$R^6$ and $R^9$ independently at each occurance represents H, halogen, cyano, $C_{1-4}$ alkyl, $C_{1-4}$ halogenated alkyl, $NO_2$, O-aryl or $OR^{11}$;

$R^7$ and $R^8$ independently at each occurance represent OH, $CF_3$, H, $NO_2$, $C_{1-4}$ alkyl, $OC_{1-4}$ alkyl, or O-aryl, halogen, cyano, or a basic group selected from guanidino, C(=NH)N$(R^{10})_2$, C(=NH)—NH—$NH_2$, C(=O)$NH_2$, 2-imidazoline, N-amidinomorpholine, N-amidino piperidine, 4-hydroxy-N-amidino piperidine, N-amidino pyrrolidine, tetrahydro pyrimidine, and thiazolidin-3-yl-methylideneamine; with the proviso that only one of $R^7$ and $R^8$ represent a basic group;

$R^{10}$ independently at each occurance represents H, $(CH_2)_{0-2}$-aryl, $C_{1-4}$ halo alkyl, or $C_{1-14}$ straight chain, branched or cyclo alkyl, and alternatively, when one atom is substituted with two $R^{10}$ groups, the atom along with the $R^{10}$ groups can form a five to 10 membered ring structure;

$R^{11}$ and $R^{12}$ independently at each occurance represent H or $C_{1-4}$ alkyl;

$R^{20}$ represents $R^{24}$, $C_{1-4}$-alkyl, $(CH_2)_{1-3}$-biphenyl, $(CH_2)_{1-4}$—Ph—N$(SO_2$—$C_{1-2}$-alkyl$)_2$, $(CH_2)_{1-4}$—NH—C(O)—$R^{24}$, $(CH_2)_{1-4}$—NH—$SO_2$—$R^{24}$, halogen, $COOR^{10}$, $(CH_2)_{1-4}$—Ph—N$(SO_2$—$C_{1-2}$alkyl), $(CH_2)_{1-4}$—$NR^{10}$—C(O)—$R^{24}$, $(CH_2)_{1-4}$—$NR^{10}$—$SO_2$—$R^{24}$, $(CH_2)_{1-4}$-het, $(CH_2)_{1-4}$—CON$(R^{10})_2$, $(CH_2)_{1-4}$—N$(R^{10})$—C(O)—$NR^{10}R^{24}$, $(CH_2)_{1-4}$—N$(R^{10})$—C(S)—$NR^{10}R^{24}$, or $(CH_2)_{1-3}$—COOH;

$R^{24}$ represents $R^{10}$, $(CH_2)_{1-4}$-optionally substituted aryl, $(CH_2)_{0-4}$—$OR^{10}$, CO—$(CH_2)_{1-2}$—N$(R^{10})_2$, CO$(CH_2)_{1-4}$—$OR^{10}$, $(CH_2)_{1-4}$—$COOR^{10}$, $(CH_2)_{0-4}$—N$(R^{10})_2$, $SO_2R^{10}$, $COR^{10}$, CON$(R^{10})_2$, $(CH_2)_{0-4}$-aryl-$COOR^{10}$, $(CH_2)_{0-4}$-aryl-N$(R^{10})_2$, or $(CH_2)_{1-4}$-het-aryl;

$R^{28}$ represents $(CH_2)_{1-2}$—Ph—O—$(CH_2)_{0-2}$-het-$R^{30}$, C(O)-het, $CH_2$—Ph—$CH_2$-het-$(R^{30})_{1-3}$; $(CH_2)_{1-4}$-cyclohexyl-$R^{31}$, $CH_2$—Ph—O—Ph—$(R^{30})_{1-2}$, $CH_2$—$(CH_2OH)$-het-$R^{30}$, $CH_2$—Ph—O-cycloalkyl-$R^{31}$, $CH_2$—C(O)—$CH_2$-het-$R^{30}$, or $CH_2$—Ph—O—$(CH_2)$—O-het-$R^{30}$;

$R^{30}$ represents $SO_2N(R^{10})_2$, H, NHOH, amidino, or C(=NH)$CH_3$;

$R^{31}$ represents $R^{30}$, amino-amidino, NH—C(=NH)$CH_3$ or $R^{10}$;

$R^{32}$ represents H, C(O)—$CH_2$—$NH_2$, or C(O)—CH(CH$(CH_3)_2$)—$NH_2$;

$R^{33}$ and $R^{34}$ independently at each occurance represent $R^{10}$, $(CH_2)_{0-4}$—Ar, optionally substituted aryl, $(CH_2)_{0-4}$-optionally substituted heteroaryl, $(CH_2)_{1-4}$—CN, $(CH_2)_{1-4}$—N$(R^{10})_2$, $(CH_2)_{1-4}$—OH, $(CH_2)_{1-4}$—$SO_2$—N$(R^{10})_2$;

alternatively, $R^{33}$ and $R^{34}$ along with the nitrogen atom that they are attached to forms a 4 to 14 atom ring structure selected from tetrahydro-1H-carboline; 6,7-Dialkoxyoxy-2-substituted 1,2,3,4-tetrahydro-isoquinoline, , or ;

$R^{35}$ represents $R^{10}$, $SO_2$—$R^{10}$, $COR^{10}$, or $CONHR^{10}$;

E represents a bond, $S(O)_{0-2}$, O or $NR^{10}$;

$W_1$, $W_2$, $W_3$ and $W_4$ independently represent C or N; and

Q, $Q^1$, $Q^2$, $Q^3$, $L^1$, $L^2$, $L^3$ and $L^4$ independently at each occurance represent N-natural or unnatural amino acid side chain, $CHR^{10}$, O, NH, $S(O)_{0-2}$, N—C(O)—$NHR^{10}$, $SO_2$—N$(R^{10})_2$, N—C(O)—NH—$(CH_2)_{1-4}$—$R^{26}$, $NR^{10}$, N-heteroaryl, N—C(=NH)—$NHR^{10}$, or N—C(=NH)$C_{1-4}$ alkyl;

$R^{26}$ represents OH, $NH_2$, or SH;

provided that, (i) when $R^1$=OH; $R^7$=amidine; $R^2$, $R^6$, $R^8$, $R^9$, and $R^{20}$ each represent H; and $R^3$, $R^4$, $R^5$ are independently chosen from H, $CH_3$, and halogen, then only one of $R^3$, $R^4$, and $R^5$ represents H; (ii) when $R^1$=OH; $R^7$=amidine; $R^2$, $R^3$, $R^4$, $R^5$, and $R^{20}$ each represent H; and $R^6$, $R^8$, $R^9$ are independently chosen from H, $CH_3$, and halogen, then only one of $R^6$, $R^8$, and $R^9$ represents H; (iii) at least two of $W_1$, $W_2$, $W_3$ and $W_4$ represent C and at least one of $W_1$, $W_2$, $W_3$ and $W_4$ represent N; and (iv) when $R^1$=OH; $R^7$=amidine; and $R^2$, $R^3$, $R^4$, $R^5$, $R^6$, $R^8$, and $R^9$, represent H, $R^{20}$ cannot be $CH_3$.

A further preferred embodiment provides a compound of Formula I wherein:

A—B its prodrug forms, or pharmaceutically acceptable salts thereof, wherein

A represents or

;

B represents

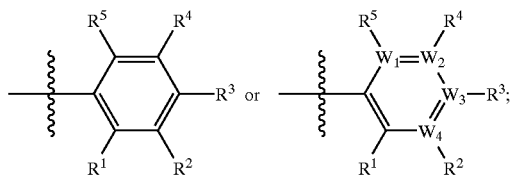

R¹ represents OH, halogen, COOH, COO—C₁₋₄ alkyl, O—(CH₂)₀₋₁—Ph, N(R¹⁰), CH₂OR¹⁰, C₁₋₆ halogenated alkyl, O—(CH₂)₁₋₄—CO—N(R¹⁰)₂, SC₁₋₄ alkyl, NHSO₂C₁₋₄alkyl, SO₂—OH, O—SO₂—OH, O—SO₂—O—C₁₋₄ alkyl, OP(O)(OH)₂, or OPO₃C₁₋₄ alkyl;

R², R³, R⁴, and R⁵ independently at each occurance represent H, SH, OR¹⁰, halogen, COOR¹⁰, CONR¹¹R¹², optionally substituted aryl, optionally substituted heterocyclyl, C₄₋₁₄ cycloalkyl-C₁₋₄ alkyl, C₁₋₄ alkyl aryl, optionally substituted C₁₋₁₄ straight chain, branched or cyclo alkyl, O—(CH₂)₂₋₆—NR¹⁰—(CH₂)₀₋₃—R²⁴, NR¹⁰R²⁴, (CH₂)₁₋₄—NR³³R³⁴, (CH₂)₁₋₄—COOR³³, O—(CH₂)₁₋₃—CO-het, O—(CH₂)₁₋₂—NH—CO-aryl, O—(CH₂)₁₋₂—NR¹⁰—CO—NR¹⁰R³³, O—(CH₂)₀₋₂—C(O)—NR³³R³⁴, O—(CH₂)₁₋₄—COOR¹⁰, O—(CH₂)₁₋₃-het-R³², O-optionally substituted cycloalkyl, O—(CH₂)₁₋₄—NR¹⁰—COO-t-butyl, O—(CH₂)₁₋₄—NR¹⁰R³³, O—(CH₂)₁₋₄—NR¹⁰—C(O)—C₀₋₃-alkyl-optionally substituted aryl, O-substituted cycloalkyl, O—(CH₂)₀₋₆-optionally substituted aryl, (CH₂)₁₋₄—NH—C(O)O—(CH₂)₁₋₄—PhR¹³R¹⁴, NO₂, O—(CH₂)₀₋₄—C(O)—NH-tetrahydro carboline, NR¹⁰R²⁸, O—(CH₂)₁₋₃-optionally substituted het, CH₂COOCH₃, CH=CH—COOCH₃, 5-amidino benzimidazole,

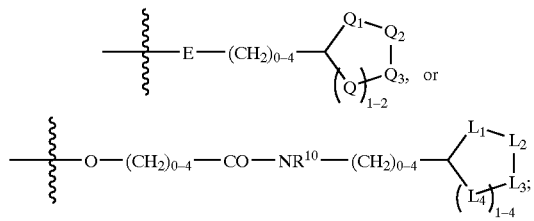

alternatively R² and R³ taken together form

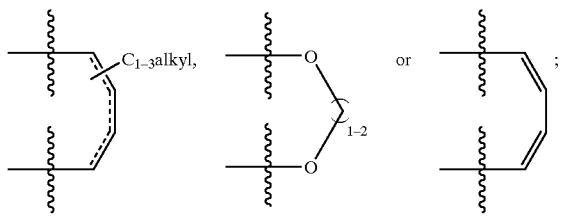

R⁶ and R⁹ independently at each occurance represents H, halogen, Cyano, C₁₋₄ alkyl, C₁₋₄ halogenated alkyl, NO₂, O-aryl or OR¹¹;

R⁷ and R⁸ independently at each occurance represent OH, CF₃, H, NO₂, C₁₋₄ alkyl, OC₁₋₄ alkyl, or O-aryl, halogen, cyano, or a basic group selected from guanidino, C(=NH)N(R¹⁰)₂, C(=NH)—NH—NH₂, C(=O)NH₂, 2-imidazoline, N-amidinomorpholine, N-amidino piperidine, 4-hydroxy-N-amidino piperidine, N-amidino pyrrolidine, tetrahydro pyrimidine, and thiazolidin-3-yl-methylideneamine; with the proviso that only one of R⁷ and R⁸ represent a basic group;

R¹⁰ independently at each occurance represents H, (CH₂)₀₋₂-aryl, C₁₋₄ halo alkyl, or C₁₋₁₄ straight chain, branched or cyclo alkyl, and alternatively, when one atom is substituted with two R¹⁰ groups, the atom along with the R¹⁰ groups can form a five to 10 membered ring structure;

R¹¹ and R¹² independently at each occurance represent H or C₁₋₄ alkyl;

R²⁰ represents R²⁴, C₁₋₄-alkyl, (CH₂)₁₋₃-biphenyl, (CH₂)₁₋₄—Ph—N(SO₂—C₁₋₂-alkyl)₂, (CH₂)₁₋₄—NH—C(O)—R²⁴, (CH₂)₁₋₄—NH—SO₂—R²⁴, halogen, COOR¹⁰, (CH₂)₁₋₄—Ph—N(SO₂—C₁₋₂alkyl), (CH₂)₁₋₄—NR¹⁰—C(O)—R²⁴, (CH₂)₁₋₄—NR¹⁰—SO₂—R²⁴, (CH₂)₁₋₄-het, (CH₂)₁₋₄—CON(R¹⁰)₂, (CH₂)₁₋₄—N(R¹⁰)—C(O)—NR¹⁰R²⁴, (CH₂)₁₋₄—N(R¹⁰)—C(S)—NR¹⁰R²⁴, or (CH₂)₁₋₃—COOH;

R²⁴ represents R¹⁰, (CH₂)₁₋₄-optionally substituted aryl, (CH₂)₀₋₄—OR¹⁰, CO—(CH₂)₁₋₂—N(R¹⁰)₂, CO(CH₂)₁₋₄—OR¹⁰, (CH₂)₁₋₄—COOR¹⁰, (CH₂)₀₋₄—N(R¹⁰)₂, SO₂R¹⁰, COR¹⁰, CON(R¹⁰)₂, (CH₂)₀₋₄-aryl-COOR¹⁰, (CH₂)₀₋₄-aryl-N(R¹⁰)₂, or (CH₂)₁₋₄-het-aryl;

R²⁸ represents (CH₂)₁₋₂—Ph—O—(CH₂)₀₋₂-het-R³⁰, C(O)-het, CH₂—Ph—CH₂-het-(R¹⁰)₁₋₃; (CH₂)₁₋₄-cyclohexyl-R³¹, CH₂—Ph—O—Ph—(R³⁰)₁₋₂, CH₂—(CH₂OH)-het-R³⁰, CH₂—Ph—O-cycloalkyl-R³¹, CH₂-het-C(O)—CH₂-het-R³⁰, or CH₂—Ph—O—(CH₂)—O-het-R³⁰;

R³⁰ represents SO₂N(R¹⁰)₂, H, NHOH, amidino, or C(=NH)CH₃;

R³¹ represents R³⁰, amino-amidino, NH—C(=NH)CH₃ or R¹⁰;

R³² represents H, C(O)—CH₂—NH₂, or C(O)—CH(CH(CH₃)₂)—NH₂;

R³³ and R³⁴ independently at each occurance represent R¹⁰, (CH₂)₀₋₄—Ar, optionally substituted aryl, (CH₂)₀₋₄ optionally substituted heteroaryl, (CH₂)₁₋₄—CN, (CH₂)₁₋₄—N(R¹⁰)₂, (CH₂)₁₋₄—OH, (CH₂)₁₋₄—SO₂—N(R¹⁰)₂;

alternatively, R³³ and R³⁴ along with the nitrogen atom that they are attached to forms a 4 to 14 atom ring structure selected from tetrahydro-1H-carboline; 6,7-Dialkoxyoxy-2-substituted 1,2,3,4-tetrahydro-isoquinoline,

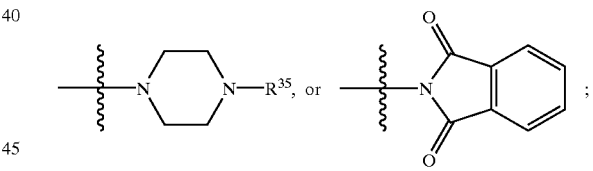

R³⁵ represents R¹⁰, SO₂—R¹⁰, COR¹⁰, or CONHR¹⁰,

E represents a bond, S(O)₀₋₂, O or NR¹⁰;

W₁, W₂, W₃ and W₄ independently represent C or N; and Q, Q¹, Q², Q³, L¹, L², L³ and L⁴ independently at each occurance represent N-natural or unnatural amino acid side chain, CHR¹⁰, O, NH, S(O)₀₋₂, N—C(O)—NHR¹⁰, SO₂—N(R¹⁰)₂, N—C(O)—NH—(CH₂)₁₋₄—R²⁶, NR¹⁰, N-heteroaryl, N—C(=NH)—NHR¹⁰, or N—C(=NH)C₁₋₄ alkyl;

R²⁶ represents OH, NH₂, or SH;

provided that, (i) when R¹=OH; R⁷=amidine; R², R⁶, R⁸, R⁹, and R²⁰ each represent H; and R³, R⁴, R⁵ are independently chosen from H, CH₃, and halogen, then only one of R³, R⁴, and R⁵ represents H; (ii) when R¹=OH; R⁷=amidine; R², R³, R⁴, R⁵, and R²⁰ each represent H; and R⁶, R⁸, R⁹ are independently chosen from H, CH₃, and halogen, then only one of R⁶, R⁸, and R⁹ represents H; (iii) at least two of W₁, W₂, W₃ and W₄ represent C and at least one of W₁, W₂, W₃ and W₄ represent N; and (iv) when R¹=OH; R⁷=amidine; and R², R³, R⁴, R⁵, R⁶, R⁸, and R⁹, represent H, R²⁰ cannot be CH₃.

A further preferred embodiment provides a compound of Formula I wherein,

A represents

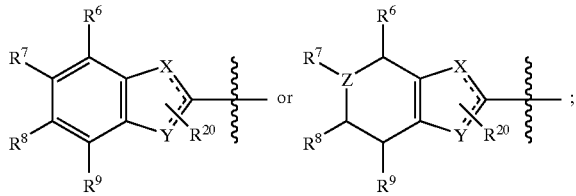

$R^1$ represents OH, O—Ph, COOH, or P(O)(OH)$_2$;

$R^7$ represents H, Br, CONH$_2$, CN, C(=NH)—NH—NH$_2$, NH—C(=NH)—NH$_2$ or C(=NH)—NH$_2$;

$R^{20}$ represents H, C$_{1-2}$ alkyl, (CH$_2$)$_{1-4}$-optionally substituted aryl, (CH$_2$)$_{1-4}$-het; (CH$_2$)$_{1-4}$—N(R$^{10}$)$_2$, (CN$_2$)$_{1-4}$—CON(R$^{10}$)$_2$, (CH$_2$)$_{1-4}$—NR$^{10}$—C(O)—R$^{24}$, (CH$_2$)$_{1-4}$—NR$^{10}$—SO$_2$—R$^{24}$, or (CH$_2$)$_{1-3}$—COOH;

X and Y independently at each occurance are selected from NH, N, C, or CH, such that at least one of X and Y always represents N or NH ; and Z represents C or N;

provided that, (i) when Z represents N, R$^7$ represents H or C(=NH)NH$_2$.

Another further preferred embodiment is one wherein
A represents

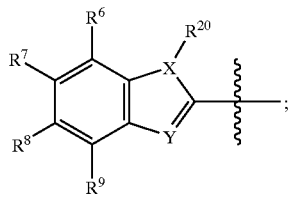

B represents

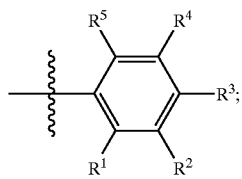

X and Y represent N; and
$R^7$ represents —CONH$_2$, or C(=NH)—NH$_2$.

Another preferred embodiment provides a compound of Formula I wherein $R^1$ represents OH, —COOH, and O—P(O)(OH)$_2$;

$R^2$ and $R^3$ independently represent halogen, H, C$_{1-4}$ alkyl, Ph, toluyl, OH, O—(CH$_2$)$_{1-3}$—C(O)—NH—(CH$_2$)$_{1-2}$—CN, O—(CH$_2$)$_{1-3}$—Ph—p-OCH$_3$, O—CH$_2$—C(O)—NH—(CH$_2$)$_{1-2}$—CH—(CH$_3$)$_2$, O—CH$_2$—C(O)—NH—(CH$_2$)—Ph, O—CH$_2$—C(O)—NH—(CH$_2$)—Ph-pCH$_3$, O—C$_{1-3}$ alkyl, O—(CH$_2$)$_{0-2}$—Ph—R$^{10}$, O—CH$_2$—C(O)—NH—(CH$_2$)$_2$—H, Ph—C$_{1-3}$ alkyl, Ph—N(R$^{10}$)$_2$, O—(CH$_2$)$_{1-3}$-het, O—(CH$_2$)$_{1-3}$—Ph-halo, O—(CH$_2$)$_{1-3}$—NHSO$_2$Ph—R$^{10}$, O—(CH$_2$)$_{1-3}$—NHCO—(CH$_2$)$_{0-2}$—Ph, O—CH$_2$—C(O)—NH—CH$_2$—COO—C(CH$_3$)$_3$, O—(CH$_2$)$_2$—NHC(O)—CH$_2$—NH$_2$, —OPh, O—(CH$_2$)$_{1-3}$—NH-het, O—(CH$_2$)$_2$—NH—C(O)-pyridyl, O—(CH$_2$)$_2$—NH—C(O)—NH-benzyl, O—(CH$_2$)$_2$—cyclohexyl, O—(CH$_2$)$_2$—NH—C(O)—(CH$_2$)$_2$—CONH$_2$, O—(CH$_2$)$_2$—NH—C(O)—CH$_3$—OCH$_3$, thiophene, pyridyl, or O—(CH$_2$)$_2$-pyridyl;

alternatively $R^2$ and $R^3$ taken together form

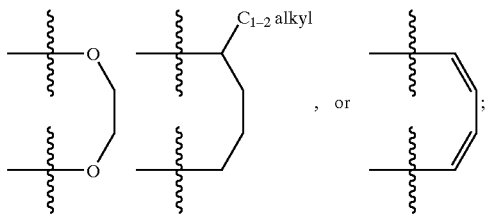

$R^6$ represents halogen, H. NO$_2$, C$_{1-2}$-alkyl, CH=CH—COOCH$_3$, NHSO$_2$C$_{1-2}$ alkyl, NHCO-het, (CH$_2$)$_{1-3}$—COOR$^{10}$, (CH$_2$)$_{1-3}$—CONH—(CH$_2$)$_{1-3}$-pyridyl, or (CH$_2$)$_{1-3}$—CONH—(CH$_2$)$_{1-3}$-dichlorophenyl;

$R^5$ represents H;

$R^6$ represents H;

$R^7$ represents C(=NH)—NH$_2$ or NH(=NH)NH$_2$;

$R^8$ represents H, halogen, OR$^{10}$, CF$_3$, or C(=NH)—NH$_2$;

$R^9$ represents H or halogen; and $R^{20}$ represents H.

Yet another preferred embodiment is one wherein
A represents

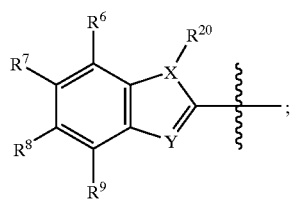

B represents

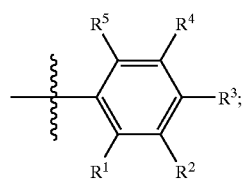

X and Y represent N.

A particularly preferred embodiment provides a compound of Formula I wherein:

$R^1$ represents OH, or COOH;

$R^2$ represents H, halogen, OH, phenyl, O—(CH$_2$)$_{1-3}$—Ph, imidazolyl, 5-amidino benzimidazolyl, O—(CH$_2$)$_{1-2}$—C(O)—NH—C$_{1-6}$ alkyl, or O—CH$_3$—C(O)—NH—CH$_2$—Ph;

$R^3$ represents H, O—CH$_2$—COOH, O—CH$_2$—C(O)O—C$_2$H$_5$, O—CH$_2$—C(O)—NH—(CH$_2$)$_{1-4}$-aryl, O—(CH$_2$)$_{1-4}$—NH—C(O)-naphthyl, CONH$_2$, O—(CH$_2$)$_{1-2}$—C(O)N(R$^{10}$)—(CH$_2$)-$_{1-3}$Ph—R$^{13}$R$^{14}$, O—CH$_2$—C(O)—N(R$^{10}$)—CH$_2$-piperanyl, O—CH$_2$—C(O)—NH—CH$_2$-indoyl, (CH$_2$)$_{1-0}$-aryl,

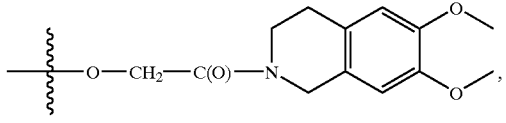

-continued

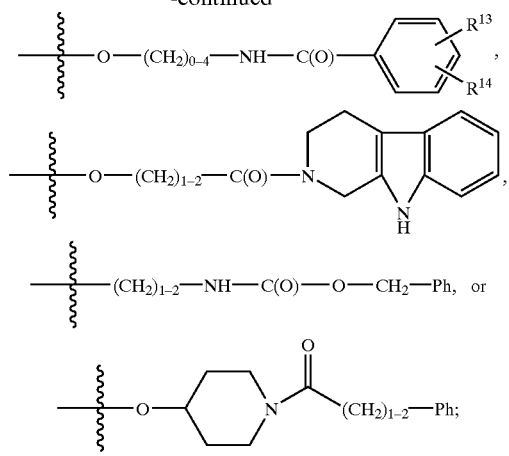

$R^4$ represents H, —$CH_3$, halogen, —$OCH_3$, —$(CH_2)_{1-2}$—$COOR^{10}$, —COOH, —$NO_2$, —OH, aryl,

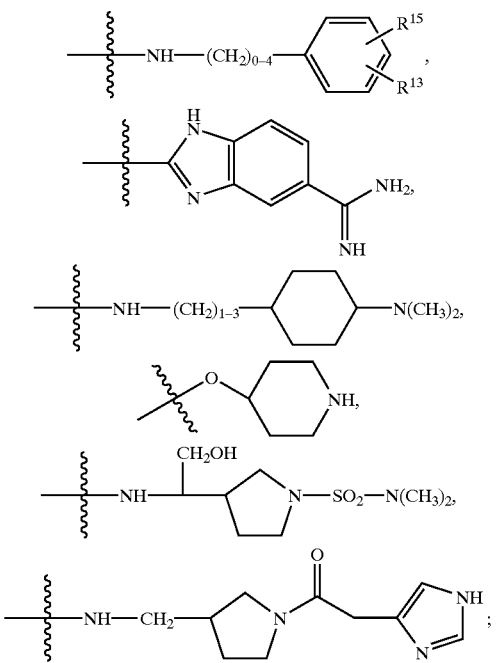

$R^5$ represents H;
$R^6$ represents H;
$R^7$ represents H, halogen, —C(O)—$NH_2$, —C(=NH)—$NH_2$;
$R^8$ represents H, Cl, F, OH or $OCH_3$;
$R^9$ represents H;
$R^{13}$ and $R^{14}$ represents independently at each occurance represents H, halogen, —$OC_{1-2}$ alkyl, —OH, —CF, or —$C_{1-4}$ alkyl; and
$R^{15}$ represents H,

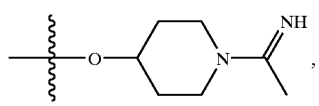

-continued

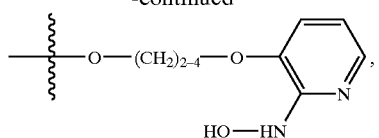

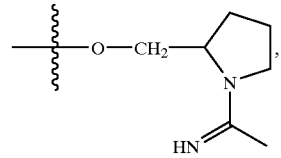

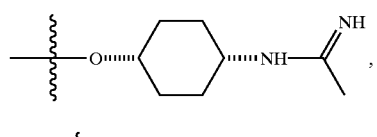

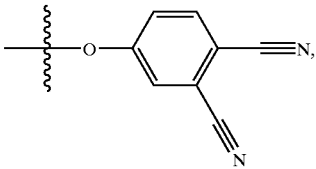

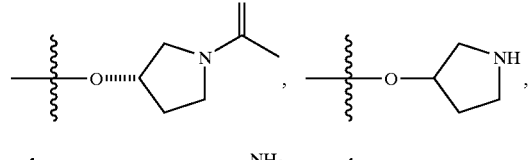

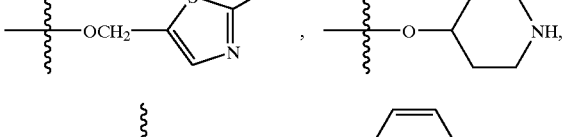

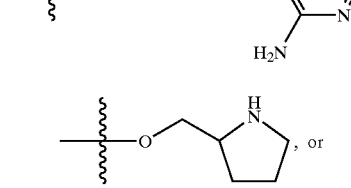

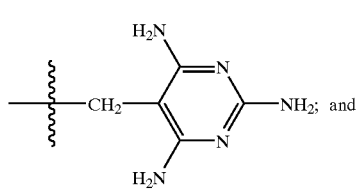

$R^{20}$ represents H or —$CH_2$—Ph.

Provided in another aspect of the present invention is a compound of Formula I wherein A represents

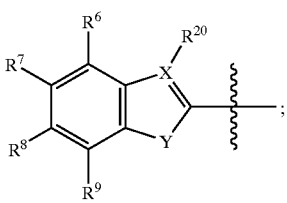

B represents

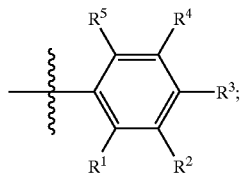

X represents C; and
Y represents NH.

A preferred embodiment of this aspect of the present invention provides compounds wherein $R^1$ represents —OH, —COOH, or P(O)(OH)$_3$;

$R^2$ represents H, halogen, $R^{10}$, -aryl, heteroaryl, —$C_{1-2}$-alkyl, COOH, —O$C_{1-2}$-alkyl, —O—(CH$_2$)$_{0-2}$-aryl, or —$C_{6-10}$ aryl-$C_{1-4}$ alkyl;

$R^3$ represents H or —O—(CH$_2$)$_{1-3}$—COOH;

alternatively $R^2$ and $R^3$ taken together represent

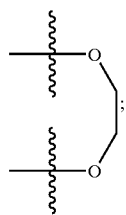

$R^4$ represents H, —$C_{1-4}$ alkyl, —(CH$_2$)$_{1-4}$—COOH, —(CH$_2$)$_{1-4}$—COO$C_{1-2}$-alkyl, halogen, —(CH$_2$)$_{1-2}$—CONH$_2$, —CONH$_2$, —NO$_2$, —O—$C_{1-2}$ alkyl, or —OH;

$R^5$ represents H, —$C_{1-3}$ alkyl, —(CH$_2$)$_{1-4}$—C(O)—NH—(CH$_2$)$_{1-3}$-heteroaryl, —(CH$_2$)$_{1-4}$—C(O)—NH—CH$_3$, or —COOH;

$R^6$ represents H, halogen, or —$C_{1-3}$ alkyl;

$R^7$ represents —C(O)—N$_2$, —C(=NH)—NH—NH$_2$, or amidino;

$R^8$ represents H, or halogen; and $R^{20}$ represents H, —(CH$_2$)$_{1-4}$—Ph—N(SO$_2$—$C_{1-2}$alkyl), —(CH$_2$)$_{1-4}$—NR$^{10}$—C(O)R$^{24}$, —(CH$_2$)$_{1-4}$—NR$^{10}$—SO$_2$—R$^{24}$, —(CH$_2$)$_{1-4}$-het, —(CH$_2$)$_{1-4}$—CON(R$^{10}$)$_2$, —(CH$_2$)$_{1-4}$—N(R$^{10}$)—C(O)—NR$^{10}$R$^{24}$, —(CH$_2$)$_{1-2}$—Ph—NH$_2$, —(CH$_2$)$_{1-3}$—Ph—NO$_2$, —(CH$_2$)$_{1-4}$—N(R$^{10}$)—C(S)—NR$^{10}$R$^{24}$, —$C_{1-2}$-alkyl, —(CH$_2$)$_{1-4}$-optionally substituted aryl, —(CH$_2$)$_{1-4}$-het; —(CH$_2$)$_{1-3}$—N(R$^{10}$)$_2$; —(CH$_2$)$_{1-4}$—CON(R$^{10}$)$_2$, or —(CH$_2$)$_{1-3}$—COOH.

Specifically preferred compounds of the present invention are selected from

3-[3-Bromo-5-(6-carbamimidoyl-1H-benzoimidazol-2-yl)-4-hydroxy-phenyl]-N-phenethyl-propionamide;

3-[4-(6-Carbamimidoyl-1H-benzoimidazol-2-yl)-3-hydroxy-phenyl]-N-(2,3-dichloro-benzyl)-propionamide;

2-[4-(6-Carbamimidoyl-1H-benzoimidazol-2-yl)-3-hydroxy-phenoxy]-N-(2,3-dichloro-benzyl)-acetamide;

3-[3-Bromo-5-(6-carbamimidoyl-1H-benzoimidazol-2-yl)-4-hydroxy-phenyl]-N-[2-(2,4-dichloro-phenyl)-ethyl]-propionamide;

3-[3-Bromo-5-(6-carbamimidoyl-1H-benzoimidazol-2-yl)-4-hydroxy-phenyl]-N-(2-pyridin-2-yl-ethyl)-propionamide;

3-[3-Bromo-5-(6-carbamimidoyl-1H-benzoimidazol-2-yl)-4-hydroxy-phenyl]-N-(3-phenyl-propyl)-propionamide;

2-[4-(6-Carbamimidoyl-1H-benzoimidazol-2-yl)-3-hydroxy-phenoxy]-N-naphthalen-1-ylmethyl-acetamide;

2-(3'-Amino-5-chloro-2-hydroxy-biphenyl-3-yl)-3H-benzoimidazole-5-carboxamidine;

3-[3-Bromo-5-(6-carbamimidoyl-1H-benzoimidazol-2-yl)-4-hydroxy-phenyl]-propionic acid;

2-(3,5-Bis-hydroperoxy-2-hydroxy-phenyl)-3H-benzoimidazole-5-carboxamidine;

2-[4-(5-Carbamimidoyl-1H-benzoimidazol-2-yl)-3-hydroxy-phenoxy]-N-(3-chloro-benzyl)-acetamide;

N-Benzyl-3-[3-bromo-5-(6-carbamimidoyl-1H-benzoimidazol-2-yl)-4-hydroxy-phenyl]-propionamide;

2-(3,5-Dibromo-2,4-dihydroxy-phenyl)-3H-benzoimidazole-5-carboxamidine;

2-(2-Hydroxy-biphenyl-3-yl)-3H-benzoimidazole-5-carboxamidine;

2-(5-Chloro-2-hydroxy-biphenyl-3-yl)-3H-benzoimidazole-5-carboxamidine;

2-(2-Hydroxy-3-phenethyloxy-phenyl)-3H-benzoimidazole-5-carboxamidine;

N-(3-Bromo-benzyl)-2-[4-(5-carbamimidoyl-1H-benzoimidazol-2-yl)-3-hydroxy-phenoxy]-acetamide;

2-{3-[1-(3-Amino-propionyl)-pyrrolidin-2-ylmethoxy]-2-hydroxy-phenyl}-3H-benzoimidazole-5-carboxamidine;

2-(5-Chloro-2-hydroxy-3-pyridin-3-yl-phenyl)-1H-benzoimidazole-5-carboxamidine;

2-[3-(5-Carbamimidoyl-1H-benzoimidazol-2-yl)-2-hydroxy-phenyl]-3,4,6,7-tetrahydro-imidazo[4,5-c]pyridine-5-carboxamidine;

2-[3-(1-Aminoacetyl-pyrrolidin-2-ylmethoxy)-2-hydroxy-phenyl]-3H-benzoimidazole-5-carboxamidine; and 2-(2-Hydroxy-3-phenoxy-phenyl)-3H-benzoimidazole-5-carboxamidine;

2-[2-Hydroxy-3-(1-methyl-1H-benzoimidazol-2-yl)-phenyl]-1H-benzoimidazole-5-carboxamidine;

2-[3-(1-Aminoacetyl-piperidin-3-ylmethoxy)-2-hydroxy-phenyl]-1H-benzoimidazole-5-carboxamidine;

2-{3-[1-(2-Amino-3-methyl-butyryl)-pyrrolidin-2-ylmethoxy]-2-hydroxy-phenyl}-1H-benzoimidazole-5-carboxamidine;

2-[2-Hydroxy-3-(1-hydroxyacetyl-pyrrolidin-2-ylmethoxy)-phenyl]-1H-benzoimidazole-5-carboxamidine;

2-(2-Hydroxy-5-iodo-3-methoxy-phenyl)-1H-benzoimidazole-5-carboxamidine;

2-{3-[1-(2-Amino-3-methyl-butyryl)-pyrrolidin-2-ylmethoxy]-2-hydroxy-phenyl}-3H-benzoimidazole-5-carboxamidine;

2-(2-Hydroxy-5-{4-[1-(1-imino-ethyl)-piperidin-4-yloxy]-benzylamino}-phenyl)-3H-benzoimidazole-5-carboxamidine; compound with methane;

2-(2-Hydroxy-5-{4-[1-(1-imino-ethyl)-piperidin-3-ylmethoxy]-benzylamino}-phenyl)-3H-benzoimidazole-5-carboxamidine;

2-(3-Bromo-2-hydroxy-5-methyl-phenyl)-3H-benzoimidazole-5-carboxamidine;

3-[2,6-Dibromo-4-(6-carbamimidoyl-1H-benzoimidazol-2-yl)-3-hydroxy-phenoxy]-propionic acid;

3-[2,6-Dibromo-4-(6-carbamimidoyl-1H-benzoimidazol-2-yl)-3-hydroxy-phenoxy]-propionic acid ethyl ester; and 2-[3-Bromo-2-hydroxy-5-(3-methoxy-but-3-enyl)-phenyl]-3H-benzoimidazole-5-carboxamidine;

3-Benzyl-2-(3-chloro-2-hydroxy-phenyl)-1H-indole-5-carboxamidine;

3-[3-(3-Benzyl-5-carbamimidoyl-1H-indol-2-yl)-5-bromo-4-hydroxy-phenyl]-propionic acid;

[3-(3-Benzyl-5-carbamimidoyl-1H-indol-2-yl)-5-bromo-4-hydroxy-phenyl]-acetic acid;

6-Chloro-2-(3,5-dichloro-2-hydroxy-phenyl)-1H-indole-5-carboxamidine;

3-Bromo-5-(5-carbamimidoyl-1H-indol-2-yl)-4-hydroxy-benzamide;

2-(3,5-Dichloro-2-hydroxy-phenyl)-1H-indole-5-carboxamidine;
3-(4-Amino-benzyl)-2-(3-bromo-2-hydroxy-5-methyl-phenyl)-1H-indole-5-carboxamidine;
2-(2-Hydroxy-biphenyl-3-yl)-1H-indole-5-carboxamidine;
2-(3-Bromo-2-hydroxy-5-nitro-phenyl)-1H-indole-5-carboxamidine;
2-(5-Hydroxy-2,3-dihydro-benzo[1,4]dioxin-6-yl)-1H-indole-5-carboxamidine;
3-Benzyl-2-(2-hydroxy-phenyl)-1H-indole-5-carboxamidine;
3-Benzyl-2-(3,5-difluoro-2-hydroxy-phenyl)-1H-indole-5-carboxamidine;
3-Benzyl-2-(3,5-dibromo-2-hydroxy-phenyl)-1H-indole-5-carboxamidine;
[3-Bromo-5-(5-carbamimidoyl-1H-indol-2-yl)-4-hydroxy-phenyl]-acetic acid;
3-Benzyl-2-(5-chloro-2-hydroxy-phenyl)-1H-indole-5-carboxamidine;
2-[3-Bromo-5-(5-carbamimidoyl-1H-indol-2-yl)-4-hydroxy-phenyl]-acetamide;
2-(3,5-Difluoro-2-hydroxy-phenyl)-1H-indole-5-carboxamidine;
2-(3,5-Dibromo-2-hydroxy-phenyl)-1H-indole-5-carboxamidine;
2-(2-Hydroxy-5-methyl-biphenyl-3-yl)-1H-indole-5-carboxamidine;
2-(2-Hydroxy-5,4'-dimethyl-biphenyl-3-yl)-1H-indole-5-carboxamidine;
2-(3-Bromo-2-hydroxy-5-methyl-phenyl)-1H-indole-5-carboxamidine;
3-Benzyl-2-(3-bromo-2-hydroxy-5-methyl-phenyl)-1H-indole-5-carboxamidine;
3-Benzyl-2-(3-chloro-2-hydroxy-5-methyl-phenyl)-1H-indole-5-carboxamidine;
3-Benzyl-2-(2-hydroxy-3,5-dimethyl-phenyl)-1H-indole-5-carboxamidine;
2-(3,5-Dibromo-2-hydroxy-phenyl)-3-methyl-1H-indole-5-carboxamidine;
2-(2-Hydroxy-5-methyl-3-thiophen-2-yl-phenyl)-1H-indole-5-carboxamidine;
2-[2-(3-Bromo-2-hydroxy-5-methyl-phenyl)-5-carbamimidoyl-1H-indol-3-yl]-acetamide;
[3-(3-Benzyl-5-carbamimidoyl-1H-indol-2-yl)-5-bromo-4-hydroxy-phenyl]-acetic acid methyl ester;
3-[3-(3-Benzyl-5-carbamimidoyl-1H-indol-2-yl)-5-bromo-4-hydroxy-phenyl]-propionic acid methyl ester;
3-(3-Amino-benzyl)-2-(3-bromo-2-hydroxy-5-methyl-phenyl)-1H-indole-5-carboxamidine;
2-(3-Bromo-2-hydroxy-5-methyl-phenyl)-3-(3-nitro-benzyl)-1H-indole-5-carboxamidine;
3-(3-Amino-benzyl)-2-(2-hydroxy-5-methyl-phenyl)-1H-indole-5-carboxamidine;
3-Benzyl-2-(3-chloro-2-hydroxy-5-methyl-phenyl)-1H-indole-5-carboxamidine;
6-Chloro-2-{5-[2-(1,1-dioxo-1-thiomorpholin-4-yl)-2-oxo-ethyl]-2-hydroxy-biphenyl-3-yl}-1H-indole-5-carboxamidine;
2-[5-(5-Carbamimidoyl-6-chloro-1H-indol-2-yl)-6-hydroxy-biphenyl-3-yl]-N-(2-piperidin-1-yl-ethyl)-acetamide;
6-Chloro-2-{2-hydroxy-5-[2-(2-methoxymethyl-pyrrolidin-1-yl)-2-oxo-ethyl]-biphenyl-3-yl}-1H-indole-5-carboxamidine;
6-Chloro-2-{2-hydroxy-5-[2-oxo-3-(tetrahydro-furan-2-yl)-propyl]-biphenyl-3-yl}-1H-indole-5-carboxamidine;
2-[5-(5-Carbamimidoyl-6-chloro-1H-indol-2-yl)-6-hydroxy-biphenyl-3-yl]-N-(tetrahydro-furan-2-ylmethyl)-acetamide;
2-[5-(5-Carbamimidoyl-6-chloro-1H-indol-2-yl)-6-hydroxy-biphenyl-3-yl]-N-(3-methoxy-propyl)-acetamide;
Morpholine-4-carboxylic acid {2-[5-(5-carbamimidoyl-6-chloro-1H-indol-2-yl)-6-hydroxy-biphenyl-3-yloxy]-ethyl}-aimide;
Phosphoric acid mono-{2-[3-(3-benzyl-5-carbamimidoyl-1H-indol-2-yl)-5-bromo-4-hydroxy-phenyl]-ethyl} ester;
2-[3-(3-Benzyl-5-carbamimidoyl-1H-indol-2-yl)-5-bromo-4-hydroxy-phenyl]-N-{4-[1-(1-imino-ethyl)-piperidin-4-yloxy]-phenyl}-acetamide;
4-[3-(3-Benzyl-5-carbamimidoyl-1H-indol-2-yl)-5-bromo-4-hydroxy-phenyl]-butyric acid;
2-[3-(3-Benzyl-5-carbamimidoyl-1H-indol-2-yl)-5-bromo-4-hydroxy-phenyl]-acetamide;
2-[3-(3-Benzyl-5-carbamimidoyl-1H-indol-2-yl)-5-bromo-4-hydroxy-phenyl]-N,N-dimethyl-acetamide;
[3-(3-Benzyl-5-carbamimidoyl-1H-indol-2-yl)-5-bromo-4-hydroxy-phenyl]-acetic acid;
3-[3-(3-Benzyl-5-carbamimidoyl-1H-indol-2-yl)-5-bromo-4-hydroxy-phenyl]-pentanedioic acid bis-[(2-morpholin-4-yl-ethyl)-amide];
3-[3-(3-Benzyl-5-carbamimidoyl-1H-indol-2-yl)-5-bromo-4-hydroxy-phenyl]-propionamide; and
2-(3-Bromo-2-hydroxy-5-methyl-phenyl)-3-(4-nitro-benzyl)-1H-indole-5-carboxamidine;
or a stereoisomer or pharmaceutically acceptable salt form thereof.
or a stereoisomer or pharmaceutically acceptable salt form thereof.

Yet another aspect of the present invention provides a pharmaceutical composition comprising a pharmaceutically acceptable carrier and a therapeutically effective amount of a compound of Formula I a pharmaceutically acceptable salt thereof.

The present invention also provides a method for treating or preventing a thromboembolic disorder; comprising administering to a patient in need thereof a therapeutically effective amount of a compound of Formula I or a pharmaceutically acceptable salt thereof.

Synthesis

The novel compounds of the present invention can be prepared in a number of ways known to one skilled in the art of organic synthesis. Described herein are some of the preferred synthetic methods for synthesizing novel compounds of the present invention. All temperatures reported herein are in degrees Celsius, unless indicated otherwise.

The novel compounds of Formula I can be prepared using the reactions and synthetic techniques described below. It should be noted that compounds of Formula I include compounds of Formula Ia. These compounds of Formula Ia represent some of the novel compounds of the present invention and can be further transformed to provide other novel compounds of the present invention.

The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the, planning of any synthetic route in this field is the judicious choice of the protecting group used for the protection of the reactive functional groups present in the compounds described in this invention. An authoritative account describing the many alternatives to the trained practitioner is Greene and Wuts (Protective Groups in Organic Synthesis, Wiley and Sons, 1991).

Proton NMR's ($^1$H NMR) were obtained using deuterated solvents such as dimethyl sulfoxide (DMSO-$d_6$), deuterated chloroform (CDCl$_3$), or other appropriate solvents. Schemes I to XXXV illustrate synthesis of precursors useful in the synthesis of compounds of Formula I, or synthesis of compounds of Formula I, having a benzimidazole nucleus, i.e., wherein "A" represents benzimidazole, and Tables 2a and 2b list them. These compounds of Formula I can be represented by the following structural formula:

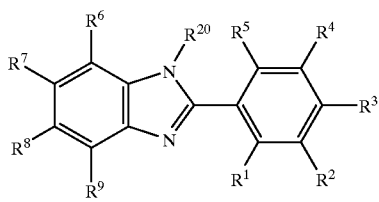

wherein $R^1$, $R^2$, $R^3$, $R^4$, $R^5$, $R^6$, $R^7$, $R^8$ and $R^{20}$ are as defined in the detailed description of the invention.

The aldehydes, represented by structures 3, 5, 8, 10, and 13 and the carboxylic acids represented by structures 44, 43, and 53 and 55 are useful intermediates in the synthesis of the novel compounds of Formulae I and Formula Ia. The aldehydes and carboxylic acids useful in the synthesis of compounds of Formula I either are commercially available or can be prepared by the synthetic schemes outlined below.

Schemes I–IX illustrate the synthesis of aldehydes which can be used to synthesize compounds of Formula I.

Scheme I:

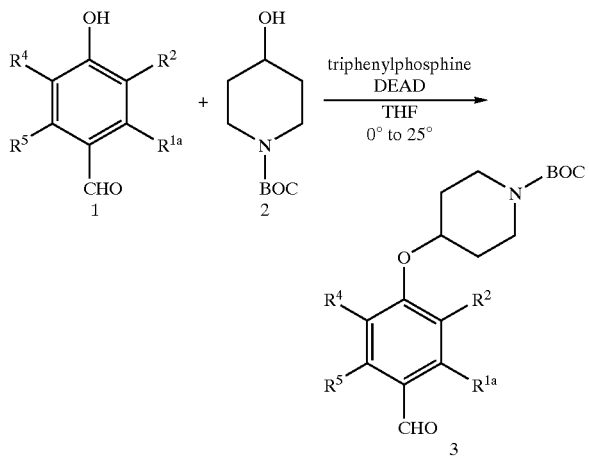

in which $R^{1a}$ is H or $R^1$, and $R^2$, $R^3$, and $R^5$ are as defined in the detailed description.

Scheme I is a representative example of the synthesis of aldehyde 3 using the Mitsunobu reaction. The general procedure comprises mixing an appropriately substituted benzaldehyde, 1, with a Boc protected piperidinol in the presence of triphenyl phosphine in an inert solvent, such as THF, at temperatures ranging from −25° to ambient temperature, preferably 0°. To the cooled mixture is added diethyl azido dicarboxylate (DEAD) in a drop wise manner (about 0.5 to 1 mL per minute). The resulting reaction mixture is stirred at room temperature for 2 to 24 hours after which time the reaction mixture is concentrated under reduced pressure to yield a residue of the desired aldehyde, 3. Purification of the desired aldehyde can be accomplished by using methods such as chromatography, recrystallization or other methods known to one skilled in the art.

Scheme II:

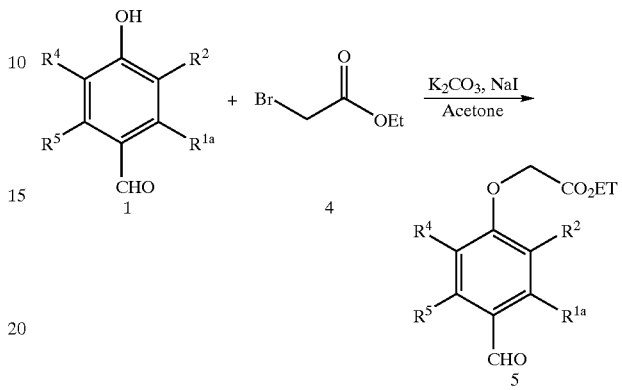

in which $R^{1a}$ is hydrogen or the same as $R^1$.

Scheme II outlines the synthesis of aldehyde 5. The procedure involved forming a reaction mixture by combining an appropriate benzaldehyde 1, such as 4-hydroxy benzaldehyde, ethyl bromoacetate, 4, potassium carbonate and sodium iodide, in an inert solvent, preferably acetone. The reaction mixture is stirred at ambient temperature for 12 to 24 hours after which time the reaction mixture is filtered through celite, and concentrated under reduced pressure to yield an oily residue. This residue can be purified by column chromatography to yield the desired aldehyde, 5.

Scheme III:

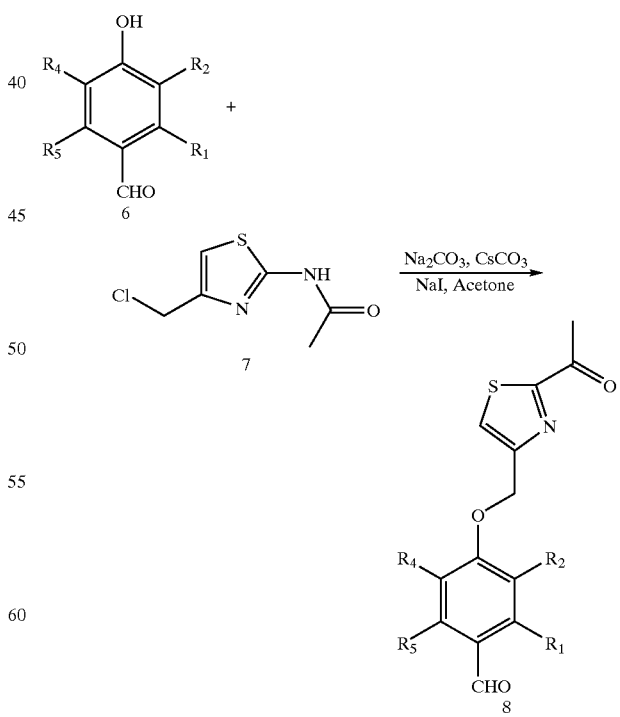

Scheme III represents a general procedure for co preparing aldehydes of formula 8. The procedure comprises mixing 4-hydroxy benzaldehyde 6, substituted is thiazole 7, sodium carbonate, cesium carbonate, and sodium iodide in an inert solvent, such as acetone, to form a reaction mixture which is refluxed for eighteen hours. The reaction mixture is cooled to room temperature, filtered through celite, and the filtrate evaporated to yield a residue. The residue is dissolved in ethyl acetate and washed, in succession, with 2% aqueous sodium hydroxide, water, and brine solution. This washed organic layer is concentrated to yield the desired aldehyde 8.

Scheme IV:

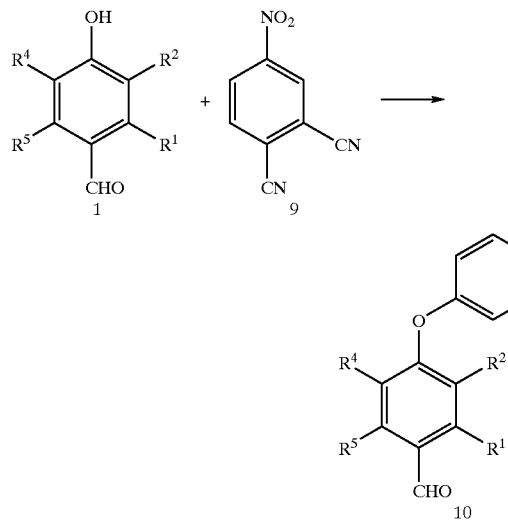

Scheme IV depicts a method of preparing aldehyde, 10. This method comprises reacting a N,N-dimethylformamide (DMF) solution of a hydroxy benzaldehyde, 11, with sodium hydride at about 0° followed by drop wise addition (about 1 mL per minute) of a DMF solution of dicyanonitrobenzene 9. The resulting mixture is stirred from 12 to 24 hours followed by cautious pouring of the reaction mixture in ice water to yield a product. The product is collected by filtration, dried, and purified by recrystallization, e.g., from ethyl acetate, to yield aldehyde 10.

Scheme V depicts a method of preparing aldehyde 13. For example, an aldehyde of formula 11 wherein $R^3$, $R^4$ and $R^5$ are hydrogen, i.e., 2,3-dihydroxybenzaldehyde (0.6 g, 4.3 mmol) was added to dimethyl sulfonamide (DMSO) (10 ml) containing sodium hydride (0.25 g, 10.4 mmol). After one hour a solution of benzyl bromide (0.52 ml, 4.3 mmol) in DMSO (5 ml) is added. Stirring the mixture is continued for 24 h, after which time the mixture is poured into water and extracted with chloroform (2×). The aqueous solution then was acidified with 6N hydrochloric acid to adjust the pH from 2 to about 4 and extracted with chloroform (3×). The latter organic layers were washed with 1N hydrochloric acid and filtered over silica gel to give 3-benzyloxy-2-hydroxy benzaldehyde.

$^1$H NMR (300 MHz, CDCl$_3$) δ: 11.13 (s, 1H), 9.92 (s, 1H), 7.50–6.85 (m, 8H), 5.20 (s, 2H).

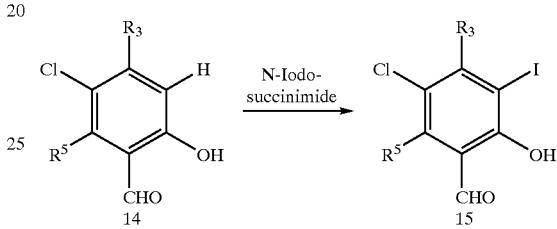

Scheme VI depicts a method for preparing aldehyde 15. For example, a mixture of an aldehyde of formula 14 wherein $R^3$ and $R^5$ are hydrogen, i.e., 5-chloro,2-hydroxy benzaldehyde (0.10 g, 0.64 mmol) and N-iodosuccinimide (0.16 g, 0.71 mmol) in acetic acid (2 mL) was heated to 95° C. for 2 h. Another portion of N-iodosuccinimide (0.020 g, 0.09 mmol) was added and heating was continued for 1 h. The mixture was diluted with ethyl acetate, washed in succession with 5% aqueous Na$_2$S$_2$O$_3$, saturated NaCl, and dried (Na$_2$SO$_4$). The solvent was removed under reduced pressure, and 5-chloro-3-iodo-benzaldehyde was obtained as a yellow crystalline solid (0.17 g, 94%)

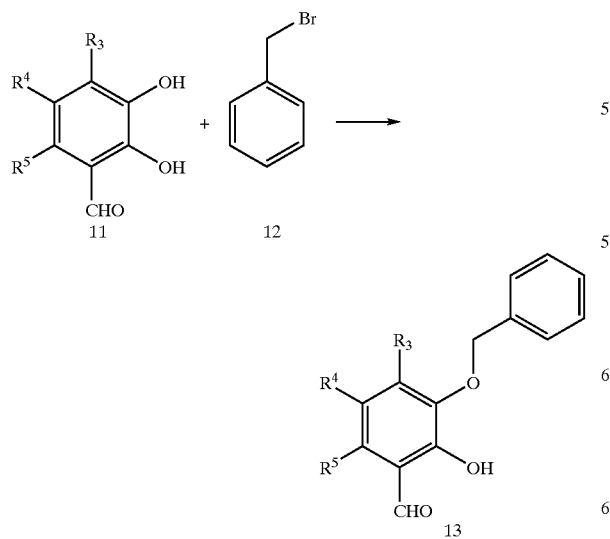

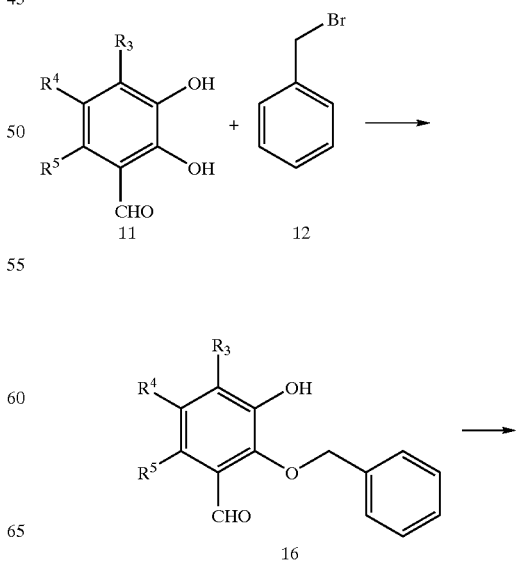

Scheme IX

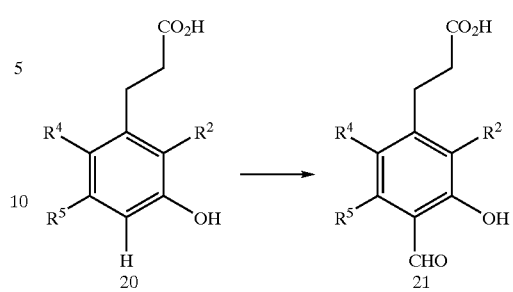

Scheme IX illustrates the preparation of aldehydes 21. For example, a compound of formula 20 wherein $R^3$, $R^4$ and $R^5$ are hydrogen, i.e., 3-(3-hydroxyphenyl)propionic acid, (3.0 g, 0.018 mol, Aldrich Chemical Comp, Cat 1279), NaOH (6 g, 0.15 mol), water (40 mL), and chloroform (40 ml) were combined and heated at 70° C. for 12 h in a 100 ml round bottom flask. The solution is acidified to pH 4, extracted with EtOAc (2×30 mL), dried (MgSO$_4$), filtered, and concentrated under reduced pressure to give 3-(4-formyl-3-hydroxy phenyl)propionic acid which was used without further purification.

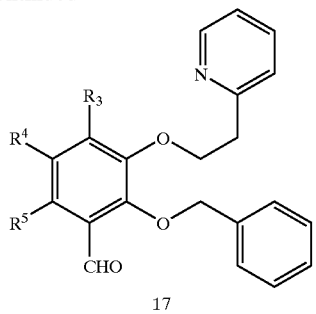

Scheme VII illustrates the synthesis of benzyl protected aldehydes 17.

For example, sodium hydride (0.52 g, 21.7 mmol) is added to DMSO (20 ml) followed by an aldehyde of formula 11 wherein $R^3$, $R^4$ and $R^5$ are hydrogen, i.e., 2,3-dihydroxybenzaldehyde, (2.8 g, 20.2 mmol). After stirring the solution for 1 h at ambient temperature, benzyl bromide 12 (2.4 ml, 20.2 mmol) was added forming a red-brown reaction mixture which was further stirred 12 h at ambient temperature. The solution was then partitioned between ethyl acetate (200 ml) and 0.5 N hydrochloric acid (300 ml). The organic layer was separated and MgSO4, filtered and concentrated to afford a brown oil. The brown oil is purified by flash chromatography (15% ethyl acetate/hexane) to give 3.21 g of 2-benzyloxy-3-hydroxy-benzaldehyde 16.

2-benzyloxy-3-hydroxy-benzaldehyde 16 (0.30 g, 1.3 mmol), triphenylphosphine (0.41 g, 1.6 mmol) and 2-(2-hydroxyethyl)pyridine (0.18 ml, 1.6 mmol) were stirred in THF (15 ml), followed by the addition of DEAD (0.25 ml, 1.6 mmol). After stirring for 12 h, the reaction mixture is partitioned between ethyl acetate (200 ml) and saturated aqueous sodium hydrogen carbonate (200 ml). The organic layer is separated, dried (MgSO$_4$), filtered and concentrated to give a brown oil. The brown oil is purified by flash chromatography (50% ethyl acetate/hexanes) to afford 0.29 g (66%) of 2-hydroxy-3-(2-pyridin-2-ylethoxy)benzaldehyde 17 as a light yellow solid.

Scheme VIII

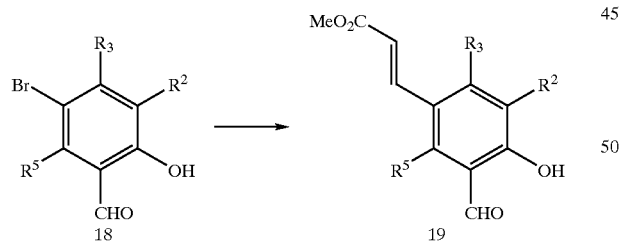

Scheme VIII outlines the Heck coupling (R. F. Heck, "Palladium Catalyzed Reactions of Organic Halides with Olefins," Accounts Chem. Res. 12, 146 (1979)) used to prepare aldehydes 19. The bromo-benzaldehyde 18 is typically combined with the methyl acrylate (1.5 eq.), triphenyl phosphine (0.33 eq.), palladium acetate (0.15 eq.) and triethylamine (2 eq.) in benzene and the mixture refluxed for 12–18 h. After cooling the mixture is diluted with 0.05N HCl and extracted with ethyl acetate. The organic extracts are washed with water, then brine and dried (MgSO$_4$). Filtration followed by purification over silica gel affords the desired aldehyde 19.

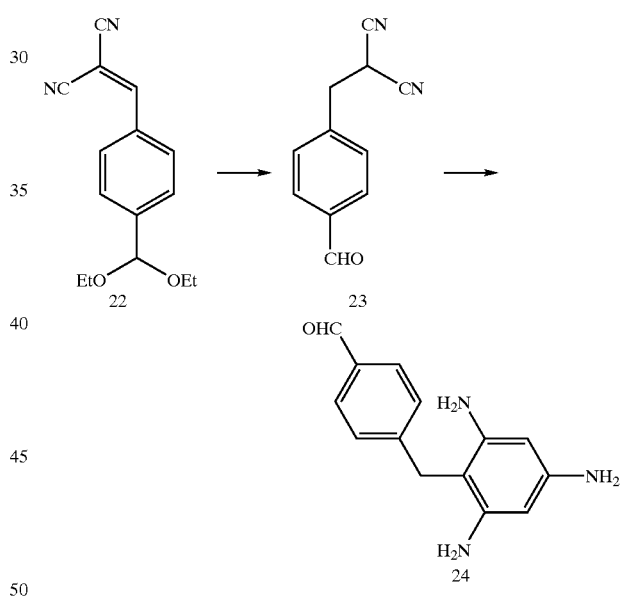

Compound 22 was prepared by combining terephthaldehyde monodiethylacetal (Acros Chemical Comp. Cat #24069-1000, 5.0 g, 0.02 mol), malononitrile (1.32 g, 0.02 mol), EtOH (30 mL), and NaOEt (2.72 g, 0.04 mol). The mixture was stirred at ambient temperature for 12 h, water (50 mL) was added, and the mixture was extracted with Et$_2$O (2×50 mL). The organic layer was dried (MgSO$_4$), filtered and concentrated under reduced pressure to give 22 in a 88% yield (4.5 g, 0.017 mol).

$^1$HNMR (300 MHz, DMSO) δ: 7.95 (d, 2H), 7.75 (s, 1H), 7.65 (d, 2H), 7.26 (d, 1H), 5.51 (s, 1H), 3.6 (t, 2H), 1.21 (t, 3H).

MS (CI) Calc for $C_{15}H_{16}N_2O_2$: 256.12, Found: M+ 257.1.

In a 100 mL round bottom flask 22 (4.5 g, 0.017 mol) and EtOH (50 mL) were combined and the mixture cooled to 0° C. NaBH$_4$ (1 g) was added in increments and the mixture was stirred at 0° C. for 30 min. 1N HCl (50 mL) was added, the mixture was extracted with Et$_2$O (2×50 mL), dried (MgSO$_4$), filtered and concentrated under reduced pressure to give 4.4 g, 99% of 23. $^1$HNMR (300 MHz, DMSO) δ 10.05 (s, 1H), 7.96 (d, 2H), 7.58 (d, 2H), 7.35 (s, 1H), 3.45 (d, 1H).

In a 100 mL round bottom flask under an atmosphere of nitrogen was placed 50 mL of EtOH. Sodium (0.28 g, 0.012 mol) was added slowly and the mixture was stirred at 0° C. for 30 minutes. Guanidine hydrochloride (1.16 g, 0.012 mol) was added, the mixture was stirred at ambient temperature for an additional 30 minutes and 23 (2.0 g, 0.011) was added in one portion. The mixture was refluxed for 4 h, cooled to ambient temperature, and concentrated under reduced pressure, and the residue was triturated with Et$_2$O forming a precipitate. The precipitate was isolated and dried under vacuum for 12–18 h to give 24 in a 47% yield (1.2 g, 0.005 mol).

$^1$HNMR (300 MHz, DMSO) δ: 9.98 (s, 1H), 7.80 (d, 2H), 7.37 (d, 2H), 7.24 (s, 1H), 7.18 (br s, 6H).

The following Schemes X–XIII illustrate the 15 synthesis of carboxylic acids which can be used to synthesize compounds of Formula I Scheme X:

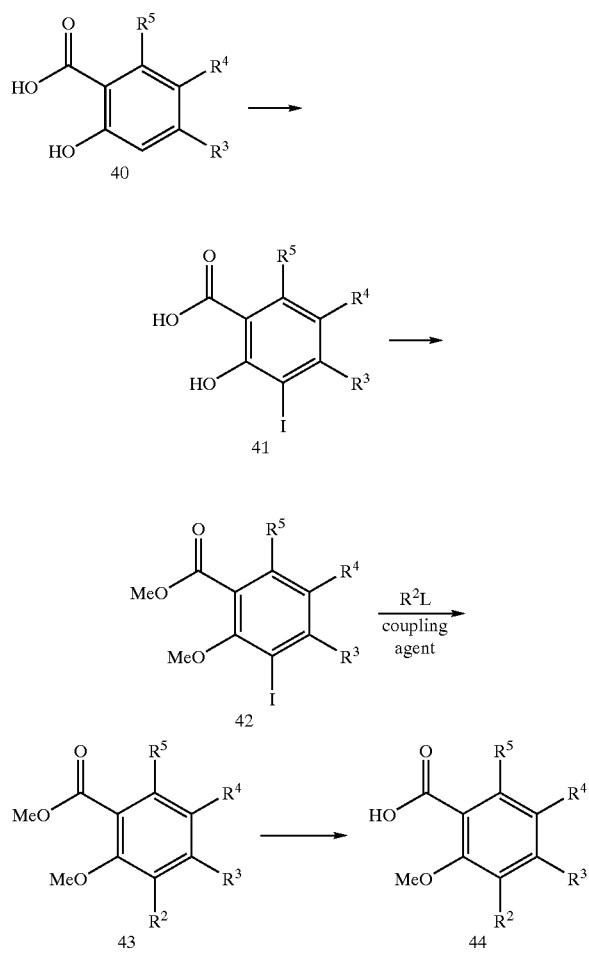

N-iodosuccinimide (7.17 g, 32 mmol) in acetic acid (30 mL) was heated to 95° C. for 2 h. Additional N-iodosuccinimide (0.70 g, 3.1 mmol) was added and heating was continued for 1 h. The mixture was cooled and poured over ice. The precipitate was isolated by filtration and the crude material was purified by recrystallization from methanol/water. The solid was isolated by filtration, rinsed with water and dried. 5-Chloro-2-hydroxy-3-iodo-benzoic acid 41 was obtained as a tan crystalline solid (6.14 g, 71% yield).

$^1$H-NMR (DMSO-d$_6$) δ ppm: 12.0 (brs), 8.1 (s, 2H), 7.8 (s, 1H).

A solution of 5-Chloro-2-hydroxy-3-iodo-benzoic acid 41 in DMF (40 mL) was treated with K$_2$CO$_3$ (5.70 g, 41 mmol) and then stirred for 15 min. The mixture was chilled to 0° C. under nitrogen and iodomethane (2.82 mL, 45 mmol) was added. This heterogeneous mixture was stirred for 18 h at 20° C. Additional K$_2$CO$_3$ (0.57 g, 4.1 mmol) and iodomethane (0.28 mL, 4.5 mmol) were added. After 6 h, the mixture was diluted with ether, washed with saturated NaHCO$_3$, NaCl, and dried (Na$_2$SO$_4$). The solvent was removed under reduced pressure to give 5-Chloro-3-iodo-2-methoxybenzoic acid methyl ester 42 as a light purple crystalline solid (6.21 g, 93% yield).

$^1$H-NMR (DMSO-d$_6$) δ ppm: 8.15 (s, 1H), 7.75 (s, 1H), 3.85 (s, 3H), 3.75 (s, 3H).

To a solution of methyl,5-chloro-3-iodo-2-methoxybenzoic acid methyl ester (0.80 g, 2.5 mmol) and tetrakis (triphenylphosphine)palladium(0) (0.085 g, 0.074 mmol) in toluene (12 mL) was added 3-nitrobenzene-boronic acid (0.45 g, 2.7 mmol) dissolved in 1 mL of ethanol. Aqueous 2 N K$_2$CO$_3$ (2.7 mL, 5.4 mmol) was added and the mixture was heated to reflux for 18 h. The mixture was diluted with ether, washed with 3:1 saturated NaHCO$_3$/conc. ammonium hydroxide, 0.1 M EDTA, saturated NaCl, and dried (Na$_2$SO$_4$). The solvent was removed under reduced pressure, and the crude material was purified by silica gel chromatography employing a gradient elution of 60 to 75% CH$_2$Cl$_2$/hexane. 5-Chloro-2-methoxy-3'-nitro-biphenyl-3-carboxylic acid methyl ester 43 was obtained as an amber waxy solid (0.59 g, 75% yield).

$^1$H-NMR (DMSO-d$_6$) δ ppm: 8.4 (s, 1H), 8.3 (d, 1H), 8.1 (d, 1H), 7.7 (m, 3H), 3.8 (s, 3H), 3.4 (s, 3H).

5-Chloro-2-methoxy-3'-nitro-biphenyl-3-carboxylic acid methyl ester 43 (0.59 g, 1.8 mmol) is dissolved in THF (1.8 mL) and treated with a solution of 2 N methanolic KOH (1.8 mL, 3.7 mmol). After 16 h, the solvent is removed under reduced pressure, followed by dilution with 5 mL of 1 M HCl and 10 mL of ice cold water. The resulting precipitate is isolated by filtration, rinsed with water and dried yielding 5-Chloro-2-methoxy-3'-nitro-biphenyl-3-carboxylic acid 44

$^1$H-NMR (DMSO-d$_6$) δ ppm: 8.37 (s, 1H), 8.28 (d, 1H, J=8.0 Hz), 8.02 (d, 1H, J=7.6 Hz), 7.75 (m, 3H), 3.45 (s, 3H).

Scheme XI:

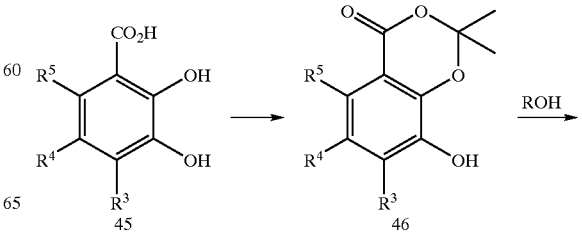

Scheme X shows a representative example of the synthesis of carboxylic acid 44.

For example, a mixture of a compound of formula 40 wherein R$^3$ and R$^4$ are hydrogen and R$^5$ is chloro, i.e., 5-chloro-2-hydroxy benzoic acid, (5.0 g, 29 mmol) and

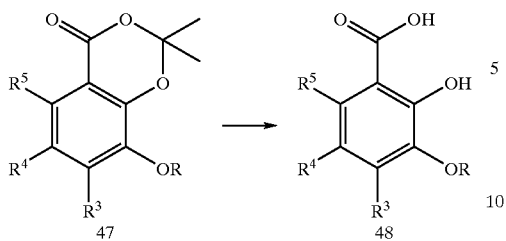

Scheme XI shows a method incorporating a Mitsonobu reaction for the synthesis of carboxylic acid 48.

For example a compound of formula 46 wherein $R^3$, $R^4$ and $R^5$ are hydrogen, i.e., 8-hydroxy-2,2-dimethylbenzo-[1,3]dioxin-4-one, was prepared by the procedure of Danishefsky, S. J.; and Dushin, R. G. *J. Am. Chem. Soc.* 1992, 114, 655–659.

$^1$H NMR (300 MHz, CDCl$_3$) δ: 7.82 (d, 1H), 7.20 (d, 1H), 7.05 (t, 1H), 5.49 (s, 1H), 1.78 (s, 6H).

A solution of 8-hydroxy-2,2-dimethylbenzo-[1,3]dioxin-4-one 46 (1.34 g, 6.88 mmol) and 3-hydroxymethyl-pyrrolidine-1-carboxylic acid tert-butyl ester (1.27 g, 6.85 mmol) in THF (35 mL) under $N_2$ was cooled to 0° C. Triphenylphosphine (1.80 g, 6.86 mmol) was added to the solution followed by addition of diethylazodicarboxylate (1.1 mL, 6.9 mmol) over 5 min. After 30 min, the reaction mixture was warmed to room temperature and stirred for 6 h. Partial evaporation gave a concentrated crude material which was directly loaded onto a flash chromatography column (non-linear gradient 0–20–35% EtOAc in hexanes) to give 1.62 g (65%) of tert-butyl 2-(2,2-dimethyl-4-oxo-4,4-benzo[1,3]dioxin-8-yloxymethyl)pyrrolidine-1-carboxylate 47 as an oil.

$^1$H NMR (300 MHz, DMSO-d$_6$) δ: 7.47 (m, 2H), 7.12 (t, 1H), 5.02 (br s, 1H), 3.7–3.2 (br m), 2.09 (br m, 2H), 1.70 (s, 6H), 1.40 (d, 9H).

tert-butyl-2-(2, 2-dimethyl-4-oxo-4,4-benzo[1,3]dioxin-8-yloxymethyl)pyrrolidine-1-carboxylate 47 (1.65 g, 4.54 mmol) was dissolved in DMSO (9.5 mL) and then 49% aqueous KOH (1.5 mL) was added to the solution to form a basic reaction mixture. This basic reaction mixture was heated at 60° C. for 40 min. After cooling to room temperature and addition of 0.5 M aqueous KHSO$_4$ (100 mL) gave an acidic suspension. The suspension was extracted with ether (4×250 mL) and the combined extracts were washed with brine (2×50 mL) and dried (Na$_2$SO$_4$). Evaporation of the ether gave 1.26 g (93%) of 3-(1-tert-butoxycarbonyl pyrrolidin-2-ylmethoxy)-2-hydroxy benzoic acid 48 as a brown solid.

$^1$H NMR (300 MHz, DMSO-d$_6$) δ: 7.41 (d, 1H), 7.25 (d, 2H), 6.81 (t, 1H), 4.95 (br s, 1H), 3.6–3.2 (br m), 2.05 (br m, 2H), 1.40 (s, 9H).

Scheme XII:

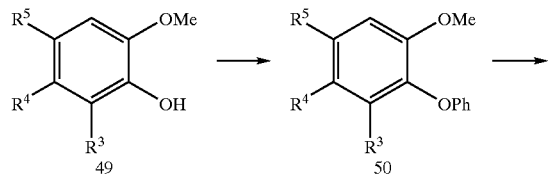

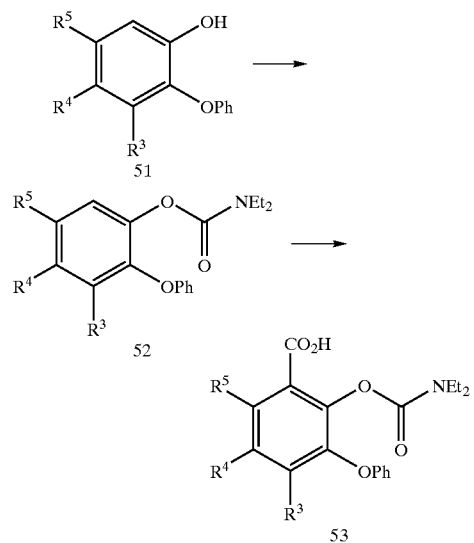

Scheme XII illustrates a method for the synthesis of carboxylic acid 53.

For example a compound of formula 50 wherein $R^3$, $R^4$ and $R^5$ are hydrogen, i.e., 1-methoxy-2-phenoxy benzene, was made according to the procedure in Organic Syntheses Collective Volume 3, p 566–568.

MS (chemical ionization) m/z calcd for [M+1] 201.08, found 201.

$^1$H NMR (300 MHz DMSO-d$_6$) δ: 7.30 (t, 2H), 7.21 (m, 2H), 7.00 (m, 3H), 6.78 (d, 2H), 3.72 (s, 3H).

1-methoxy-2-phenoxy benzene 50 (0.99 g, 4.9 mmol) was dissolved in CH$_2$Cl$_2$ under a N$_2$ atmosphere and cooled to 0° C. A 1.0 M solution of boron tribromide in CH$_2$Cl$_2$ (7.0 mL, 7.0 mmol) was added over 5 min. The resulting reaction mixture was stirred at 0° C. for 1 h and then co-evaporated with CH$_3$OH (4×30 mL) to give 0.95 g of 2-phenoxyphenyl 51.

MS (chemical ionization) m/z calcd for [M+1] 187.07, found 187.

$^1$H NMR (300 MHz, CDCl$_3$) δ: 7.40 (t, 2H), 7.35–6.95 (m, 5H), 6.90 (m, 2H).

2-Phenoxy phenyl 51 (0.95 g, 5.1 mmol) was dissolved in pyridine under a N$_2$ atmosphere. Diethyl carbamyl chloride (0.65 mL, 5.1 mmol) was added to solution over 5 min after which the solution is heated at reflux for 5 h. The pyridine is removed by rotary evaporation and the crude product dissolved in ether. The ether solution was washed with 0.5 M aqueous KHSO$_4$ followed by brine, and dried (Na$_2$SO$_4$) to give 0.60 g of crude 2-phenoxyphenyl diethyl carbonate 52. Flash chromatography (10% EtOAc in hexanes) further purified the product.

MS (chemical ionization) m/z calcd for [M+1] 286.14, found 286.

$^1$H NMR (300 MHz, DMSO-d6) δ: 7.25 (m, 5H), 7.09 (m, 2H), 6.80 (m, 2H), 3.5–3.0 (m), 0.9 (p, 6H).

2-phenoxyphenyl diethyl carbonate 52 (0.264 g, 0.926 mmol) was dissolved in anhydrous THF under a N$_2$ atmosphere using oven dried glassware. The solution was cooled to −78° C. with a dry ice/acetone bath. A 1.7 M solution of tert-butyl lithium in pentane (0.62 mL, 1.0 mmol) was added over 4 min. After 40 min at −78° C., the atmosphere was changed to CO$_2$ using a balloon and kept at −78° C. for 4 hr. The reaction vessel was warmed to 0° C. followed by quenching with 10% aqueous NH₄Cl. The product was extracted with ether (3×50 mL), washed with brine (2×20 mL), and dried (Na₂SO₄). Rotary evaporation of ether gave 0.293 g of 2-diethyl carbamoyloxy-3-phenoxy benzoic acid 53.

MS (bioion) m/z calcd for [M+1] 330.13, found 329.3.

¹H NMR (300 MHz, DMSO-d6) δ: 7.59 (m, 1H), 7.20 (m, 4H), 6.98 (t, 1H), 6.81 (d, 2H), 3.08 (m, 4H), 0.8 (p, 6H).

Scheme XIII:

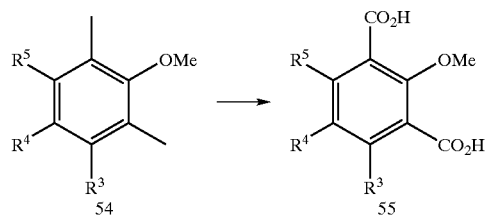

Scheme XIII illustrates the synthesis of a diacid used to make compounds of carboxylic acid 55.

For example to a 500 mL round bottom flask charged with 170 mL of water and compound of formula 54, wherein R³, R⁴ and R⁵ are hydrogen, i.e., 2-methoxy-1,3-dimethylbenzene, (5 g, 36.7 mmol) was added KMnO₄ (12.2 g, 77.2 mmol). The solution was heated to a gentle reflux using an oil bath until the purple color had disappeared (2 hour). Another batch of KMnO₄ (12.2 g, 77.2 mmol) was added and the heating was continued until the purple color was destroyed (2–2.5 hour). The reaction mixture was cooled slightly and the precipitated oxides of manganese were filtered through Celite. After washing the precipitates with warm water (2×50 mL), the filtrate was concentrated under reduced pressure to about ⅓ its original volume. This concentrated filtrate was acidified to pH 2.5 and the resulting fine white precipitate was filtered and dried overnight under reduced pressure on a high vacuum pump, yielding 2-methoxy isophthalic acid 55 as a white powder (6.8 g, 94% yield).

¹H-NMR (300 MHz, DMSO-d₆) δ: 7.97 (d, 2H), 6.9 (t, 1H), 2.5 (s, 3H).

The following schemes (XX to XXI) generally can be used to prepare compounds of Formula I having a benzimidazole nucleus.

Scheme XX

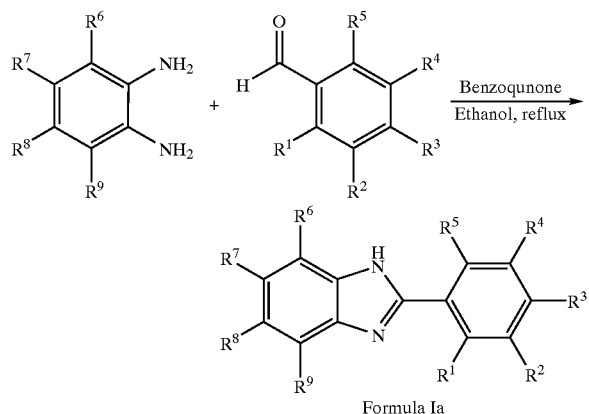

Scheme XX outlines general procedures (Method A) for the synthesis of compounds of Formula Ia. Scheme XX requires refluxing a mixture of diaminobenzamidine monohydrochloride with an aldehyde in the presence of an oxidizing agent (e.g., benzoquinone, sodium metabisulfite, and the like) in ethanol for about 12 hours. The mixture is then cooled to room temperature and poured into acetonitrile. This results in the generation of the desired product of Formula Ia which is further washed with fresh acetonitrile and dried.

Scheme XXI

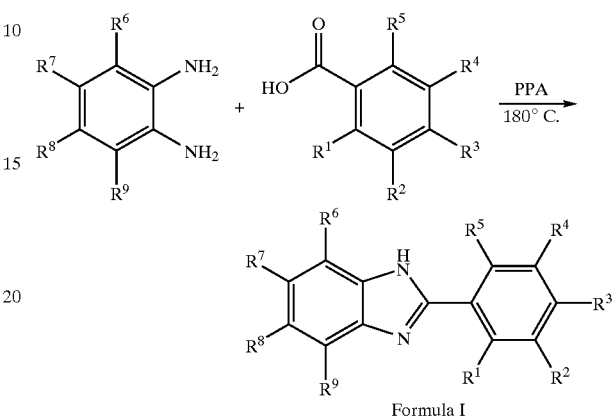

Formula I

The above Scheme XXI (Method B) can also be used to make compounds of Formula Ia. An appropriate carboxylic acid, is heated at 180° C. with the hydrochloride salt of diamino benzene derivative in poly phosphoric acid (PPA) under a nitrogen atmosphere (until the carboxylic acid had reacted completely). This reaction mixture is cooled to room temperature and diluted with water (or dilute HCl) to yield a suspension. The suspension is isolated, and washed with cold water and dried to yield a compound of Formula Ia in the above scheme.

If Scheme XX or XXI utilizes appropriately protected acids or aldehydes, the final products depicted in Table 2 were realized by standard deprotection techniques known to one skilled in the art of organic synthesis (See Greene, 'Protecting groups in Organic Synthesis'). Thus, for example, BOC groups were removed using HCl or TFA. In the case of an aldehyde, which has a benzyl protecting group at R², after the Method A reaction of this aldehyde with 3,4-diaminobenzamidine, the crude dark purple solid is isolated and then subjected to hydrogenation conditions in ethanol with Pd (10% on activated carbon). After 2 h, the Pd is filtered and the filtrate is concentrated to ~20 ml and added to ether with vigorous stirring. After filtering and drying the product is isolated, represented by Example 172 in Table 2.

A variation of the above scheme XXI is used to make Examples 100 and 200 shown below:

TABLE 2

Example 100

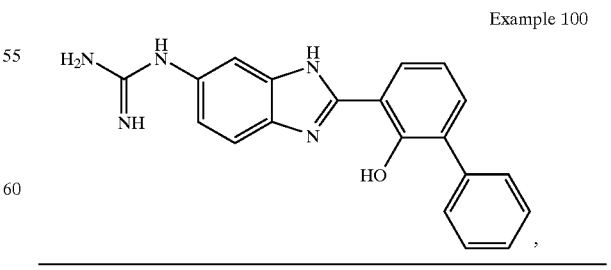

The procedure is the same as Scheme XXI, except that 4-guanidino,1,2-diaminobenzene is used instead of 3,4-diaminobenzamidine.

Example 200 uses the acid from Scheme XIII which is reacted with 3,4,-diaminopyridine in the presence of polyphosphoric acid (Method B, Scheme XXI). The resultant compound is then reduced and appropriately substituted to yield Example 200.

Example 200

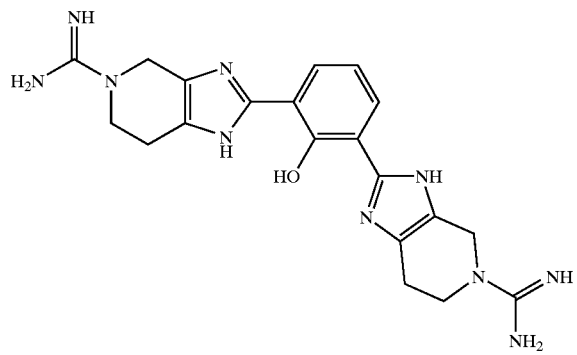

Table 2 lists examples of compounds of Formula I (and Ia) prepared by the above synthetic schemes XX and XXI, methods A and B respectively.

Compounds of Formula I wherein $R^7$ is an amidino group (C(=NH)NH$_2$) can also be prepared by treating compounds of Formula I wherein $R_7$=CN with NH$_2$OH followed by Zn in acetic acid.

Table 2: Lists some of the benzimidazole compounds represented by Formula I.

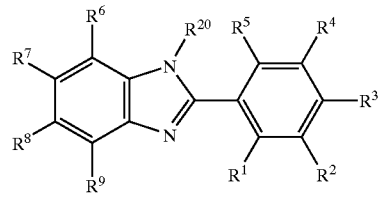

in $R^6$, $R^8$, $R^9$ and $R^{20}$ represent hydrogen; and $R^7$ represents amidino (or guanidino in the case of Example 100).

| Ex. No. | $R^1$ | $R^2$ | $R^3$ | $R^4$ | $R^5$ |
|---|---|---|---|---|---|
| 100 | OH | Ph | H | H | H |
| 101 | OH | I | H | Cl | H |
| 102 | OH | CO$_2$H | H | H | H |
| 103 | OH | OCH$_2$Ph | H | H | H |
| 104 | OH | OCH$_2$CO$_2$H | H | H | H |
| 105 | OH | OH | H | H | H |
| 106 | OH | F | H | H | H |
| 107 | OH | OEt | H | H | H |
| 108 | OH | I | H | I | H |
| 109 | OH | Cl | H | Cl | H |
| 110 | OH | Ph | H | H | H |
| 111 | OH | Ph | H | Cl | H |
| 112 | OH | 3-yl-pyridyl | H | Cl | H |
| 113 | OH | o-tolyl | H | Cl | H |
| 114 | OH | p-tolyl | H | Cl | H |
| 115 | OH | H | H | Cl | H |
| 116 | OH | OPh | H | H | H |
| 117 | OH | Pyrrolidin-2-ylmethoxy | H | H | H |
| 118 | OH | 2-amino ethoxy | H | H | H |
| 119 | OH | 1-H-Imidazo[4,5-c]pyridin-2-yl | H | H | H |
| 120 | OH | 4-1H-Benzoimidazol-2-yl | H | H | H |
| 121 | OH | 1-Methyl-1H-benzoimidazol-2-yl | H | H | H |
| 122 | OH | Benzothiazol-2-yl | H | H | H |
| 123 | OH | 4-Hydroxy-1H-benzoimidazol-2-yl | H | H | H |
| 124 | OH | 1H-Imidazo[4,5-c]pyridin-2-yl | H | H | H |
| 125 | OH | 5-Fluoro-1H-benzoimidazol-2-yl | H | H | H |

-continued

| Ex. No. | R¹ | R² | R³ | R⁴ | R⁵ |
|---|---|---|---|---|---|
| 126 | OH | 5-Carbamimidoyl-1H-benzoimidazol-2-yl | H | H | H |
| 127 | OH | 5-Methyl-1H-benzoimidazol-2-yl | H | H | H |
| 128 | OH | H | H | CH=CHCO₂Me | H |
| 129 | OH | H | Me | H | H |
| 130 | OH | 2-Pyridin-2-yl-ethoxy | H | H | H |
| 131 | OH | H | H | nitro | H |
| 132 | OH | H | OCH₂CO₂Et | H | H |
| 133 | OH | m-nitrophenyl | H | Cl | H |
| 134 | OH | —CH₂CH₂CH₂CH(CH₃)— | | H | H |
| 135 | OPO₃H | —CH₂CH₂CH₂CH(CH₃)— | | H | H |
| 136 | OPO₃H | —CH₂CH₂CH₂CH(CH₃)— | | H | H |
| 137 | OH | Br | H | Me | H |
| 138 | OH | I | H | Me | H |
| 139 | OH | Pyrrolidin-3-yloxy | H | H | H |
| 140 | OH | Pyrrolidin-2-ylmethoxy | H | H | H |
| 141 | OH | H | OH | H | H |
| 142 | OH | H | 3-tert-Butoxycarbonylaminopropoxy | H | H |
| 143 | OH | H | 4-oxy-piperidine-1-carboxylic acid tert-butyl ester | H | H |
| 144 | OH | H | 2-Benzyloxycarbonylaminoethoxy | H | H |
| 145 | OH | H | H | OMe | H |
| 146 | OH | OH | OH | H | H |
| 147 | OH | OCH₃ | H | I | H |
| 148 | OH | NO₃ | H | NO₃ | H |
| 150 | OH | H | CH₂CH₂—COOH | H | H |
| 151 | OH | OMe | H | H | H |
| 152 | OH | OMe | H | NO₂ | H |
| 153 | OH | OMe | OMe | H | Me |
| 154 | OH | H | H | OCF₃ | H |
| 155 | OH | H | OH | H | OH |
| 156 | OH | H | H | OH | H |
| 157 | OH | H | CH₂COOH | H | H |
| 158 | OH | H | OH | OH | H |
| 159 | OP(O)(OH)₂ | Me | H | H | H |
| 160 | OH | Piperidin-3-ylmethoxy | H | H | H |
| 161 | OH | Piperidin-3-ylethoxy | H | H | H |

-continued

| Ex. No. | R¹ | R² | R³ | R⁴ | R⁵ |
|---|---|---|---|---|---|
| 162 | OH | 2-(3,5-Dichloro-phenyl)-ethoxy | H | H | H |
| 163 | OH | 4-Methoxy-benzyloxy | H | H | H |
| 164 | OH | 2-Cyclohexyl-ethoxy | H | H | H |
| 165 | OH | 2-(4-Methoxy-phenyl)-ethoxy | H | H | H |
| 166 | OH | 2-(3-Chloro-phenyl)-ethoxy | H | H | H |
| 167 | OH | 2-(4-Chloro-phenyl)-ethoxy | H | H | H |
| 168 | OH | 2-(4-Fluoro-phenyl)-ethoxy | H | H | H |
| 169 | OH | 3-Nitro-benzyloxy | H | H | H |
| 170 | OH | H | H | H | OH |
| 171 | OH | 4-Fluoro-benzyloxy | H | H | H |
| 172 | OH | 2-(1,3-Dioxo-1,3-dihydro-isoindol-2-yl)-ethoxy | H | H | H |
| 173 | OH | phenethyloxy | H | H | H |
| 174 | OH | Br | H | CH₂COOH | H |
| 175 | OH | Cl | H | CH₂COOH | H |
| 176² | OH | Cl | H | CH₂COOCH₃ | H |
| 177² | OH | Cl | H | CH₂COOH | H |
| 178 | OH | 3-nitrophenyl | H | CH₂CH₂COOCH₃ | H |
| 179 | OH | 3-nitrophenyl | H | CH₂CH₂COOH | H |
| 180 | OH | Cl | H | CH₂COOH | H |
| 181¹ | OH | 3-acetylamino-phenyl | H | CH₂CH₂COOH | H |
| 182 | OH | 3-chloro-4-fluorophenyl | H | CH₂CH₂COOH | H |
| 183 | OH | 2-thienyl | H | CH₂CH₂COOH | H |
| 184 | Br | Br | H | 2-tert-butoxycarbonyl-amino-2-carboxy-ethyl | H |
| 185 | OH | Br | H | 2-amino-2-carboxy-ethyl | H |
| 186 | OH | phenyl | H | 2-carboxyethyl | H |
| 187 | OH | Br | H | 2-tert-Butoxycarbonyl-amino-3-oxo-5-phenyl-pentyl | H |
| 188 | OH | Br | H | 2-Amino-2-phenethylcarb-amoyl-ethyl | H |
| 189³ | OH | Br | H | CH₂CH₂COOH | H |
| 190 | OH | Cl | H | CH₂CH₂COOH | H |
| 191² | OH | Cl | H | CH₂CH₂COOH | H |
| 192¹ | OH | Cl | H | CH₂COOCH₃ | H |
| 193 | OH | 5-[2-(1,3-dioxo-1,3-dihydro-isoindol-2-yl)-1-imino-ethyl]-4,5,6,7-tetrahydro-3H-imidazo[4,5-c]pyridin-2-yl | H | H | H |

| Ex. No. | R¹ | R² | R³ | R⁴ | R⁵ |
|---|---|---|---|---|---|
| 194 | OH | 4-dimethylamino-phenyl)-ethoxy | H | H | H |
| 195 | OH | OCH₃ | H | H | (CH₂)₃—NH₃ |
| 196 | OH | 3-methoxy-pheny-1-yl | H | methyl | H |
| 197 | OH | phenyl | H | methyl | H |
| 198 | OH | 1,4-Dihydro-benzo[d][1,2]dioxin-6-yl | H | methyl | H |
| 199 | OH | 4-methoxy-pheny-1-yl | H | methyl | H |
| 200 | OH | 2-methoxy-phen-1-yl | H | methyl | H |
| 201 | OH | NO₂ | H | H | H |
| 202 | OH | O-cyclopentyl | H | H | H |
| 203 | OH | O-CH₂-Ch(CH₃)₂ | H | H | H |
| 204 | OH | Br | H | H | H |
| 205 | OH | | | | |
| 206 | OH | O-ethyl | H | Br | H |
| 207 | OH | Br | H | CH₂COOH | H |
| 208 | OH | 3-acetylamino-phen-1-yl | H | Cl | H |
| 209 | OH | NH-CO-ethyl | H | H | H |
| 210 | OH | 2-oxo-pyrrolidin-1-yl | H | H | H |
| 211 | OH | 3-(2-Amino-acetylamino)-phen-1-yl | H | Cl | H |
| 212 | OH | 3-(3-amino-propionylamino)-phen-1-yl | H | Cl | H |
| 213 | OH | Cl | H | CH₂COOH | H |
| 214 | OH | Br | H | 3-{2-[(benzo(1,3]dioxol-5-ylmethyl)-carbamoyl]-ethyl}-phen-1-yl | H |
| 215 | OH | Br | H | 3-[2-(2-Morpholin-4-yl-ethylcarbamoyl)--ethyl]-phen-1-yl | H |
| 216 | OH | Br | H | 3-{2-[(Pyridin-3-ylmethyl)-carbamoyl]-ethyl}-phen-1-yl | H |
| 217 | OH | Br | H | CH₂CO—NH—CH₂—Ph | H |
| 218 | OH | Br | H | CH₂CO—NH—CH₂—CH₂—Ph | H |

[1] R⁷ represents C(=O)NH₂ and R⁸ represents F
[2] R⁸ represents F
[3] R⁸ represents Cl Listed below is the proton NMR ($^1$H NMR) and Mass spectral data for compounds listed in Table 2.

Ex. 100

$^1$H-NMR (DMSO-d$_6$) δ ppm: 9.92 (s, 1H), 8.14 (d, 1H, J=7.7 Hz), 7.72 (d, 1H, J=7.7 Hz), 7.65–7.60 (m, 2H), 7.56 (s, 1H), 7.48–7.32 (m, 7H), 7.22–7.08 (m, 2H).

MS (ES) calc. 343.1, found 343.9.

Ex. 101

$^1$H-NMR (DMSO-d$_6$) δ ppm: 9.41 (s, 2H), 9.09 (s, 2H), 8.38 (s, 1H), 8.23 (s, 1H), 7.98 (s, 1H), 7.88 (d, 1H, J=8.3 Hz), 7.75 (d, 1H, J=8.5 Hz).

MS (ESI, M$^+$+1): Calc. 412.0; Found 412.8.

Ex. 102

$^1$H NMR (DMSO-d$_6$) δ: 9.35 (s, 2H), 8.95 (s, 2H), 8.40 (d, 1H), 8.2 (s, 1H), 7.98 (d, 1H), 7.99 (t, 1H), 7.85 (d, 1H) 7.68 (d, 1H), 7.24 (d, 1H, J=7.4 Hz), 6.98 (t, 1H, J=8.0 Hz), 5.22 (s, 2H).

MS(ESI, M+1): 296.3 (calc.); 297.0 (obs.).

Ex. 103

$^1$H NMR (DMSO-d$_6$) δ: 9.42 (br.s, 2H), 9.09 (br.s, 2H), 8.22 (s, 1H), 7.88 (d, 1H, J=8.5 Hz), 7.80–7.75 (m, 2H0, 7.49 (d, 2H, J=7.1 Hz), 7.42–7.33 (m, 3H), 7.24 (d, 1H, J=7.4 Hz), 6.98 (t, 1H, J=8.0 Hz), 5.22 (s, 2H).

MS: 358.14 (calc.); 358.8 (obs.).

Ex. 105

$^1$H-NMR (DMSO-d$_6$) δ ppm: 9.35 (s, 2H), 9.00 (s, 2H), 8.19 (s, 1H), 7.85 (d, 1H), 7.70 (d, 1H), 7.59 (d, 1H), 6.95 (d, 1H), 6.85 (t, 1H).

MS (CI, M$^+$+1): Calc. 268.1; Found: 268.7.

Ex. 107

$^1$H NMR (DMSO-d$_6$) δ: 9.27 (br.s, 2H), 8.96 (br.s, 2H), 8.15 (s, 1H), 7.81 (d, 1H, J=8.7 Hz), 7.68 (d, 1H, J=10.5 Hz), 7.64 (d, 1H, J=9.3 Hz), 7.09 (d, 1H), 6.94 (1H, t, J=7.8 Hz), 4.06 (q, 2H, 6.9 Hz), 1.33 (t, 3H, J=6.9 Hz).

MS: 296.13 (calc.); 296.9 (obs.).

Ex. 108

$^1$H NMR (DMSO-d$_6$) δ: 9.34 (br.s, 2H), 9.17 (br.s, 2H), 8.45 (s, 1H), 8.15 (m, 2H), 7.86 (d, 1H, J=8.4 Hz), 7.73 (d, 1H, J=8.7 Hz).

MS: 503.89 (calc.); 504.5 (obs.).

Ex. 110

2-(2-Hydroxy-biphenyl-3-yl)-3H-benzoimidazole-5-carboxamidine $^1$H-NMR (DMSO-d$_6$) δ ppm: 9.39 (s, 2H), 9.08 (s, 2H), 8.28–8.13 (m, 2H), 7.85 (d, 1H, J=8.1 Hz), 7.74 (d, 1H, J=8.3 Hz), 7.65–7.56 (m, 2H), 7.52–7.31 (m, 4H), 7.13 (t, 1H, J=76 Hz).

MS (ESI, M$^+$+1): Calc. 328.1; Found 328.9.

Ex. 111

2-(5-Chloro-2-hydroxy-biphenyl-3-yl)-3H-benzoimidazole-5-carboxamidine $^1$H-NMR (DMSO-d$_6$) δ ppm: 9.39 (br s, 2H), 9.05 (br s, 2H), 8.33 (s, 1H), 8.23 (br s, 1H), 7.90–7.30 (m, 8H).

MS (ES(, M+1): Calc. 362.1, Found: 362.9.

Ex. 112

MS (Bioion): Calc. 363.09; Found 364.0.

Ex. 113

$^1$H-NMR (DMSO-d$_6$) δ ppm: 9.39 (s, 2H), 9.06 (s, 2H), 8.36 (s, 1H), 8.21 (s, 1H), 7.87 (d, 1H, J=8.12 Hz), 7.75 (d, 1H, J=8.2 Hz), 7.75–7.15 (m, 5H), 2.15 (s, 3H).

MS (ESI, M+1) Calc. 376.1, Found 377.0.

Ex. 114

$^1$H-NMR (DMSO-d$_6$) δ: 14.25 (br s, 1H), 13.70 (br s, 1H), 9.39 (s, 2H), 9.05 (s, 2H), 8.30 (br s, 2H), 7.90–7.70 (m, 2H), 7.55–7.45 (m, 3H), 7.26 (d, 2H, J=7.9 Hz), 2.35 (s, 3H).

MS (ES) calc. 376.1, found 377.0.

Ex. 115

$^1$H-NMR (DMSO-d$_6$) δ ppm: 9.46 (s, 2H), 9.16 (s, 2H), 8.36 (d, 1H, J=2.4 Hz), 8.24 (s, 1H), 7.92 (d, 1H, J=8.5 Hz), 7.78 (d, 1H, J=8.5 Hz), 7.51 (dd, 1H, J=8.8, 2.4 Hz), 7.20 (d, 1H, 8.9 Hz).

MS (CI) calc. 286.7, found 287.2.

Ex. 116

2-(2-Hydroxy-3-phenoxy-phenyl)-3H-benzoimidazole-5-carboxamidine $^1$H NMR (DMSO-d$_6$) δ: 9.40 (s, 2H), 9.05 (s, 2H), 8.20 (s, 1H), 8.07 (d, 1H, J=10.5 Hz), 7.86 (d, 1H, J=9 Hz), 7.74 (d, 1H, J=9 Hz), 7.33 (t, 2H, J=9 Hz), 7.23 (d, 1H, J=9 Hz), 7.1–7.03 (m, 2H), 6.94 (d, 2H, J=7.5 Hz).

Mass ESI (M+1): 344.13 (calc.); 346.2 (obs.).

Ex. 117

$^1$H NMR (DMSO-d$_6$) δ: 9.98 (s, 2H), 9.22 (s, 2H), 8.27 (s, 1H), 7.92 (t, 2H, J=6 Hz), 7.82 (d, 1H, J=12 Hz), 7.29 (d, 1H, J=9 Hz), 7.05 (t, 1H, J=9 Hz), 4.38 (d, J=12 Hz), 4.26 (t, J=12 Hz), 4.1–3.4 (br.m), 3.4–3.1 (br.m), 2.25–1.60 (br.m, 5H).

MS (ESI): Calc.: 351.17; Obs.: 351.19.

Ex. 118

$^1$H NMR (DMSO-d$_6$) δ: 9.49 (s, 2H), 9.18 (s, 2H), 8.39 (s, 2H), 8.25 (s, 1H), 7.96–7.89 (m, 2H), 7.79 (d, 1H, J=9 Hz), 7.04 (t, 1H, J=15 Hz), 4.25 (t, 2H), 4.0–3.0 (br.m).

MS: 311.14 (calc.); 311.19 (obs.).

Ex. 119

2-[3-(1H-benzoimidazol-2-yl)-2-hydroxy-phenyl]-1H-benzoimidazole-5-carboxamidine $^1$H NMR (d$_6$-DMSO) δ: 9.55 (s, 2H), 9.2 (s, 2H), 8.7 (d, 1H), 8.55 (d, 1H), 8.3 (s, 1H), 7.98 (d, 1H), 7.95 (t, 1H), 7.85 (t, 1H), 7.8 (d, 1H), 7.58 (d, 1H), 7.55 (d, 1H), 7.4 (t, 1H).

Mass ESI (M$^+$+1): Calculated: 368.14; Obs.: 369.0.

Ex. 120

$^1$H NMR (d$_6$-DMSO) δ 9.5 (s, 2H), 9.45 (s, 1H), 9.1 (d, 2H), 8.6 (d, 1H), 8.57 (5, 1H), 8.55 (d, 1H), 8.3 (s, 1H), 8.2 (d, 1H), 7.9 (d, 1H), 7.8 (d, 1H), 7.4 (t, 1H).

MS: 369.13 (calc.); 370.0 (obs).

Ex. 121

¹H NMR (d₆-DMSO) δ: 8.35 (d, 1H); 8.15 (s, 1H); 8.07 (d, 1H); 8.05 (d, 1H); 8.0 (t, 1H); 7.97 (t, 1H); 7.95 (d, 1H); 7.9 (d, 1H); 7.83 (d, 1H); 7.28 (t, 2H); 4.0 (s, 3H).

Mass ESI (M$^+$+1): Calculated: 382.15; Obs.: 383.0.

Ex. 122

¹H NMR (d₆-DMSO) δ: 9.45 (s, 2H), 9.22 (s, 2H), 8.55 (d, 1H), 8.45 (d, 1H), 8.28 (s, 1H), 8.19 (d, 1H), 8.09 (d, 1H), 7.93 (d, 1H), 7.79 (d, 1H), 7.6 (t, 1H), 7.55 (t, 1H), 7.45 (t, 1H).

MS: 385.10 (calc.); 385.9 (obs.).

Ex. 123

¹H NMR (DMSO-d₆) δ: 9.4 (s, 2H), 9.05 (s, 2H), 8.22 (s, 1H), 8.2 (d, 1H), 7.80 (d, 1H), 7.78 (d, 1H), 7.38 (t, 1H), 7.20 (t, 1H), 7.05 (d, 1H), 6.75 (d, 1H).

MS (Bioion): Calc.: 384.4; Obs.: 384.

Ex. 124

¹H NMR (d₆-DMSO) δ: 9.4 (s, 2H), 9.05 (s, 2H), 8.55 (d, 1H), 8.52 (d, 1H), 8.49 (d, 1H), 8.4 (d, 1H), 8.25 (s, 1H), 7.95 (d, 1H), 7.75 (d, 1H), 7.50 (t, 1H), 7.3 (t, 1H).

MS: 369.13 (calc.); 370 (obs.).

Ex. 125

MS: 386.13 (calc.); 387.0 (obs.).

Ex. 126

¹H NMR (d₆-DMSO) δ: 9.5 (s, 4H), 9.2 (s, 4H), 8.57 (d, 2H), 8.3 (s, 2H), 7.95 (d, 2H), 7.29 (d, 2H), 7.4 (t, 1H), 7.29 (d, 2H).

MS: 410.16 (calc.); 411.0 (obs.).

Ex. 127

MS: 382.15 (calc.); 383.0 (obs.).

Ex. 129

MS: 266.12 (calc.); 266.8 (obs.).

Ex. 130

¹H NMR (DMSO-d₆) δ: 9.50 (br.s, 2H), 9.22 (br.s, 2H), 8.87 (d, 1H, J=5.8 Hz), 8.58 (d, 1H, J=7.9 Hz), 8.24 (s, 1H), 8.16 (d, 1H, J=8.0 Hz), 7.99–7.86 (m, 3H), 7.78 (d, 1H, J=7.4 Hz), 4.51 (t, 2H, J=5.8 Hz), 3.61 (t, 2H, J=5.8H).

MS: 373.15 (calc.); 374.0 (obs.).

Ex. 131

¹H NMR (DSMO-d₆), 300 MHz) δ: 9.45 (s, 2H), 9.20 (s, 2H), 9.16 (d, 1H, J=2.69 Hz), 8.22 (in, 2H), 7.86 (d, 1H, J=8.52 Hz), 7.75 (d, 1H, J=8.52 Hz), 7.27 (d, 1H, J=9.17 Hz).

MS: 298.3 (M$^+$1).

Ex. 132

¹HMR (DMSO-d₆) δ: 9.44 (br. s, 2H), 9.06 (br. s, 2H), 8.18 (br. s, 2H), 7.86 (d, 1H, J=8.5 Hz), 7.75 (d, 1H, J=8.5 Hz), 6.68–6.74 (m, 2H), 4.89 (s, 2H), 4.18 (Q, 2H, J=7.1 Hz), 1.22 (t, 3H, J=7.1 Hz).

MS: Calc.: 354.13;:354.9 (obs.).

Ex. 133

¹H NMR (d₆-DMSO) δ: 9.42 (br s, 2H), 9.08 (br s, 2H), 8.53 (s, 1H), 8.44 (d, 1H), 8.30–8.05 (m, 3H), 7.95–7.75 (m, MS: 407.1 (calc.); 407.9 (obs.).

Ex. 135

¹H-NMR (DMSO-d₆) δ ppm: 9.47 (s, 2H), 9.13 (s, 2H), 8.22 (s, 1H), 7.93 (s, 1H), 7.90 (d, 1H, J=8.9 Hz), 7.80 (d, 1H, J=8.9 Hz), 3.30–3.05 (m, 2H), 2.78 (m, 1H), 1.78 (m, 4H), 1.23 (d, 3H, J=7.5 Hz).

MS (CI, M+1): 434.1 (calc.); 435.4 (obs.).

Ex. 136

¹H NMR (DMSO-d₆) δ ppm: 9.40 (s, 2H), 9.05 (s, 2H), 8.20 (s, 1H), 7.85 (s, 1H), 7.80 (d, 1H, J=9.5 Hz), 7.70 (d, 1H, J=9.5 Hz), 3.18–3.05 (m, 1H), 2.92–2.70 (m, 2H), 1.95 (m, 1H), 1.79–1.20 (m, 5H), 1.00 (t, 3H, J=7.9 Hz).

MS (CI, M+1): 448.1 (calc.); 449.5 (obs.).

Ex. 137

¹H NMR (DMSO-d₆) δ: 9.38 (s, 2H), 9.0 (s, 2H), 8.2 (br. s, 1H), 8.03 (s, 1H), 7.86 (br. s, 1H), 7.72 (d, 1h, J=7.78 Hz), 7.60 (s, 1H), 2.35 (s, 3H).

MS: 345.1 (obs.).

Ex. 138

¹H NMR (DMSO-d₆) δ: 9.4 (s, 2H), 9.05 (s, 2H), 8.2 (br. s, 1H), 8.03 (br. s, 1H), 7.85 (br. s, 1H), 7.8–7.65 (m, 2H), 2.3 (s, 3H).

MS: 392.0 (calc) 392.8 (obs.)

Ex. 139

¹H NMR (DMSO-d₆) δ: 9.67 (br.m, 1H), 9.47 (s, 2H), 9.15 (s, 2H), 8.22 (s, 1H), 7.94–7.88 (m, 2H), 7.79 (d, 1H, J=6 Hz), 7.30 (d, 1H, J=9 Hz), 7.04 (t, 1H,), 5.45 (s, 1H), 3.50–3.25 (m, 4H), 2.15 (br.s, 2H).

MS (ES): Calc.: 337.15; Obs.: 337.7.

Ex. 140

¹H-NMR (DMSO-d₆) δ ppm: 9.45 (s, 2H), 9.20 (s, 2H), 8.90 (d, 1H), 8.23 (s, 1H), 8.12 (t, 1H), 7.90 (t, 2H), 7.79 (d, 1H), 7.30 (d, 1H), 7.05 (t, 1H), 4.40 (d, 1H), 4.21 (t, 1H), 4.05–3.50 (m), 3.40–3.20 (m, 2H), 3.05 (q, 1H), 2.25–1.75 (m, 5H).

MS (ESI): 351.17 (calc.), 352.0 (obs.).

Ex. 144

¹H NMR (300 MHz, DMSO-d₆) δ: 9.51 (s, 2H), 9.18 (s, 2H), 8.22 (br.m, 2H), 7.91 (d, 1H, J=8.44 Hz), 7.80 (d, 1H, J=8.44 Hz), 7.59 (br.t, 1H), 7.36 (br.s, 5H), 6.70 (br.m, 2H), 5.13 (s, 2H), 4.08 (s, 2H), 3.3–3.7 (br.m).

MS: 446.5 (M+1).

Ex. 145

¹H-NMR (DMSO-d₆) δ ppm: 9.49 (s, 2H), 9.18 (s, 2H), 8.24 (s, 1H), 7.97–7.90 (m, 2H), 7.79 (d, 1H), 7.12 (s, 2H).

MS (ES) calc. 282.1, found 282.9.

Ex. 146

Mass, ESI: (M$^+$+1): 284.3 (calc.); 284.9 (obs.).

Ex. 147

Mass, ESI: (M$^+$+1): 408.2 (calc.); 408.8 (obs.).

Ex. 148

¹H NMR (DMSO-d₆) δ: 9.25 (s, 2H), 9.10 (s, 1H), 8.70 (s, 2H), 9.63 (s, 1H), 8.10 (s, 1H), 7.80 (d, 1H), 7.60 (d, 1H).

Mass, ESI: (M⁺+1): 342.3 (calc.); 342.9 (obs.).

Ex. 149

Mass, ESI: (M⁺+1): 347.4 (calc.); 348.0 (obs.).

Ex. 150

¹H NMR (DMSO-d₆) δ 9.54 (s, 2H), 9.27 (s, 2H), 8.28 (s, 1H), 8.26 (d, 1H, J=9.7 Hz), 8.00 (d, 1H, J=9.0 Hz), 7.89 (d, 1H, J=9 Hz), 7.11 (s, 1H), 6.98 (d, 1H, J=9.6 Hz), 5.0–4.0 (br s, 1H) 2.86 (t, 2H, J=6.0 Hz), 2.59 (t, 2H, J=6.0 Hz).

Mass, MS (CI): 324.12 (calc.); 324.9. (obs.).

Ex. 151

2-(2-Hydroxy-3-methoxyphenyl)-3H-benzoimidazole-5-carboxamidine

Mass, ESI: (M⁺+1): 282.3 (calc.); 282.9 (obs.).

Ex. 152

2-(2-Hydroxy-3-methoxy-5-nitrophenyl)-3H-benzoimidazole-5-carboxamidine

Mass, ESI: (M⁺+1): 327.3 (calc.); 327.9 (obs.).

Ex. 153

2-(3,4-Dimethoxy-2-hydroxy-6-methylphenyl)-3H-benzoimidazole-5-carboxamidin

Mass, ESI: (M⁺+1): 326.4 (calc.); 326.9 (obs.).

Ex. 154

2-(2-Hydroxy-5-trifluoromethoxyphenyl)-3H-benzoimidazole-5-carboxamidine

Mass, ESI: (M⁺+1): 336.3 (calc.); 336.9 (obs.).

Ex. 155

2-(2,4,6-Trihydroxyphenyl)-3H-benzoimidazole-5-carboxamidine

Mass, ESI: (M⁺+1): 284.3 (calc.); 284.8 (obs.).

Ex. 157

¹HNMR (DMSO-d₆) δ: 9.48 (s, 2H), 9.18 (s, 2H), 8.24 (s, 1H), 8.23 (d, 1H, J=10.0 Hz), 7.95 (d, 1H, J=8.1 Hz), 7.82 (d, 1H, J=8.1 Hz), 7.10 (s, 1H), 6.98 (d, 1H, J=9.6 Hz), 6.55 (s, 1H), 5.0–4.0 (br s, 1H, CO2H), 3.65 (s, 2H.

Mass, MS (CI) 310.11 (calc.); 310.9. (obs.).

Ex. 158

2-(2,4,5-Trihydroxyphenyl)-3H-benzoimidazole-5-carboxamidine

Mass, ESI: (M⁺+H): 284.3 (calc.); 284.8 (obs.).

Ex. 159

¹H NMR (DMSO-d₆) δ ppm: 9.37 (s, 1H), 9.11 (s, 1H), 8.18 (s, 1H), 7.86 (d, 1H, J=7.6 Hz), 7.81 (d, 1H, J=8.6 Hz), 7.71 (d, 1H, J=8.3 Hz), 7.46 (d, 1H, J=7.3 Hz), 7.24 (t, 1H, J=7.6 Hz), 2.41 (s, 3H).

MS (ESI, M+1H): 346.1 (calc.); 346.9 (obs.).

Ex. 160

¹H-NMR (DMSO-D₆) δ: ppm: 9.50 (s, 2H), 9.21 (s, 2H), 9.00 (t, 1H), 8.23 (s, 1H), 8.0–7.7 (m, 3H), 7.22 (d, 2H, J=8 Hz), 7.02 (t, 1H, 8 Hz), 4.5–3.0 (br.m), 2.8 (m, 2H), 3.38 (br.s, 1H), 2.05–1.60 (m, 4H), 1.4 (m, 1H).

MS (ESI): 365.19 (calc.); 365.9 (obs.).

Ex. 161

¹H-NMR (DMSO-d₆) δ: ppm: 9.48 (s, 1H), 9.30–9.00 (m, 3H), 8.25 (s, 1H), 7.9 (m, 2H), 7.30 (d, 1H, J=8 Hz), 7.23 (d, 1H, J=8 Hz), 7.02 (t, 1H, J=8 Hz), 5.0–3.5 (br.m), 3.3 (br.m), 2.85 (m, 1H), 2.30–2.10 (m, 1H), 2.10–1.85 (m, 2H), 1.85–1.30 (m, 6H).

MS (ESI): 379.20 (calc.); 379.8 (obs.).

Ex. 162

¹H-NMR (DMSO-d₆) δ: 9.44 (s, 2H), 9.14 (s, 2H), 8.22 (s, 1H), 7.89–7.74 (m, 3H), 7.61 (d, 1H, J=2.2 Hz), 7.55 (d, 1H, J=8.3 Hz), 7.40 (dd, 1H, J=8.3, 2.2 Hz), 7.21 (d, 1H, 7.8 Hz), 6.98 (t, 1H, J=7.8 Hz), 4.27 (t, 2H, J=6.8 Hz), 3.20 (t, 2H, J=6.8 Hz).

MS (ESI, M⁺+1): Calc. 440.08; Found 441.0.

Ex. 163

¹H NMR (DMSO-d₆) δ: 9.42 (s, 2H), 9.10 (s, 2H), 8.22 (s, 1H), 7.87 (d, 1H, J=8.5 Hz), 7.77 (m, 2H), 7.42 (d, 2H, J=8.5 Hz), 7.24 (d, 1H, J=8.0 Hz), 6.96 (m, 3H), 5.13 (s, 2H), 3.74 (s, 3H).

MS (ESI, M⁺+1): Calc. 388.15; Found 389.0.

Ex. 164

¹H NMR (DMSO-d₆) δ: 9.44 (s, 2H), 9.14 (s, 2H), 8.22 (s, 1H), 7.88 (d, 1H, J=8.5 Hz), 7.76 (m, 2H), 7.17 (d, 1H, J=7.7 Hz), 6.98 (t, 1H, J=7.7 Hz), 4.07 (t, 2H, J=6.7 Hz), 1.76–1.62 (m, 8H), 1.16 (m, 3H), 0.94 (m, 2H).

MS (ESI, M⁺+1): Calc. 378.21; Found 379.1.

Ex. 165

¹H NMR (DMSO-d₆) δ: 9.45 (s, 2H), 9.15 (s, 2H), 8.23 (s, 1H), 7.89 (d, 1H, J=8.5 Hz), 7.81 (m, 2H), 7.28 (d, 2H, J=8.6 Hz), 7.20 (d, 1H, J=8.0 Hz), 6.99 (t, 1H, J=8.0 Hz), 6.87 (d, 2H, J=8.6 Hz), 4.22 (t, 2H, J=6.9 Hz), 3.71 (s, 3H), 3.03 (t, 2H, J=6.9 Hz).

MS (ESI, M⁺+1): Calc. 402.17; Found 403.1.

Ex. 166

¹H NMR (DMSO-d₆) δ: 9.41 (s, 2H), 9.07 (s, 2H), 8.20 (s, 1H), 7.86 (d, 1H, J=8.5 Hz), 7.75 (m, 2H), 7.49 (s, 1H), 7.33 (m, 3H), 7.20 (d, 1H, J=8.0 Hz), 6.97 (t, 1H, J=8.0 Hz), 4.26 (t, 2H, J=6.7 Hz), 3.10 (t, 2H, J=6.7 Hz).

MS. (ESI, M⁺+1): Calc. 406.14; Found 407.0.

Ex. 167

¹H NMR (DMSO-d₆) δ: 9.39 (s, 2H), 9.04 (s, 2H), 8.19 (s, 1H), 7.85 (d, 1H, J=8.5 Hz), 7.74 (m, 2H), 7.38 (m, 4H), 7.18 (d, 1H, J=8.0 Hz), 6.96 (t, 1H, J=8.0 Hz), 4.24 (t, 2H, J=6.7 Hz), 3.08 (t, 2H, J=6.7 Hz).

MS (ESI, M⁺+1): Calc. 406.14; Found 407.0.

Ex. 168

¹H NMR (DMSO-d₆) δ: 9.36 (s, 2H), 9.00 (s, 2H), 8.19 (s, 1H), 7.83 (d, 1H, J=8.5 Hz), 7.40 (dd, 2H, J=8.3, 5.9 Hz), 7.15 (m, 3H), 6.96 (t, 1H, J=8.0 Hz), 4.23 (t, 2H, J=6.6 Hz), 3.08 (t, 2H, J=6.6 Hz).

MS (ESI, M$^+$+1): Calc. 390.15; Found 391.0.

Ex. 169

$^1$H NMR (DMSO-d$_6$) δ: 9.41 (s, 2H), 9.07 (s, 2H), 8.40 (s, 1H), 8.22 (m, 2H), 7.98–7.69 (m, 5H), 7.27 (d, 1H, J=8.1 Hz), 7.03 (t, 1H, J=8.1 Hz), 5.38 (s, 2H).

MS (ESI, M$^+$+1): Calc. 403.13; Found 403.9.

Ex. 170

$^1$H NMR (DMSO-d$_6$) δ: 9.42 (s, 2H) 9.12 (s, 2H) 8.25 (d, 1H, J=1.1) 7.95 (d, I H, J=8.5) 7.76 (d, 1H, J=1.1) 7.27 (t, 1H, J=8.2) 6.63 (d, 2H, J=8.2).

MS (bioion) found: 269 Theoretical: 268.1.

Ex. 171

$^1$H NMR (DMSO-d$_6$) δ: 9.42 (s, 2H), 9.09 (s, 2H), 8.21 (s, 1H), 7.87 (d, 1H, J=8.5 Hz), 7.77 (m, 2H), 7.53 (dd, 2H, J=7.8, 5.7 Hz), 7.22 (m, 3H), 6.98 (t, 1H, J=8.1 Hz), 5.18 (s, 2H).

MS (ESI, M$^+$+1): Calc. 376.13; Found 376.9.

Ex. 172

$^1$H NMR (DMSO-d$_6$) δ: 9.53 (s, 2H), 9.25 (s, 2H), 8.24 (s, 1H), 7.93–7.80 (m, 7H), 7.28 (d, 1H, J=8.1 Hz), 7.01 (t, 1H, J=8.1 Hz), 4.35 (t, 2H, J=5.7 Hz), 4.00 (t, 2H, J=5.7 Hz).

MS (ESI, M$^+$+1): Calc. 441.14; Found 442.3.

Ex. 173

$^1$H-NMR (DMSO-d$_6$) δ: 9.39 (s, 2H), 9.05 (s, 2H), 8.20 (s, 1H), 7.87–7.72 (m, 3H), 7.38–7.16 (m, 6H), 6.97 (t, 1H, J=9.3 Hz), 4.25 (t, 2H, J=7.0 Hz), 3.08 (t, 2H, J=7.0 Hz).

MS (ESI, M$^+$+1): Calc. 372.16; Found 373.0.

The following discussion illustrates transformation of compounds of Formula Ia, Table 2, into compounds of Formula I. Compounds of Formula I prepared by these schemes are included in Table 2a.

Compounds of Formula I in which any of $R^2$, $R^3$, $R^4$ and $R^5$ are amino can be prepared by reducing a corresponding compound of Formula Ia in which $R^2$, $R^3$, $R^4$ or $R^5$ nitro. The reduction can be accomplished in any number of ways known to one skilled in the art. For example, a representative way of reducing the nitro group is by catalytic hydrogenation. The catalytic hydrogenation is carried out by mixing an appropriate nitro compound of Formula I with Pearlman's catalyst in a suitable solvent (e.g., methanol). Air from the reaction vessel is removed under reduced pressure and the reaction vessel is then charged with an atmosphere of hydrogen. The resulting mixture is stirred for about 18 hours, is filtered to remove the catalyst, and is concentrated to yield the desired amine.

Compounds of Formula I in which any of $R^2$, $R^3$, $R^4$ and $R^5$ are —NR$^{10}$R$^{24}$ wherein R$^{24}$ is other than hydrogen, can be prepared by reductive amination of a suitable aldehyde with a corresponding compound of Formula I in which $R^2$, $R^3$, $R^4$ or $R^5$ is amino. The reductive amination is carried out by stirring a mixture of the amine with the aldehyde and molecular sieves, in methanol under an atmosphere of nitrogen for about 2 hours. Sodium cyanoborohydride is co then added to the reaction mixture and the resulting mixture is stirred at ambient temperature for about 15 hours. The reaction mixture is then filtered through celite and the filtrate is concentrated. The residue may be purified by chromatography.

Compounds of Formula I in which any of $R^2$, $R^3$, $R^4$ and $R^5$ comprise groups containing an annular nitrogen atom may be further derivatized to an corresponding N-1-iminoethyl substituted derivative by reacting the compound with ethyl acetamidate. For example, a compound of Formula I in which $R^4$ is 4-(1-(1-iminoethyl)piperindin-4-yloxy)benzylamino can be prepared by reacting a corresponding compound of Formula I in which $R^4$ is 4-piperidin-4-yloxybenzyl amino with ethyl acetamidine hydrochloride and triethyl amine in ethanol and stirring over night under a nitrogen atmosphere. The reaction mixture is concentrated under reduced pressure and residue may be purified by column chromatography.

Compounds of Formula I in which any of $R^2$, $R^3$, $R^4$ and $R^5$ are or contain a carboxy group can be prepared by hydrolyzing a corresponding compound of Formula Ia in which $R^2$, $R^3$, $R^4$ or $R^5$ is or contains a —COOR$^{10}$ group. For example, a compound of Formula I in which $R^3$ is carboxymethoxy can be prepared by hydrolyzing a compound of Formula I in which $R^3$ is ethoxy carbonyl methoxy.

Compounds of Formula Ia in which any of $R^2$, $R^3$, $R^4$ and $R^5$ are or contain a carboxy group can be derivatized to a compound of Formula I in which $R^2$, $R^3$, $R^4$ or $R^5$ is or contains —CONR$^{11}$R$^{12}$ or —C(O)NR)$^{33}$R$^{34}$ by reacting the acid with an appropriate amine. For example a compound of Formula I in which $R^3$ is carboxy methoxy is converted to a compound in which $R^3$ is 2-(1,3-dihydro isobenzofuran-5-yl)ethylcarbomyl methoxy by reacting the acid with 2-(1,3-dihydro isobenzofuran-5-yl)ethyl amine in the presence of a suitable coupling agent (e.g., N,N'-carbonyl diimidazole (CDI), PyBOP, and the like)

Compounds of Formula I in which any of $R^2$, $R^3$, $R^4$ and $R^5$ are halo can be prepared by halogenating a corresponding compound of Formula I in which $R^2$, $R^3$, $R^4$ and $R^5$ is hydrogen. For example, a compound of Formula I in which $R^2$ and $R^4$ are bromo was prepared by reacting 4-(6-carbamimidoyl-1H-benzoimidazol-2-yl)-3-hydroxy phenoxy acetic acid (Example 203, Table 2a) (100 mg, 0.307 mmol) with N-Bromosuccinimide (55 mg, 0.307 mmol) in anhydrous DMF (5 mL). The reaction mixture is allowed to stir at room temperature for 1 hr forming a deep red-orange solution, which is added dropwise to a stirring solution of anhydrous ether and the resultant red precipitate is isolated and dried under vacuum to afford 115 mg (77.4%) of a red solid. The crude material is dissolved in a 50:50 mixture of 1N HCl/MeOH (10 mL) and purified using reverse-phase C-18 HPLC (2–50% gradient) to yield 10 mg of 2,6-dibromo-4-(6-carbamimidoyl-1H-benzoimidzol-2-yl)-3-hydroxy phenoxy acetic acid (Example 204, Table 2a) as a yellow solid.

Compounds of Formula I in which Q, $Q^1$, $Q^2$ and/or $Q^3$ or $L^1$, $L^2$, $L^3$ and/or $L^4$ are N—R$^{37}$ can be prepared by reacting a corresponding compound of Formula I in which Q, $Q^1$, $Q^2$ and/or $Q^3$ or $L^1$, $L^2$, $L^3$ and/or $L^4$ is NH with a suitable protected amino acid. The reaction is typically carried out in the presence of a coupling agent (e.g., PyBOP, CDI, and the like). For example a compound of Formula I in which $R^2$ is 1-aminoacetyl pyrrolidin-3yloxy was prepared by coupling a PyBrOP peptide onto Example 139, Table 2 to give the product Example 208, Table 2a.

tert-Butoxycarbonyl amino acetic acid and 2-(2-hydroxy-3-pyrrolidin-3-yloxyphenyl)-1H-benzoimidazole-5-carboxamide Example 139 (Table 2), were suspended in DMF (1.0 mL) under a N$_2$ atmosphere. Diisopropylethylamine was added and the mixture was cooled in a water/ice bath at 0° C. PyBrOP was quickly added to the cold suspension. The mixture was allowed to warm to ambient temperature to form a solution. The reaction was allowed 2 h and then the reaction mixture was added to EtOAc forming a precipitate. The precipitate was isolated and dissolved in 3M aqueous HCl using a vortex mixer. This solution was kept at rppm temperature for 25 minutes and then diluted with $H_2O$ and $CH_3CN$. The mixture was filtered. Preparatory HPLC (linear gradient, 2–35% $CH_3CN$ in 0.01 M aqueous HCl) followed by lyophilization gave 28 mg a of Example 208, Table 2a.

Analytical HPLC, (1=214 nm), 99%.

Compounds of Formula I in which any of $R^2$, $R^3$, $R^4$ and $R^5$ are or contain a $NHSO_2R$ (R=alkyl, aryl, and the like) group can be prepared by sulfonating a corresponding compound of Formula I in which $R^2$, $R^3$, $R^4$ or $R^5$ are or contain an amino group. For example, a compound of Formula I wherein $R^2$ is methyl sulfonyl amino is prepared as follows.

A mixture of 2-(3'-Amino-5-chloro-2-hydroxy-biphenyl-3-yl)-1H-benzoimidazole-5-carboxamidine 73 (0.070 g, 0.15 mmol) and THF/water (1:1, 0.5 mL) is chilled (0° C.) and treated with 2 N NaOH (0.16 mL, 0.32 mmol) and methane sulfonyl chloride (0.013 mL, 0.16 mmol) in alternating portions. The mixture is kept at 0° C. for 1 h and then treated with another portion of 2 N NaOH (0.016 mL, 0.032 mmol) and methane sulfonyl chloride (0.001 mL, 0.013 mmol). After another 1 h, the solvents were reduced in volume under reduced pressure, and the crude material is purified by C18 reversed-phase HPLC (2–65% $MeCN/H_2O$ containing 20 mM HCl, over 50 min.). The appropriate fractions were pooled and the solvent is removed under reduced pressure. 2-(5-chloro-2-hydroxy-3'-methanesulfonylamino-biphenyl-3-yl)-1H-benzoimidazole-5-carboxamidine 74 is obtained as a tan powder (0.012 g, 16% yield) (Example 288, Table 2a):

Compounds of Formula I in which A is 4-(5-carbamimidoyl-4,5,6,7-tetrahydro-1H-imidazo[4,5-c]pyridin-2-yl can be prepared by hydrogenating a corresponding 1H-imidazo[4,5-c]pyridinyl derivative to give a 4,5,6,7-tetrahydro-1H-imidazo[4,5-c]pyridinyl intermediate and then reacting the intermediate with 1H-pyrazole-1-carboxamide. The hydrogenation is carried out under standard conditions. For example, the hydrogenation can be effected with a suitable catalyst (e.g., $PtO_2$, etc.) in a suitable solvent (e.g., methanol).

The reaction with the amidine typically is carried out in the presence of base (e.g., Hunig's base, etc.) in a suitable solvent (e.g., anhydrous, DMF) at 20° to 100° C. and requires 12 to 24 h to complete. Compounds of Formula I can be prepared by proceeding as in Scheme XXI but substituting an appropriate diamino pyrrolidine derivative for the diamino benzene derivative.

$PtO_2$ (20 mg) and concentrated hydrochloric acid (5 mL) was added to a solution of 2-[2-Hydroxy-3-(1H-imidazo[4,5-c]pyridin-2-yl)-phenyl]-1H-benzoimidazole-5-carboxamidine (Example 120, Table 2) (100 mg, 0.27 mmol) in MeOH (20 mL). The mixture was hydrogenated at 50 psi in a Parr apparatus for 12–18 h. After the hydrogenation was completed, the catalyst was filtered and the filtrate was concentrated to dryness. HPLC purification (2–50% acetonitrile/60 minutes) followed by lyophilization afforded 2-[2-Hydroxy-3-(4,5,6,7-tetrahydro-3H-imidazo[4,5-c]pyridin-2-yl)-phenyl]-1H-benzoimidazole-5-carboxamidine 75 as pale yellow powder (20 mg, 20% yield) (Example 296, Table 2a).

Hunig's base (0.042 mL, 0.24 mmol) was added to a suspension of 2-[2-Hydroxy-3-(4,5,6,7-tetrahydro-3H-imidazo[4,5-c]pyridin-2-yl)-phenyl]-1H-benzoimidazole-5-carboxamidine 75 (19 mg, 0.04 mmol) and 1H-pyrazole-1-carboxamidine hydrochloride (12 mg, 0.082 mmol) in anhydrous DMF and the mixture was stirred for 12–18 h at 80° C. The mixture was poured into water (15 mL)/diethyl ether (15 mL). The aqueous layer was washed with diethyl ether (3×10 mL) and concentrated to dryness. HPLC purification (2–50% acetonitrile/60 minutes) afforded 2-[3-(5-Carbamimidoyl-1H-benzoimidazol-2-yl)-2-hydroxy-phenyl]-3,4,6,7-tetrahydro-imidazo[4,5-c]pyridine-5-carboxamidine 76 as a lyophilized yellow light powder (15.5 mg, 75% yield) (Example 298, Table 2a).

Ex. 193

$^1$H NMR (300 MHz, $^1$H, DMSO-d6): δ 9.5 ppm, (s, 2H), 9.2 (s, 2H), 8.2 (s, 1H), 7.9–7.7 (m, 3H), 7.65 (bs, 2H), 7.55 (d, 2H), 7.2 (d, 1H), 7.0 (t, 1H), 4.3 (t, 2H), 3.15 (t, 2H), 3.05 (s, 6H).

MS (ESI) m/z=415.8 (MH+, calc 415.2).

Ex. 194

$^1$H NMR (300 MHz, $^1$H, DMSO-d6): δ 9.5 ppm, (s, 2H), 9.3 (s, 2H), 8.1 (s, 2H), 7.8 (d, 1H), 7.6 (s, 1H), 2.3 (s, 3H).

MS (ESI) m/z=362.6, 364.3 (MH+, calc 362.0).

Ex. 195

$^1$H NMR (300 MHz, $^1$H, DMSO-d6): δ 9.5 ppm, (s, 2H), 9.2 (s, 2H), 8.3 (s, 1H), 8.1 (bs, 2H), 7.9 (d, 1H), 7.8 (d, 1H), 7.2 (d, 1H), 6.9 (d, 1H), 3.9 (s, 3H), 2.6 (m, 4H), 1.7 (t, 2H).

MS (ESI) m/z=339.9 (MH+, calc 339.17).

Ex. 196

$^1$H NMR (300 MHz, $^1$H, DMSO-d6): δ 9.4 ppm, (s, 2H), 9.0 (s, 2H), 8.2 (bs, 1H), 8.0 (s, 1H), 7.9 (m, 1H), 7.7 (d, 1H), 7.45–7.25 (m, 2H), 7.2 (d, 2H), 6.9 (d, 1H), 3.8 (s, 3H), 2.4 (s, 3H).

MS (ESI) m/z=372.9 (MH+, calc 372.2).

Ex. 197

$^1$H NMR (300 MHz, $^1$H, DMSO-d6): δ 9.5 ppm, (s, 2H), 9.2 (s, 2H), 8.0 (s, 2H), 7.8–7.65 (bs, 1H), 7.6 (d, 2H), 7.4 (t, 2H), 7.35–7.25 (m, 2H), 2.35 (t, 3H).

MS (ESI) m/z=360.9 (MH+, calc 360.1).

Ex. 198

$^1$H NMR (300 MHz, $^1$H, DMSO-d6): δ 9.4 ppm, (s, 2H), 9.1 (s, 2H), 8.2 (bs, 1H), 8.0 (s, 1H), 7.9 (d, 1H), 7.7 (d, 1H), 7.3 (s, 1H), 7.2 (s, 1H), 7.1 (d, 1H), 7.0 (d, 1H), 6.0 (s, 2H), 2.3 (s, 3H).

MS (ESI) m/z=386.9 (MH+, calc 386.14).

Ex. 199

$^1$H NMR (300 MHz, $^1$H, DMSO-d6): δ 9.4 ppm, (s, 2H), 9.1 (s, 2H), 8.2 (s, 1H), 8.0 (s, 1H) 7.8 (d, 1H), 7.7 (d, 1H), 7.6 (d, 2H), 7.3 (s, 1H), 7.0 (d, 2H), 3.8 (s, 3H), 2.3 (s, 3H).

MS (ESI) m/z=372.9 (MH+, calc 372.2).

Ex. 200

¹H NMR (300 MHz, ¹H, DMSO-d6): δ 9.4 ppm, (s, 2H), 9.1 (s, 2H) 8.2 (s, 1H), 8.0 (s, 1H), 7.8 (d, 1H), 7.7 (d, 1H), 7.4 (t, 1H), 7.2 (t, 1H), 7.15–7.05 (m, 2H), 7.0 (t, 1H), 3.7 (s, 3H), 2.3 (s, 3H).

MS (ESI) m/z=373.0 (MH+, calc 372.2).

Ex. 201

¹H NMR (300 MHz, ¹H, DMSO-d6): δ 9.4 ppm (s, 2H), 9.1 (s, 2H), 8.6 (d, 1H), 8.3 (s, 1H), 8.1 (d, 1H), 7.9 (d, 1H), 7.8 (d, 1H), 7.3 (t, 1H).

MS (ESI) m/z=297.8 (MH+, calc 297.3).

EXAMPLE 267

Table 2a

To a solution of 2-[(4-amino)-2-phenol]-3H-benzoimidazole (0.084 g, 0.31 mmol) in 4.5 ml of 2:1 DMF/DCM under nitrogen, is added 4-morpholinecarbonyl chloride (35 uL, 0.30 mmol) followed by N,N-diisopropylethylamine (108 uL, 0.62 mmol, 2 eq.). After stirring for 12–18 h the solvent is removed by rotovapor and the crude residue purified by reverse phase HPLC. Appropriate fractions were combined and lyophilized to a yellow solid (18 mg, 15% yield).

EXAMPLE 285

Table 2a

To a cold (0° C.) solution of 2-(5-amino-2-hydroxy-phenyl)-3H-benzimidazole-5-carboxamdine dihydrochloride (0.203 g, 0.6 mmol) in dry pyridine under nitrogen is added methane sulfonyl chloride (93 uL, 1.2 mmol) dropwise. After stirring the solution for 12–18 h followed by warming it to ambient temperature the solvent is removed and the residue is purified by reverse phase HPLC. Appropriate fractions were lyophilized to an off white solid. (125 mg, 60% yield).

TABLE 2a

Formula I

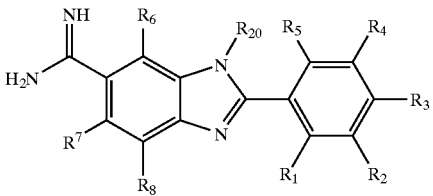

in $R^1$ is OH; and $R^5$, $R^6$, $R^8$, $R^9$ and $R^{20}$ represent hydrogen.

| Ex. No. | $R^2$ | $R^3$ | $R^4$ | $R^8$ |
|---|---|---|---|---|
| 301 | H | 2-(Naphthalene-2-sulfonylamino)-ethoxy | H | H |
| 302 | H | (2,3-Dichloro-benzylcarbamoyl)-methoxy | H | H |
| 303 | H | —OCH₂COOH | H | H |
| 304 | Br | —OCH₂COOH | Br | H |
| 305 | H | (3-Chloro-benzylcarbamoyl)-methoxy | H | H |
| 306 | H | (3-bromo-benzylcarbamoyl)-methoxy | H | H |
| 307 | H | H | 4-[1-(1-Imino-ethyl)-piperidin-3-ylmethoxy]-benzylamino | H |
| 308 | Pyrrolidin-2-ylmethoxy | H | H | |
| 309 | H | H | NH₂ | H |
| 310 | H | [(Benzo[1,3]dioxol-5-ylmethyl)-carbamoyl]-methoxy | H | H |
| 311 | H | [(3-Chloro-benzylcarbamoyl)-methoxy] | H | H |
| 312 | 1-carbamimidoy 1-piperidin-3-ylmethoxy | H | H | H |
| 313 | H | Benzylcarbamoyl-methoxy | H | H |
| 314 | H | [2-(1H-Indol-2-yl)-ethylcarbamoyl]-methoxy | H | H |
| 315 | H | (3,5-Dimethoxy-benzylcarbamoyl)-methoxy | H | H |
| 316 | H | 2-[2-(3,4-Dichloro-phenyl)-acetylaminol-ethoxy | H | H |
| 317 | H | (2-Methoxy-benzylcarbamoyl)-methoxy | H | H |
| 318 | H | 3-Benzoylamino-propoxy | H | H |
| 319 | H | [2-(4-Hydroxy-phenyl)-ethylcarbamoyl]-methoxy | H | H |
| 320 | H | 3-[2-(3-Bromo-phenyl)-acetylamino]-propoxy | H | H |
| 321 | H | 3-(3-Phenyl-propionylamino)-propoxy | H | H |
| 322 | H | 2-phenylacetylamino-ethoxy | H | H |
| 323 | H | 2-Phenylmethanesulfonylamino-ethoxy | H | H |
| 324 | H | 2-(6,7-Dimethoxy-3,4-dihydro-1H-isoquinolin-2-yl)-2-oxo-ethoxy | H | H |
| 325 | (2-Cyano-ethylcarbamoyl)-methoxy | H | H | H |
| 326 | H | 2-(3-Phenyl-propionylamino)-ethoxy | H | H |
| 327 | H | 2-Benzoylamino-ethoxy | H | H |
| 328 | H | H | 3-(Piperidin-4-yloxy)-benzylamino | H |
| 329 | H | [2-(3,4-Dimethoxy-phenyl)-ethylcarbamoyl]-methoxy | H | H |
| 330 | (2-Morpholin-4-yl-ethylcarbamoyl)-methoxy | H | H | H |
| 331 | 2-(2-Amino-3-hydroxy-propionyl)-2,3,4,7-tetrahydro-1H-[2]pyrindin-6-yl | H | H | H |
| 332 | —OCH₂C(O)NH—CH₂CH₂—NHC(O)CH₂ | H | H | H |

-continued

| Ex. No. | R² | R³ | R⁴ | R⁸ |
|---|---|---|---|---|
| 333 | 1-(2-Amino-3-methyl-butyryl)-pyrrolidin-2-ylmethoxy | H | H | H |
| 334 | H | H | 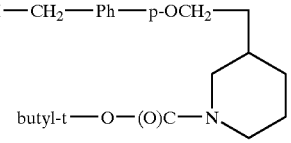 | H |
| 335 | (2-p-Tolyl-ethylcarbamoyl)-methoxy | H | H | H |
| 336 | 5-Iminomethyl-4,5,6,7-tetrahydro-3H-imidazo[4,5-c]pyridin-2-yl | H | H | H |
| 337 | (2,3-Dimethoxy-benzylcarbamoyl)-methoxy | H | H | H |
| 338 | H | H | 3-(4-Amino-cyclohexyl)-propylamino | H |
| 339 | H | [(1H-Benzoimidazol-2-ylmethyl)-carbamoyl]-methoxy | H | H |
| 340 | 5-Acetyl-4,5,6,7-tetrahydro-3H-imidazo-[4,5-c]pyridin-2-yl | H | H | H |
| 341 | H | —OCH₂COOH | Br | H |
| 242 | H | H | 4-(4-Acetimidoylamino-cyclohexyloxy)-benzyl-amino | H |
| 343 | Br | OCH₂CO₂C₂H₅ | Br | H |
| 344 | H | H | CH₂CH₂CO₂Me | H |
| 345 | H | H | 4-[1-(1-Imino-ethyl)-piperidin-4-yloxy)-benzyl-amino | H |
| 346 | 1-Aminoacetyl-piperidin-3-ylmethoxy | H | H | H |
| 347 | H | (2,3-Dimethoxy-benzylcarbamoyl)-methoxy | H | H |
| 348 | H | H | 3-(4-Acetimidoylamino-cyclohexyloxy)-benzyl-amino | H |
| 349 | H | 2-(2,3-Dichloro-benzoylamino)-ethoxy | H | H |
| 350 | H | naphthalen-1-ylcarbamoylmethoxy | H | H |
| 351 | H | H | 4-[1-(1-Imino-ethyl)-pyrrolidin-3-yloxy]-benzyl-amino | H |
| 352 | H | O(CH₂)₂NHC(O)CH₂—Ph | H | H |
| 353 | Br | H | (CH₂)₂C(O)NH(CH₂)₂—Ph | H |
| 354 | O(CH₂)₂NHCOPh | H | H | H |
| 355 | 2-(3-Carbamoyl-propionylamino)-ethoxy | H | H | H |
| 356 | Br | H | 4-[2-(2-Pyridin-2-yl-ethylcarbamoyl)-ethyl]-benzoic acid | H |
| 357 | Br | H | (CH₂)₂C(O)NH(CH₂)₃—Ph | H |
| 358 | H | [(Naphthalen-1-ylmethyl)-carbamoyl]-methoxy | H | H |
| 359 | H | (3,4-Dimethoxy-benzylcarbamoyl)-methoxy | H | H |
| 360 | OCH₂NHCH₂COOC(CH₃)₃ | H | H | H |
| 361 | 4-(2-Hydroxy-acetylamino)-1-methyl-butoxy | H | H | H |
| 362 | H | (3,5-Bis-trifluoromethyl-benzylcarbamoyl)-methoxy | H | H |
| 363 | H | 2-(3,4-Dichloro-benzoylamino)-ethoxy | H | H |
| 364 | H | H | 4-[2-(2-Hydroxycarbonimidoyl-pyridin-3-yl-oxy)-ethoxy]-benzylamino | H |
| 365 | H | H | 4-(4-Amino-cyclohexyloxy)-benzylamino | H |
| 366 | H | H | 3-(3,4-Dicyano-phenoxy)-benzylamino | H |
| 367 | H | H | (Morpholine-4-carbonyl)-amino | H |
| 368 | 1-(2-Amino-3-methyl-butyryl)-pyrrolidin-2-ylmethoxy | H | H | H |
| 369 | H | 1-Benzoyl-piperidin-4-yloxy | H | H |
| 371 | 2-(5-Oxo-4,5-dihydro-3H-pyrrol-2-ylamino)-ethoxy | H | H | H |
| 372 | 5-(2-Amino-3-carboxy-propionyl)-4,5,6,7-tetrahydro-3H-imidazo[4,5-c]pyridin-2-yl | H | H | H |
| 373 | OCH₂C(O)NH(CH₂)₂CH(CH₃)₂ | H | H | H |
| 374 | 2-Benzenesulfonylamino-ethoxy | H | H | H |
| 375 | H | (9H-Fluoren-9-ylcarbamoyl)-methoxy | H | H |
| 376 | H | 2-Oxo-2-(1,3,4,9-tetrahydro-b-carbolin-2-yl)-ethoxy | H | H |
| 377 | H | 1-(3-Phenyl-propionyl)-piperidin-4-yloxy | H | H |
| 378 | 1-(3-Amino-propionyl)-pyrrolidin-2-ylmethoxy | H | H | H |
| 379 | H | H | 1-(1-Dimethylsulfamoyl-1H-pyrrol-3-yl)-2-hydroxy-ethylamino | H |
| 380 | 2-(2-Chloro-phenyl)-ethoxy | H | H | H |
| 381 | H | H | 4-(2-Amino-thiazol-5-ylmethoxy)-benzylamino | H |
| 382 | H | H | 4-(2,4,6-triamino-pyrimidin-5-ylmethyl)-benzylamino | H |

-continued

| Ex. No. | R² | R³ | R⁴ | R⁸ |
|---|---|---|---|---|
| 383 | 2-[2-(2,5-Dioxo-imidazolidin-4-yl)-acetyl-amino]-ethoxy | H | H | H |
| 384 | 4-benzylcarbamoyl-methoxy | H | H | H |
| 385 | H | H | NH—SO₂—CH₃ | H |
| 386 | 2-[(Pyridine-3-carbonyl)-amino]-ethoxy | H | H | H |
| 387 | Ph-m-NH₂ | H | Cl | H |
| 388 | —Ph-m-(NH—SO₂—CH₃) | H | Cl | H |
| 389 | Br | H | —CH₂CH₂COOH | H |
| 390 | Br | H | 2-[2-(2,4-Dichloro-phenyl)-ethylcarbamoyl]-ethyl | H |
| 391 | Br | H | CH₂CH₂COOCH₃ | H |
| 393 | 1-(3-Amino-propionyl)-pyrrolidin-2-ylmethoxy | H | H | H |
| 394 | [(Tetrahydro-furan-2-ylmethyl)-carbamoyl]-methoxy | H | H | H |
| 395 | OCH₂CO₂H | H | H | H |
| 396 | 4,5,6,7-Tetrahydro-3H-imidazo[4,5-c]-pyridin-2-yl | H | H | H |
| 397 | piperidine-3-yl | H | Cl | H |
| 298 | 5-Carbamimidoyl-4,5,6,7-tetrahydro-3H-imidazo[4,5-c]pyridin-2-yl | H | H | H |
| 399 | 1-(2-Amino-3-methyl-butyryl)-pyrrolidin-2-ylmethoxy | H | H | H |
| 400 | 1-(2-Amino-3-methyl-butyryl)-pyrrolidin-2-ylmethoxy | H | H | H |
| 401 | 5-Aminoacetyl-4,5,6,7-tetrahydro-3H-imidazo[4,5-c]pyridin-2-yl | H | H | H |
| 402 | 5-(3-Amino-propionyl)-4,5,6,7-tetrahydro-3H-imidazo[4,5-c]pyridin-2-yl | H | H | H |
| 403 | 1-(2-Amino-1-imino-ethyl)-piperidin-3-yl | H | Cl | H |
| 404 | H | H | 4-(4-[phenylmethyl amino]-phenoxy)-piperidine-carboxylic acid tert-butyl ester | H |
| 405 | 2-(3-Biphenyl-2-yl-ureido)-ethoxy | H | H | H |
| 406 | O(CH₂)₂—NH—C(O)—CH₂OCH3 | H | H | H |
| 407 | H | H | 4-(Piperidin-4-yloxy)-benzylamino | H |
| 408 | H | H | 4-(Piperidin-3-ylmethoxy)-benzylamino | H |
| 409 | H | 3-(3,4-Dichloro-benzoylamino)-propoxy | H | H |
| 410 | H | Pyrrolidin-2-ylmethoxy | H | H |
| 411 | H | (Benzyl-methyl-carbamoyl)-methoxy | H | H |
| 412 | H | OCH₂C(O)NH—(CH₂)₃Ph | H | H |
| 413 | Br | (2,3-Dichloro-benzylcarbamoyl)-methoxy | Br | H |
| 414 | H | H | 4-(pyrrolidin-3-yloxy)-benzylamino | H |
| 415 | H | H | 4-[1-(1-Imino-ethyl)-piperidin-4-yloxy]-benzyl-amino | H |
| 416 | H | H | 4-(2-Acetylamino-thiazol-5-ylmethoxy)-benzyl-amino | H |
| 417 | H | H | 4-[1-(1-Imino-ethyl)-pyrrolidin-2-ylmethoxy]-benzylamino | H |
| 418 | H | H | 3-[1-(1-Imino-ethyl)-pyrrolidin-3-yloxy]-benzylamino | H |
| 419 | H | 2-(3-bromo-benzoylamino)-ethoxy | H | H |
| 420 | H | 2-(3,5-Dichloro-benzoylamino)-ethoxy | H | H |
| 421 | H | 2-[(Naphthalene-2-carbonyl)-amino]-ethoxy | H | H |
| 422 | Br | H | 2-Phenylcarbamoyl-ethoxy | H |
| 423 | O(CH₂)₂—NH—C(O)CH₂NH—COO—C(CH₃)₃ | H | H | H |
| 424 | O(CH₂)₂—NH—C(O)NH—CH₂—Ph | H | H | H |
| 425 | O(CH₂)₂—NH—C(O)CH₂NH₂ | H | H | H |
| 426 | O(CH₂)₂—NH—C(O)CH₂—Ph | H | H | H |
| 427 | O(CH₂)₂—NH—C(O)(CH₂)₂—Ph | H | H | H |
| 428 | 3-Amino-benzyloxy | H | H | H |
| 429 | Br | OH | Br | H |
| 430 | H | H | 3-(4-Amino-cyclohexyloxy)-benzylamino | H |
| 431 | H | H | 3-[4-(methylamino)-phenoxy]-pyrrolidine-1-carboxylic acid tert-butyl ester | H |
| e32 | Br | H | 2-[(benzo[1,3]dioxol-5-ylmethyl)-carbamoyl]-ethyl | H |
| 333 | Br | H | 2-(2-Morpholin-4-yl-ethylcarbamoyl)-ethyl | H |
| e34 | Br | H | 2-Benzylcarbamoyl-ethyl | H |
| e35 | Br | H | Benzylcarbamoyl-methyl | H |
| e36 | Br | H | phenethylcarbamoyl-methyl | H |
| e37 | Br | H | (2-Hydroxy-ethylcarbamoyl)-methyl | H |
| 438 | Br | H | tetrahydro-furan-2-ylmethyl-carbamoyl-methyl | H |
| 439 | Br | H | Benzo[1,3]dioxol-5-ylmethyl)-carbamoyl]-methyl | H |
| 440 | Br | H | 2-(3-Chloro-benzylcarbamoyl)-ethyl | H |

-continued

| Ex. No. | R² | R³ | R⁴ | R⁸ |
|---|---|---|---|---|
| 441 | Br | H | 2-(4-Chloro-benzylcarbamoyl)-ethyl | H |
| 442 | Br | H | 2-(Methyl-phenethyl-carbamoyl)-ethyl | H |
| 3443 | Br | H | 2-Methylcarbamoyl-ethyl | H |
| 444 | Br | H | 2-dimethylcarbamoyl-ethyl | H |
| 445 | 3-aminophenyl | H | 2-carboxy-ethyl | H |
| 446 | 3-nitrophenyl | H | 2-carboxy-ethyl | H |
| 447 | 3-aminophenyl | H | 2-Phenethylcarbamoyl-ethyl | H |
| 448 | Br | H | 2-Phenethylcarbamoyl-ethyl | H |
| 449 | Cl | H | 2-Benzylcarbamoyl-ethyl | H |
| 450 | Cl | H | 2-Phenethylcarbamoyl-ethyl | H |
| 451 | Cl | H | 3-(3,4-Dihydro-1H-isoquinolin-2-yl)-3-oxo-propyl | H |
| 452 | Cl | H | 2-(2,2-Diphenyl-ethylcarbamoyl)-ethyl | H |
| 453 | Cl | H | CH₂CH₂COOH | F |
| 454 | Cl | H | 2-[(naphthalen-1-ylmethyl)-carbamoyl]-ethyl | H |
| 455 | Br | H | 2-tert-Butoxycarbonylamino-ethyl | H |
| 456 | Cl | H | 2-(Benzhydryl-carbamoyl)-ethyl | H |
| 357 | Br | H | 2-amino-ethyl | H |
| 458 | Cl | H | 2-[(Furan-2-ylmethyl)-carbamoyl]-ethyl | H |
| 459 | Br | H | 3-(4-Chloro-benzenesulfonylamino)-3-oxo-propyl | H |
| 460 | Br | H | 2-Phenylmethanesulfonylamino-ethyl | H |
| 461 | Br | H | 2-(Naphthalene-2-sulfonylamino)-ethyl | H |
| 462 | Cl | H H | 2-(3,5-dimethoxy-benzylamino)-ethyl | H |

*R⁷ = C(=O)NH₂

Spectral data for compounds listed in Table 2 above is provided below:

Ex. 301

Mass, MS (ESI) 481.11 (calc.); 482.2. (obs.).

Ex. 308

¹H NMR (DMSO-d₆) δ: 9.50 (s, 2H), 9.24 (s, 2H), 8.4–8.1 (br m, 2H), 8.00–7.86 (m, 2H), 7.79 (d, 1H, J=9 Hz), 7.26 (t, 1H, J=9 Hz), 7.02 (t, 1H, 9 Hz), 5.19 (d, 1H, J=22 Hz), 4.25–3.25 (br.m), 2.12–2.00 (br m, 2H).

MS (ESI): 394.18 (calc.); 394.9 (obs.).

Ex. 312

¹H-NMR (methanol-d₆) δ ppm: 9.55 (s, 2H), 9.05 (s, 2H), 8.35 (s, 1H), 8.07 (d, 1H J=8 Hz), 7.95, (d, 1H, J=8 Hz), 7.69 (d, 1H, J=8 Hz), 7.40 (d, 1H, J=8 Hz), 7.17 (t, 1H, J=8 Hz), 4.20–4.00 (m, 3H), 3.88 (br.d, 1H), 3.32 (m, 1H), 3.25–3.05 (m, 2H), 2.40 (br.m, 1H), 2.08 (br.m, 1H), 1.90 (br.m, 1H).

MS (Bioion): 407.21 (calc.); 408 (obs.).

Ex. 325

¹H NMR (DMSO-d₆) δ: 9.41 (br.s, 2H), 9.05 (br.s, 2H), 8.22 (s, 1H), 7.90 (d, 1H, J=8.5 Hz), 7.83 (d, 1H, J=8.0 hz), 7.75 (d, 1H, J=8.5 Hz), 7.18 (d, 1H, J=8.0 Hz), 7.01 (t, 1H, J=8.0 Hz), 4.63 (s, 2H), 3.42 (m, 2H), 2.73 (t, 2H, J=6.4 Hz).

MS: 378.14 (calc.); 379.2 (obs.).

Ex. 330

¹H-NMR (DMSO-d₆) δ ppm: 9.54 (s, 2H), 9.26 (s, 2H), 8.27 (s, 1H), 7.94 (m, 2H), 7.81 (d, 1H, J=8.6 Hz), 7.26 (d, 1H, J=8.1 Hz), 7.03 (t, 1H, J=8.1 Hz), 4.65 (s, 2H), 3.95–3.78 (m, 4H), 3.60–3.47 (m, 4H), 3.27–3.10 (m, 4H).

MS (ESI, M⁺+1): Calc. 438.20; Found 439.1.

Ex. 332

¹H NMR (DMSO-d₆) δ: 9.53 (br.s, 2H), 9.23 (br.s, 2H), 8.28 (s, 1H), 7.97 (d, 1H, J=8.5 Hz), 7.92 (d, 1H, J=8.1 Hz), 7.84 (d, 1H, J=8.5 Hz), 7.28 (d, 1H, J=8.1 Hz), 7.05 (t, 1H, J=8.1 Hz), 4.60 (s, 2H), 3.25–3.15 (m, 4H), 1.80 (s, 3H).

MS: 410.17 (calc.); 411.0 (obs.).

Ex. 333

¹H NMR (CD₃OD) δ: 9.45 (s, 2H), 9.15 (s, 2H), 8.38–8.26 (m, 1H), 8.22 9s, 1H), 7.95–7.78 (m, 2H), 7.51 (d, 1H, J=10 Hz), 7.27 (d, 1H, 14 Hz), 6.98 (t, 1H, H=14 Hz), 4.40–4.29 (m, 1H), 4.29–4.20 (d, 1H, J=12 Hz), 4.02 (t, J=9 Hz), 3.85–3.40 (br.m), 2.40–1.80 (br.m, 8H), 0.95 (m, 9H).

MS: 450.24 (calc.); 451.1 (obs.).

Ex. 335

¹H NMR (DMSO-d₆) δ: 9.34 (br.s, 2H), 8.96 (br.s, 2H), 8.20 (s, 1H), 7.88 (d, 1H), J=8.5 Hz), 7.80 (d, 1H, J=7.9 Hz), 7.71 (d, 1H, J=8.5 Hz), 7.14–6.95 (m, 6H), 4.56 (s, 2H), 3.40 (t, 2H, J=7.5 Hz), 2.71 (t, 2H, J=7.5 Hz), 2.22 (s, 3H).

MS: 443.2 (calc.); 444.1 (obs.).

Ex.: 337

¹H NMR (DMSO-d₆) δ: 9.55 (2H, br.s), 9.26 (2H, br.s), 8.28 (1H, s), 7.98–7.82 (3H, m), 7.27 (1H, d, J=8.0 hz), 7.07–6.92 (3H, m), 6.83 (1H, d, J=7.4 Hz), 4.69 (2H, s), 4.40 (2H, s), 3.78 (3H, s), 3.74 (2H, s).

MS(ES): Calc: 475.19; Obs.: 475.7.

Ex. 346

¹H-NMR (DMSO-d₆) δ ppm: 9.45 (sm, 1H), 9.15 (s, 1H), 8.4–8.05 (m, 4H), 8.0–7.7 (m, 4H), 7.4–7.25 (m, 1H), 7.05 (m, 1H), 4.5–3.5 (m), 3.2–2.7 (m, 2H), 2.2–1.3 (m, 7H).

MS (ESI): 422.9 (calc.); 422.21 (obs.).

Ex. 353

¹H NMR (CD₃OD) δ: 9.39 (s, 2H), 9.04 (s, 2H), 8.21 (s, 1H), 8.08 (s, 1H), 8.03 (m, 1H), 7.88 (d, 1H, J=8.4 Hz), 7.76

(d, 1H, J=8.4 Hz), 7.61 (s, 1H), 7.15 (m, 4H), 3.25 (br. m, 2H), 2.85 (br.m, 2H), 2.61 (t, 2H, J=7.2 Hz0, 2.46 (br.m, 2H).

MS (LRMS) M+1: Calc: 505.11; Obs.: 506.06.

Ex.: 354

$^1$H NMR (DMSO-d$_6$) δ: 9.47 (s, 2H), 9.15 (s, 2H), 8.24 (s, 1H), 7.94–7.77 (m, 5H), 7.53–7.44 (m, 3H), 7.30 (d, 1H, J=8.1 Hz), 7.02 (t, 1H, J=8.1 Hz), 4.20 (t, 2H, J=5.7 Hz), 3.70 (m, 2H).

MS (ESI, M$^+$+1): Calc. 415.16; Found 416.2.

Ex. 355

$^1$H NMR (DMSO-d$_6$) δ: 9.49 (s, 2H), 9.17 (s, 2H), 8.25 (s, 1H), 7.94 (d, 1H, J=8.6 Hz), 7.82 (m, 2H), 7.25 (d, 1H, J=7.7 Hz), 7.04 (t, 1H, J=7.7 Hz), 4.06 (t, 2H, J=5.4 Hz), 3.46 (m, 2H), 2.30 (m, 4H).

MS (ESI, M$^+$+1): Calc. 410.17; Found 411.1.

Ex. 360

$^1$H-NMR (DMSO-d$_6$) δ: 9.35 (s, 2H), 8.94 (s, 2H), 8.19 (s, 1H), 7.86–7.70 (m, 3H), 7.17 (d, 1H, J=8.1 Hz), 6.98 (t, 1H, J=8.1 Hz), 4.63 (s, 2H), 3.82 (s, 2H), 1.39 (s, 9H).

MS (ESI, M$^+$+1): Calc. 439.19; Found 440.1.

Ex. 361

$^1$H-NMR (methanol-d$_4$) δ ppm: 9.55 (s, 0.5H), 9.10 (s, 0.5H), 8.35 (s, 1H), 8.09 (d, 1H), 8.00 (d, 1H), 7.71 (d, 1H), 7.52 (d, 1H), 7.20 (t, 1H), 4.1 (br.m, 1H), 4.41 (m, 1H), 4.22 (m, 1H), 4.1 (m, 1H), 3.50 (m, 2H), 3.35 (m, 1H), 2.07 (m, 5H).

MS (ESI): 409.18 (calc.), 410.0 (obs.).

Ex. 367

MS: 380.16 (calc.); 381.0 (obs.).

Ex. 368

$^1$H-NMR (methanol-d$_4$) δ ppm: 8.40 (s, 1H), 8.09 (d, 1H), 8.00 (m, 1H), 7.71 (d, 1H), 7.59 (d, 1H), 7.20 (t, 1H), 4.51 (m, 2H), 4.09 (m, 2H), 3.80 (m, 1H), 3.65 (m, 1H), 3.33 (m, 2H), 2.40–2.00 (m, 6H), 1.45–1.25 (In, 4H), 1.19 (m, 6H).

MS (ESI): 450.24 (calc.), 451.2 (obs.).

Ex. 371

$^1$H NMR (DMSO-d$_6$) δ: 9.47 (s, 2H), 9.16 (s, 2H), 8.24 (s, 1H), 7.92 (d, 1H, J=8.5 Hz), 7.78 (m, 2H), 7.23 (d, 1H, J=7.3 Hz), 7.01 (t, 1H, J=7.3 Hz), 4.06 (t, 2H, J=5.4 Hz), 3.50 (m, 2H), 2.64 (m, 2H), 2.50 (m. 2H).

MS (ESI, M$^+$+1): Calc. 392.16; Found 393.2.

Ex. 373

$^1$H NMR (DMSO-d$_6$) δ: 9.4 (br.s, 2H), 9.03 (br.s, 2H), 8.22 (s, 1H), 7.91–7.73 (m, 3H), 7.18 (d, 1H, J=8.1 Hz), 7.00 (t, 1H, j=8.1 Hz), 4.57 (s, 2H), 3.18 (t, 2H, J=7.2 hz), 1.55 (m, 1H), 1.35 (m, 2H), 0.86 (d, 6H, J=6.6 hz).

MS: 395.2 (calc.); 396.1 (obs.).

Ex. 374

$^1$H NMR (DMSO-d$_6$) δ: 9.45 (s, 2H), 9.11 (s, 2H), 8.24 (s, 1H), 7.93–7.76 (m, 5H), 7.62–7.57 (m, 3H), 7.11 (d, 1H, J=8.1 Hz), 6.98 (t, 1H, J=8.1 Hz), 4.03 (t, 2H, J=5.4 Hz), 3.18 (t, 2H, J=5.4 Hz).

MS (ESI, M$^+$+1): Calc. 451.13; Found 452.1.

Ex. 378

$^1$H-NMR (methanol-d$_4$) δ ppm: 9.6 (s, 2H), 9.09 (s, 1H), 8.36 (s, 1H), 8.18 (d, 1H, J=8 Hz), 8.00 (d, 1H, J=8 Hz), 7.70 (d, 1H, J=8 Hz), 7.57 (d, 1H, 8 Hz), 7.16 (t, 1H, J=8 Hz), 4.55 (m, 1H), 4.43 (dd, 1H), 4.07 (t, 1H), 3.70–3.40 (m, 2H), 3.24 (m, 1H), 2.80 (t, 2H), 2.3–2.0 (m, 5H).

MS (ESI): 422.21 (calc.), 423.1 (obs.).

Ex. 380

$^1$H-NMR (DMSO-d$_6$) δ: 9.40 (s, 2H), 9.06 (s, 2H), 8.20 (s, 1H), 7.87–7.72 (m, 3H), 7.53–7.19 (m, 5H), 6.97 (t, 1H, J=7.9 Hz), 4.27 (t, 2H, J=7.1 Hz), 3.21 (t, 2H, J=7.1 Hz).

MS (ESI, M$^+$+1): Calc. 406.12; Found 407.0.

Ex. 383

$^1$H NMR (DMSO-d$_6$) δ: 9.41 (s, 2H), 9.06 (s, 2H), 8.21 (s, 1H), 7.88 (d, 1H, J=8.4 Hz), 7.77 (m, 2H), 7.21 (d, 1H, J=7.8 Hz), 7.00 (t, 1H, J=7.8 Hz), 4.22 (dd, 1H, J=7.1, 4.2), 4.06 (t, 2H, J=5.5 Hz), 3.47 (t, 1H, J=5.5 Hz) 2.56 (m, 2H).

MS (ESI, M$^+$+1): Calc. 451.16; Found 452.3.

Ex. 384

$^1$H NMR (DMSO-d$_6$) δ: 9.45 (br.s, 2H), 9.11 (br.s, 2H), 8.24 (s, 1H), 7.94–7.76 (m, 3H), 7.35–7.22 (m, 6H), 7.03 (t, 1H, J=8.1 Hz), 4.68 (s, 2H), 4.40 (s, 2H).

MS: 415.169 calc.); 416.1 (obs.).

Ex. 385

$^1$H NMR (DMSO-d$_6$) δ: 9.51 (s, 1H), 9.29 (br.s, 2H), 9.03 (br.s, 2H), 8.18 (s, 1H), 8.02 (s, 1H), 7.83 (d, 1H, J=7 Hz), 7.70 (d, 1H, J=7 Hz), 7.25 (dd, 1H) 7.09 (d, 1H, J=7 Hz), 2.96 (s, 3H).

MS: 345.09 (calc.); 345.9 (obs.).

Ex. 386

$^1$H NMR (DMSO-d$_6$) δ: 9.46 (s, 2H), 9.23 (s, 1H), 9.14 (s, 2H), 8.88 (d, 1H, J=5.3 Hz), 8.67 (d, 1H, J=8.0 Hz), 8.23 (s, 1H), 7.92–7.76 (m, 4H), 7.28 (d, 1H, J=8.0 Hz), 7.01 (t, 1H, J=8.0 Hz), 4.23 (t, 2H, J=5.5 Hz), 3.74 (m, 2H).

MS (ESI, M$^+$+1): Calc. 416.16; Found 417.1.

Ex. 387

2-(3'-Amino-5-chloro-2-hydroxy-biphenyl-3-yl)-3H-benzoimidazole-5-carboxamidine $^1$H-NMR (DMSO-d$_6$) δ ppm: 10.40 (br s, 2H), 9.44 (s, 2H), 9.12 (s, 2H), 8.43 (s, 1H), 8.25 (s, 1H), 7.90 (d, 1H, J=7.6 Hz), 7.77 (d, 1H, J=8.1 Hz), 7.70 (s, 1H), 7.65 (d, 1H, J=7.8 Hz), 7.57 (t, 1H, J=7.9 Hz), 7.55 (s, 1H), 7.38 (d, 1H, J=7.4 Hz).

MS (CI): Calc. 377.1, Found 378.6.

Ex. 388

$^1$H-NMR (DMSO-d$_6$) δ ppm: 9.88 (s, 1H), 9.42 (s, 2H), 9.11 (s, 2H), 8.38 (s, 1H), 8.24 (s, 1H), 7.90 (d, 1H, J=8.3 Hz), 7.77 (d, 1H, J=8.4 Hz), 7.50–7.30 (m, 4H), 7.23 (d, 1H, J=7.5 Hz), 3.05 (s, 3H).

MS (ESI, M+1): Calc. 455.1, Found 456.0.

Ex. 389

$^1$H-NMR (DMSO-d$_6$) δ ppm: 9.41 (s, 2H), 9.09 (s, 2H), 8.23 (s, 1H), 8.15 (s, 1H), 7.87 (d, 1H, J=8.43 Hz), 7.74 (d, 1H, J=8.43 Hz), 7.66 (s, 1H), 2.84 (t, 2H, J=7.4 Hz), 2.63 (t, 2H, J=7.4 Hz).

MS (ESI, M+1): Calc. 402.03, Found 403.1.

Ex. 393

2-[3-(1-Aminoacetyl-pyrrolidin-2-ylmethoxy)-2-hydroxy-phenyl]-3H-benzoaindazole-5-carboxamidine MS: 408.19 (calc.); 409.0 (obs.).

Ex.: 394

$^1$H NMR (DMSO-d$_6$) δ: 9.45 (2H, br.s), 9.14 (2H, br.s), 8.25 (1H, s), 7.94–7.77 (3H, m), 7.22 (1H, d, J=8.0 Hz), 7.02 (1H, s, J=8.0 Hz), 4.62 (2H, s), 3.87–3.56 (4H, m), 3.24 (2H, m), 1.80 (2H, m), 1.50 (1H, m).

MS(ES): Calc.: 409.18; Obs.: 410.0.

Ex. 395

$^1$H NMR (DMSO-d$_6$) δ: 9.48 (br.s, 2H), 9.18 (br.s, 2H), 8.25 (s, 1H), 7.95–7.77 (m, 3H), 7.11 (d, 1H, J=8.1 hz), 7.00 (t, 1H, J=8.1 Hz), 4.82 9s, 2H).

MS: 326.10 (calc.) 326.8 (obs.).

Ex. 396

$^1$H NMR (DMSO-d$_6$) δ: 10.15 (s, 1H); 10.05 (s, 1H); 9.5 (s, 2H); 9.2 (s, 2H); 8.6 (d, 1H); 8.3 (s, 1H); 7.9 (d, 1H); 7.8 (d, 1H); 7.3 (t, 1H); 4.19 (s, 2H); 3.5 (t, 2H); 3.05 (t, 2H).

MS: 373.17 (calc); 374.5 (obs.).

Ex. 398

$^1$H NMR (DMSO-d$_6$) δ: 9.45 (s, 2H), 9.1 (s, 2H), 8.45 (d, 1H); 8.25 (s, 1H); 8.23 (d, 1H); 7.85 (s, 3H); 7.83 (d, 1H); 7.8 (d, 1H); 7.3 (t, 1H); 4.75 (s, 2H); 3.8 (t, 2H); 2.9 (t, 2H).

MS: 415.19 (calc.); 416.1 (obs.).

Ex. 399

$^1$H-NMR (methanol-d$_4$) d ppm: 8.36 (s, 1H), 8.07 (d, 1H, J=8 Hz), 7.98 (d, 1H, J=8 Hz), 7.70 (d, 1H, J=8 Hz), 7.52 (1H, d, J=8 Hz), 7.16 (t, 1H, J=8 Hz), 4.58 (p, 1H), 4.36 (m, 1H), 4.20–4.10 (m, 2H), 3.80–3.60 (m, 2H), 3.30 (m, 1H), 2.40–2.00 (m, 6H), 1.41 (d, 1H), 1.32 (s, 1H), 1.13 (d, 3H), 1.03 (d, 3H).

MS (ESI): 450.24 (calc.), 451.2 (obs.).

Ex. 400

$^1$H NMR (CD$_3$OD) δ: 9.40 (s, 2H), 9.05 (s, 2H), 8.30 (br.s, 2H), 7.90–7.70 (m, 4H), 7.21 (d, 1H, J=7 Hz), 7.15–6.50 (t, 1H, J=7 Hz), 4.40 (m, 1H), 4.20–4.07 (m, 2H), 4.07–3.95 (m, 1H), 3.75–3.60 (m, 1H), 3.60–3.25 (m, 6H), 2.10–180 (m, 6H), 0.95 (t, 3H), 0.85 (t, 3H).

MS (ESI): Calc.: 450.24; Obs.: 451.1.

Ex. 401

MS (ES): 430.19 (calc.); 429.0 (obs.).

Ex. 402

MS (ES): Calc.: 444.2; Obs.: 444.9.

Ex. 403

MS: 426.2 (calc.); 427.0 (obs.).

Ex. 405

$^1$H-NMR (DMSO-d$_6$) δ: 9.38 (s, 2H), 9.03 (s, 2H), 8.20 (s, 1H), 7.88–7.75 (m, 4H), 7.45–6.99 (m, 10H), 4.04 (t, 2H, J=5.5 Hz), 3.44 (m, 2H).

MS (ESI, M$^+$+1): Calc. 506.21; Found 507.2.

Ex. 406

$^1$H NMR (DMSO-d$_6$) δ: 9.58 (s, 2H), 9.29 (s, 2H), 8.29 (s, 1H), 7.98 (d, 1H, J=9.1 Hz), 7.86 (m, 2H), 7.27 (d, 1H, J=7.8 Hz), 7.04 (t, 1H, J=7.8 Hz), 4.09 (t, 2H, J=5.5 Hz), 3.84 (s, 2H), 3.57 (m, 2H) 3.30 (s, 3H).

MS (ESI, M$^+$+1): Calc. 383.16; Found 384.0.

Ex. 423

$^1$H NMR (DMSO-d$_6$) δ: 9.42 (s, 2H), 9.10 (s, 2H), 8.22 (s, 1H), 7.90–7–74 (m, 3H), 7.20 (d, 1H, J=7.8 Hz), 7.00 (t, 1H, J=7.8 Hz), 4.06 (m, 2H), 3.50 (m, 4H), 1.35 (s, 9H).

MS (ESI, M$^+$+1): Calc. 468.21; Found 469.2.

Ex. 424

$^1$H NMR (DMSO-d$_6$) δ: 9.43 (s, 2H), 9.10 (s, 2H), 8.22 (s, 1H), 7.89 (d, 1H, J=8.5 Hz), 7.81–7.75 (m, 2H), 7.30–7.18 (m, 6H), 7.00 (t, 1H, J=8.1 Hz), 4.22 (s, 2H), 4.05 (t, 2H, J=5.5 Hz), 3.43 (t, 2H, J=5.5 Hz).

MS (ESI, M$^+$+1): Calc. 444.19; Found 445.2.

Ex. 425

$^1$H NMR (DMSO-d$_6$) δ: 9.36 (s, 2H), 9.07 (s, 2H), 8.72 (m, 1H), 8.19 (s, 1H), 7.84 (d, 1H, J=8.6 Hz), 7.76 (m, 2H), 7.18 (d, 1H, J=8.1 Hz), 6.98 (t, 1H, J=8.1 Hz), 4.10 (t, 2H, J=5.4), 3.57 (m, 4H).

MS (ESI, M$^+$+1): Calc. 368.16; Found 369.0.

Ex. 426

$^1$H NMR (DMSO-d$_6$) δ: 9.45 (s, 2H), 9.13 (s, 2H), 8.24 (s, 1H), 7.91 (d, 1H, J=8.5 Hz), 7.83 (m, 2H), 7.27–7.20 (m, 6H), 7.00 (t, 1H, J=8.1 Hz), 4.08 (t, 2H, J=5.6 Hz), 3.48 (m, 2H), 3.46 (s, 2H).

MS (ESI, M$^+$+1): Calc. 429.18; Found 430.1.

Ex. 427

$^1$H NMR (DMSO-d$_6$) δ: 9.46 (s, 2H), 9.15 (s, 2H), 8.24 (s, 1H), 7.90 (d, 1H, J=8.5 Hz), 7.80 (m, 2H), 7.24–7.12 (m, 6H), 7.00 (t, 1H, J=8.0 Hz), 4.02 (t, 2H, J=5.6 Hz), 3.46 (m, 2H), 2.82 (t, 2H, J=7.3 Hz), 2.41 (t, 2H, J=7.3 Hz).

MS (ESI, M$^+$+1): Calc. 443.20; Found 444.1.

Ex. 428

$^1$H NMR (DMSO-d$_6$) δ: 9.41 (s, 2H), 9.08 (s, 2H), 8.22 (s, 1H), 7.88–7.73 (m, 3H), 7.50 (m, 3H), 7.32 (m, 1H), 7.24 (d, 1H, J=8.0 Hz), 6.98 (t, 1H, J=8.0 Hz), 5.26 (s, 2H).

MS (ESI, M$^+$+1): Calc. 373.15; Found 374.0.

Synthesis of Indole Based Compounds of Formula I

Procedures LI through LXI discuss the synthesis of precursors useful in synthesizing indole based compounds of Formula I. These indole based compounds of Formula I can be structurally represented as follows.

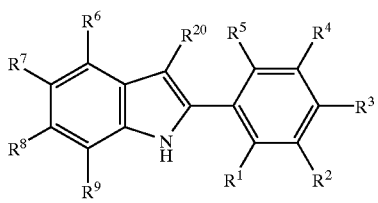

wherein $R^1$, $R^2$, $R^3$, $R^4$, $R^5$, $R^6$, $R^7$, $R^8$, $R^9$ and $R^{20}$ are as described in the detailed description.

Compounds of Formula I having the indole nucleus can be synthesized by using commercially available ketones or carboxylic acids, for example compounds 210 to 237, and aldehyde compounds 240(a) to 240(e) which can be prepared by schemes LI through LXI. discussed below.

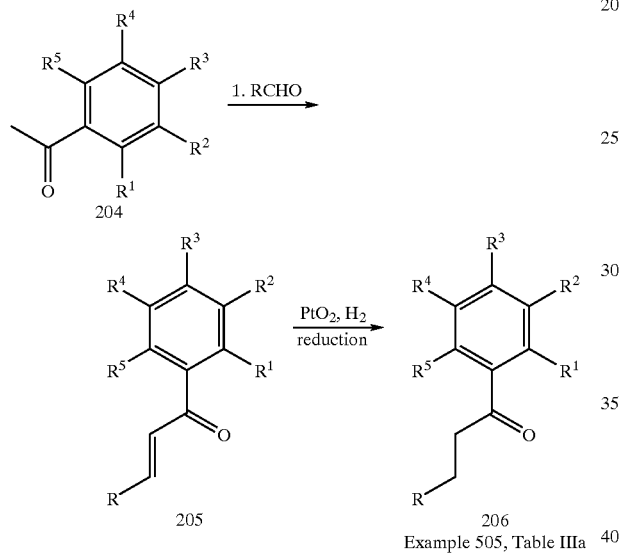

Scheme LI illustrates the general procedure for condensation of acetophenones and substituted aromatic aldehydes, wherein $R^1$, $R^2$, $R^3$, $R^4$ and $R^5$ are as described in the detailed description section above.

Compounds of Formula 201 wherein $R^{20}$ is $CH_2R$ can be prepared by methods illustrated by Scheme LI. For example compound 204 wherein $R^1$ is hydrogen, $R^2$ and $R^4$ are fluoro and $R^3$ is hydrogen, i.e., 1-(3,5-difluoro-2-hydroxyphenyl) ethanone 204 (6.3 mmol) and benzaldehyde (7.56 mmol) are mixed in ethanol (20 mL) and aqueous barium hydroxide (2 gm in 15 mL water) (aqueous NaOH (10%) may be substituted for barium hydroxide) is added. The mixture is stirred for 12–18 h at 60° (reaction times can vary between 3 h to 18 h). The mixture was filtered and the solids which were collected were washed with water (30 mL) and ether (20 mL). The solids are taken up in 1N HCl (30 mL) and the solution extracted with ethyl acetate. The organic extracts are washed with water, brine and dried ($MgSO_4$) to afford 1-(3,5-difluoro-2-hydroxyphenyl)-3-propenone the title compound 205 as a yellow-brown solid in a 70% yield.

1-(3,5-difluoro-2-hydroxyphenyl)-3-propenone 205 was catalytically hydrogenated using $PtO_2$—C (10%) as a catalyst (can substitute Pd—C or $Pd(OH)_2$ as catalysts) and ethyl acetate as a solvent for 15 min (or until reduction is completed). The catalyst was filtered off and the filtrate was evaporated to yield 1-(3,5-difluoro-2-hydroxyphenyl)-3-propan-1-one 206 (Example 505, Table IIIa).

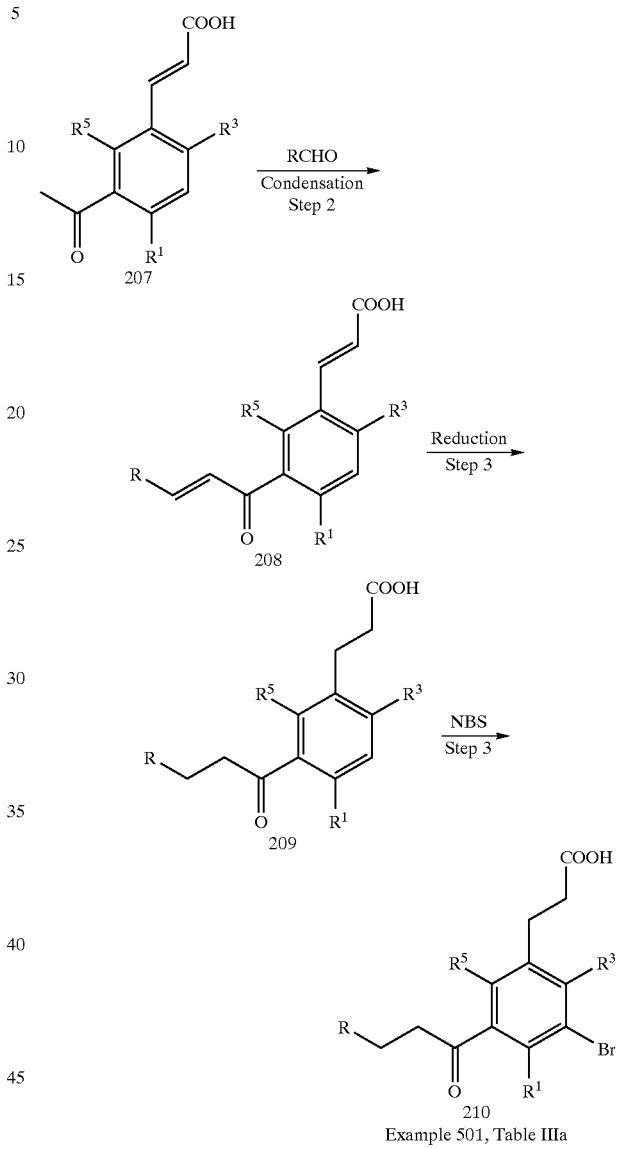

Scheme LII illustrates synthesis of ketones 210, wherein $R^1$, $R^2$, $R^3$, and $R^5$ are as defined in the detailed description section above.

For example 1-(5-bromo-2-hydroxy phenyl)ethanone 206 (6.6 g, 30.7 mmol), methyl acrylate (4.17 mL, 46 mmol), triphenyl phosphine (2.43 g, 9 mmol), palladium acetate (1.03 g, 4.6 mmol), and triethyl amine (6.07 g, 60 mmol) were combined with benzene (100 mL) and refluxed over 18 h. The reaction mixture is cooled to room temperature, diluted with 0.05 N HCl (100 mL) and extracted with ethyl acetate. The organic layer is separated and further washed with water and then brine solution. The organic layer is dried ($MgSO_4$), and concentrated to yield an oily residue. Purification of this residue by column chromatography (10:1.5, hexanes:ethyl acetate) afforded 5-(2-carboxy vinyl-2-hydroxy)benzoic acid 207 as a yellow solid.

$^1$H NMR ($CDCl_3$, 300 MHz) *: 12.22 (s, 1H), 8.23 (s, 1H), 7.94 (d, 1H, J=8.7 Hz), 7.67 (d, 1H, J=16 Hz), 7.0 (d, 1H, J=8.7 Hz), 6.8 (d, 1H, J=16 Hz).

5-(2-carboxy vinyl-2-hydroxy)benzoic acid 207 was converted to 3-[4-hydroxy-3-(3-phenyl-acryloyl)-phenyl]-acrylic acid as described by general condensation procedure in Scheme LI above, to yield 208.

$^1$H NMR (DMSO-$d_6$) δ: 12.81 (s, 1H), 8.54 (s, 1H), 8.12 (d, 1H, J=5.5 Hz), 7.91 (m, 4H), 7.67 (d, 1H, J=16.0 Hz), 7.49 (m, 3H), 7.04 (d, 1H, J=8.7 Hz), 6.57 (d, 1H, J=6.0 Hz).

MS(M$^+$): Calc.: 294.3; Obs.: 294.5.

3-[4-Hydroxy-3-(3-phenyl-acryloyl)-phenyl]-acrylic acid was converted to 3-[4-hydroxy-3-(3-phenyl-propionyl)-phenyl]-propionic acid 209 as described by general reduction procedure in Scheme LI.

General Procedure for Brominating at Position R$^2$

The carboxylic acid 209, for example 3-[4-Hydroxy-3-(3-phenyl-propionyl)-phenyl]-propionic acid, (1.04 gm, 3.4 g mmol) was dissolved in DMF (7 mL) and N-bromosuccinimide (0.65 g, 3.66 mmol) was added to the solution. The mixture was stirred at ambient temperature for 2.5 h, diluted with ether and the organic layer was separated and washed with water and brine and then filtered through a pad of magnesium sulfate and concentrated. The residue was purified by flash chromatography (3.5:1.5:0.1 of hexane:ethyl acetate:acetic acid) to give 0.5 g of 3-[3-bromo-4-hydroxy-5-(3-phenyl-propionyl)-phenyl]-propionic acid 210 as a yellow-brown oil.

$^1$H NMR (CDCl$_3$) δ: 7.61 9 (d, 1H, J=1.9 Hz), 7.54 (d, 1H, J=1.9 Hz), 7.27 (m, 5H), 3.33 (t, 2H, J=7.3 Hz), 3.06 (t, 2H, J=7.8 Hz), 2.86 (t, 2H, J=2,23 Hz), 2.64 (br.t, 2H).

LRMS M+1: Calc.: 376.03; Obs.: 377.9.

Scheme LIII illustrates the synthesis of ketones 212 to 216.

Preparation of 1-(5-chloromethyl-2-hydroxy-phenyl)-ethanone 211 was accomplished using the procedure of Florall, L; Ross, S. B et al., Acta Pharm. Suec, V 15, 1478, p 13–22.

1-(3-Bromo-5-chloromethyl-2-hydroxy-phenyl)-ethanone 212

A solution of N-bromosuccinimide (10 mmol) in 8 mL of DMF is added dropwise to a solution of 1-(5-chloromethyl-2-hydroxy-phenyl)-ethanone 211 (10 mmol) in 20 mL DMF and the resulting mixture is stirred for 12–18 h. The solvent is evaporated under reduced pressure and the residue is diluted with water resulting in the formation of a solid. The solid is isolated and recrystallized from ethanol to yield 1-(3-Bromo-5-chloromethyl-2-hydroxy-phenyl)-ethanone 212.

$^1$H NMR (CDCl$_3$) δ ppm: 2.68 (s, 3H), 4.55 (s, 2H), 7.72 (q, 1H, J=2.1 Hz), 7.78 (q, 1H, J=2.1 Hz), 13.02 (s, 1H).

MS: Found: 264; Calc.: 263.52.

(3-acetyl-5-bromo-4-hydroxy-phenyl)-acetonitrile 213 (Ex. 508)

A solution of 1-(3-Bromo-5-chloromethyl-2-hydroxy-phenyl)-ethanone 212 (7.6 mmol) in 6 mL DMSO is added dropwise to a suspension of 8.2 mmol of NaCN in 4 mL DMSO. The mixture is stirred for 12–18 h and diluted with 80 mL water to yield a solid. The solid is isolated and recrystallized from ethanol to yield (3-acetyl-5-bromo-4-hydroxy-phenyl)-acetonitrile 213 in a 58% yield.

Scheme LIII

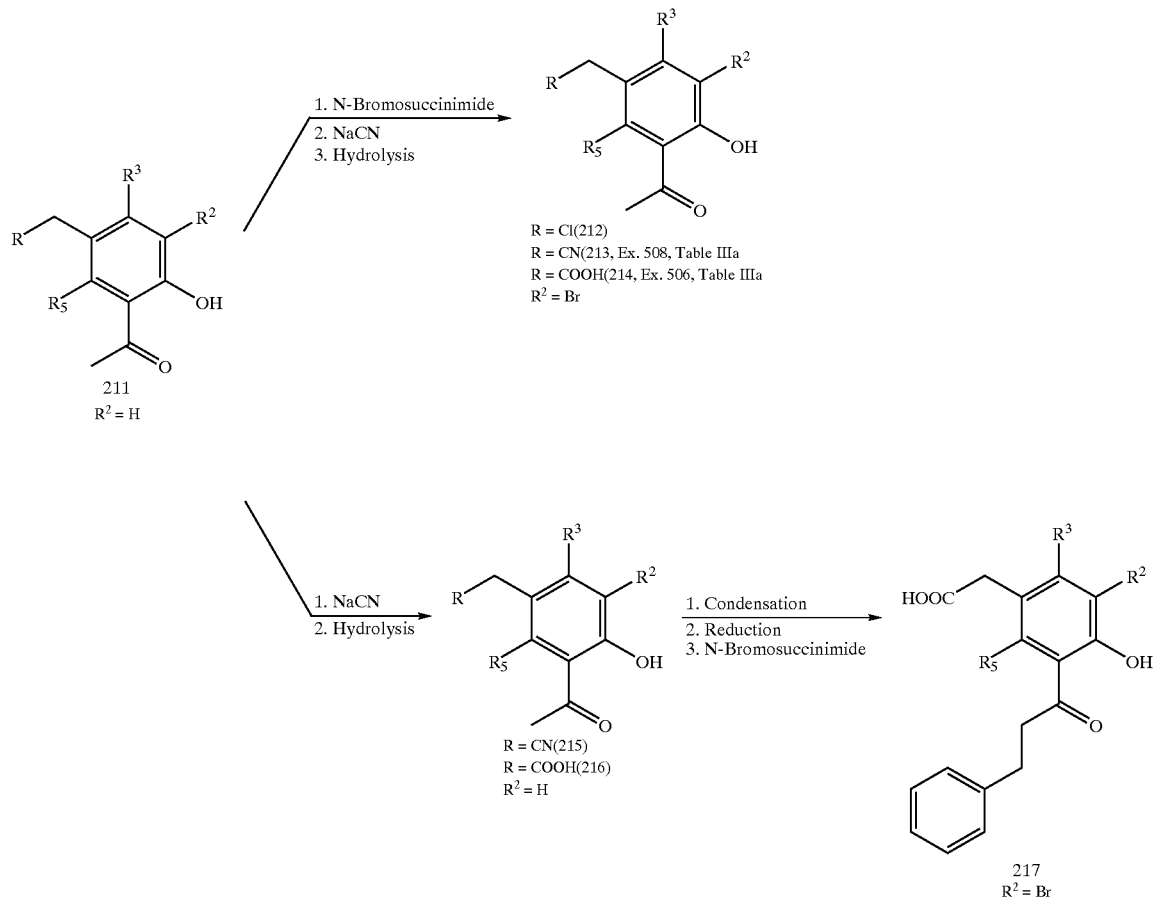

¹H NMR (CDCl₃) δ ppm: 2.7 (s, 3H), 3.81 (s, 2H), 7.75 (s, 2H), 13.03 (s, 1H).
MS: Calc.: 244.08; Found: 255.0.
(3-Acetyl-5-bromo-4-hydroxy-phenyl)-acetic acid 214 (Example 506, Table IIIa)

(3-acetyl-5-bromo-4-hydroxy-phenyl)-acetonitrile 213 (6 g, 23.6, mmol) is refluxed in a mixture of 50 mL acetic acid, 5 mL conc. H₂SO₄ and 5 mL water for about 2–3 h. This refluxed mixture is cooled to ambient temperature and poured onto ice forming a solid. The solid is isolated and recrystallized from a ethanol-water mixture to yield (3-acetyl-5-bromo-4-hydroxy-phenyl)-acetic acid 214 in a 47% yield.

¹H NMR (CDCl₃) δ ppm: 2.67 (s, 3H), 3.59 (s, 2H), 7.62 (d, 1H, J=1.9 Hz), 7.69 (d, 1H, J=1.9 Hz), 12.85 (s, 1H).
MS: Calc.: 273.08; Found: 274.0.

Synthesis of 215 and 216 can be accomplished by following the procedures outlined for 213 and 214 respectively.

Synthesis of 1-(3-acetyl-5-bromo-4-hydroxy-phenyl)-4-phenyl-butan-2-one 217 (Example 500, Table IIIa) is accomplished from 216 following steps 2, 3 and 4 in Scheme LII above.

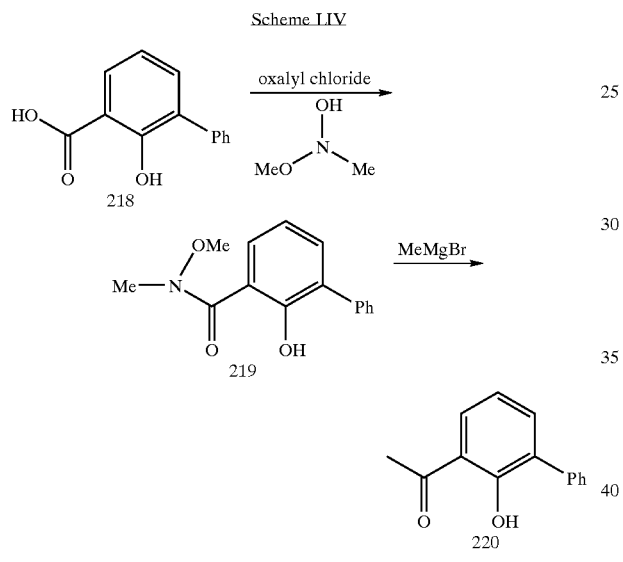

Scheme LIV illustrates synthesis of 220 which is useful in synthesizing compounds of Formula I.

219: 2-hydroxy-3-phenylbenzoic acid (218, 3.0 g, 14 mmol) is dissolved in EtOAc (50 ml) and a few drops of DMF are added. Oxalyl chloride (2.5 ml, 1.5 eq) is added and the reaction is stirred under a dry atmosphere for 1 h. The reaction mixture is then concentrated in vacuo to yield a mixture of clear oil and white solid. This mixture is diluted with CH₂Cl₂ (50 ml) followed by the addition of N,O-dimethyl hydroxylamine hydrochloride (1.5 g, 1.1 eq) and triethylamine (3.9 ml, 2 eq). This mixture is stirred for 12–18 h under a dry atmosphere. Dilution of the reaction mixture with EtOAc and subsequent washing with dilute HCl and brine, followed by drying (MgSO₄) and concentration in vacuo yields a mixture of reaction products. Flash chromatography (20/80 EtOAc/Hexanes) afforded N-methoxy-N-methyl-2-hydroxy-3-phenylbenzamide (219, 1.09 g) as a white solid.

¹H NMR (CDCl₃) δ: 11.42 (s, 1H) 7.94 (dd, 1H, J=1.7, 8.1 Hz) 7.61–7.58 (m, 1H) 7.48–7.36 (m, 6H) 6.93 (t, 1H, J=2.3, 3.4 Hz) 3.70 (s, 3H) 3.45 (s, 3H).

220

N-methoxy-N-methyl-2-hydroxy-3-phenylbenzamide (219, 2.37 g, 9.2 mmol) is dissolved in dry THF (40 ml) under nitrogen and cooled to 0° C. in an ice bath. MeMgBr (6.5 ml, 2.1 eq) is added and the resulting heterogeneous reaction is stirred for 1 h, THF (50 ml) is added to facilitate stirring, followed by excess MeMgBr. The reaction is then stirred for 3 days followed by quenching with dilute HCl. This mixture is then partitioned between ether and water. The organic phase is washed with brine, dried (MgSO₄) and concentrated in vacuo to yield a mixture of starting material (219) and product (220). Flash chromatography (EtOAc/Hexanes) affords 2-hydroxy-3-phenylacetophenone (220, 0.78 g) as a white solid.

EXAMPLE 522

Table IIIa:

Prepared according to literature procedure: Sipos, G.; Szalo, R. Acta Physica et Chemica, Vol. 7, 1961, pp. 126–128.

EXAMPLE 503

Table IIIa

NBS (240 mmol) is added to a methanol solution of 2'-hydroxy-1-benzyl acetophenone (10 mmol) at 0° C. The reaction is warmed to ambient temperature and stirred for 12 hours followed by dilution with water to yield a precipitate. The precipitate is isolated and dried under reduced pressure to yield 3.1 g of the title compound 503.

¹H NMR: (CDCl₃) δ ppm: 13.0 (s, 1H), 7.85 (s, 1H), 7.82 (s, 1H), 7.4–7.2 (m, 5H), 3.4 (t, 2H), 3.2 (t, 2H).

EXAMPLE 515

Table IIIa

The title compound 515 is prepared by bromination of 2'-hydroxy-1-methyl acetophenone using the procedure for 503, above.

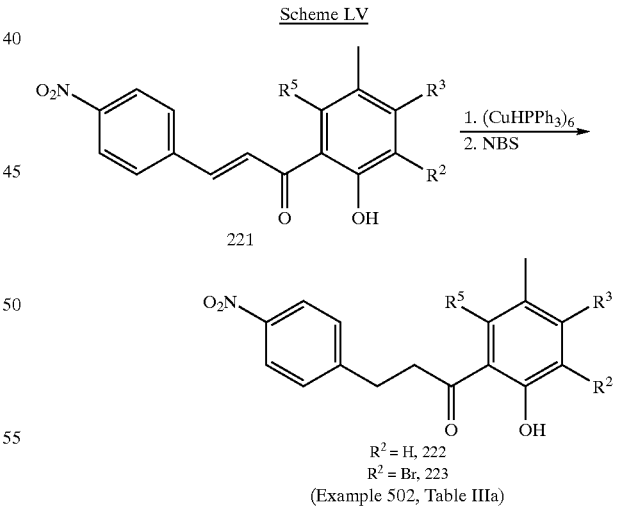

EXAMPLE 502

Table IIIa (Scheme LV)

221 is prepared by the condensation procedure described in Scheme LI above.

222 is prepared by the procedure discussed below:

In a 100 mL round bottom flask and under a nitrogen atmosphere, anhydrous benzene (20 mL) is added to 221

(2.5 g, 0.009 mol). To this solution is added (CuHPPh$_3$)$_6$ (7.0 g, 0.0035 mol). The reaction mixture is stirred at ambient temperature for 1 hr, stirred open to the atmosphere vigorously for 30 min, filtered through a pad of silica and eluted with 20% EtOAc/Hex. The filtrate is reduced and the residue purified by column chromatography on SiO$_2$ with 20%Et$_2$O/hex as the eluent to give 222 as a yellow solid: 1.4 g, 0.0049 mol, 55%. MS (ESI) Calc for C$_{16}$H$_{15}$NO$_4$: 285.10, Found: MH+ 286.0.

$^1$H NMR (300 MHz, DMSO-d$_6$) δ: 11.58 (s, 1H), 8.14 (d, 2H, J=7.6 Hz), 7.73 (s, 1H), 7.59 (d, 2H, J=7.6 Hz), 7.31 (d, 1H, J=9.3 Hz), 6.86 (d, 1H, J=9.3 Hz), 3.47 (t, 2H, J=8.3 Hz), 3.1 (t, 2H, J=8.3 Hz), 2.27 (s, 3 H).

The title compound 223, wherein R$^2$=Br, is prepared by brominating 222 by the procedure in Scheme LII above.

MS (ESI) Calc for C$_{16}$H$_{15}$NO$_4$Br: 363.03, Found: MH+ 363.6.

$^1$HNMR (300 MHz, DMSO) δ: 12.49 (s, 1H), 8.17 (d, 2H, J=9.4 Hz), 7.81 (s, 1H), 7.72 (s, 1H), 7.60 (d, 2H, J=9.4 Hz), 3.57 (t, 2H, J=8.2 Hz), 3.09 (t, 2H, J=8.2 Hz), 2.27 (s, 3H).

EXAMPLE 510

Table IIIa

General procedure for acetylation at the 2-position of phenols:

Scheme LVI

AC$_2$O (60 mmol) is slowly added to a solution of water (30 ml), NaOH (60 mmol) and the phenol (224, 50 mmol) at 0° C. The reaction mixture is stirred for 10 min and then extracted with diethyl ether. The ether layer is washed with water, dried (MgSO$_4$) and concentrated to yield 9.6 g of the aryl acetate 225.

$^1$H NMR: (CDCl$_3$) δ ppm: 7.26 (br.s, 1H), 7.08 (br.d, 1H, J=8.2 Hz), 7.02 (d, 1H, J=8.21 Hz), 2.38 (s, 3H), 2.37 (s, 3H).

The aryl acetate (225) and AlCL$_3$ (20 mmol each) were heated for 2 hours at 150° C. The reaction mixture is then diluted with HCl and water to yield the 226. The product is filtered and dried under reduced pressure.

$^1$H NMR: (CDCl$_3$) δ ppm: 12.7 (s, 1H), 7.47 (br.s, 1H), 7.42 (br.s, 1H), 2.65 (s, 3H), 2.35 (s, 3H).

EXAMPLE 521

Table IIIa

The title compound is prepared from 2'-hydroxy-3'-chloro acetophenone by alkylation with benzyl bromide using the procedure described for ex. 517, Table IIIa.

EXAMPLE 513

Table IIIa

The title compound is prepared from ex. 525 by alkylation with benzyl bromide using the procedure described for ex. 517, Table IIIa.

EXAMPLE 504

Table IIIa

The title compound is prepared from ex. 510 by alkylation with benzyl bromide using the procedure described for ex. 517, Table IIIa.

EXAMPLE 512

Table IIIa

The title compound is prepared from 4-cyano phenol as shown in Scheme LVII below:

Scheme LVII

Step 1 and 2 are as described in Scheme LVI above. Step 3 is as described in Scheme LII above.

229: $^1$H NMR: (CDCl$_3$) δ ppm: 7.7 (d, 2H, J=8.77 Hz), 7.3 (d, 4H, J=8.80 Hz).

230: $^1$H NMR: (CDCl$_3$) δ ppm: 12.7 (s, 1H), 8.15 (d, 1H, J=2.0 Hz), 7.78 (dd, 1H, J=8.74 Hz), 7.15 (d, 1H, J=8.66 Hz), 2.7 (s, 3H).

231: $^1$H NMR: (CDCl$_3$) δ ppm: 7.9 (br.s, 2H), 2.45 (s, 3H).

EXAMPLE 507

Table IIIa

N-chloro succinimide (NCS) (12 mmol) and 1-benzyl-2'-hydroxy acetophenone (10 mmol) are heated at 70° in methanol for two weeks. The mixture is then extracted with ether, and washed with water and concentrated to yield the title compound (1.8 g). The product is purified by flash chromatography on silica column using 1:3 diethyl ether-:hexanes mixture.

Scheme LVIII

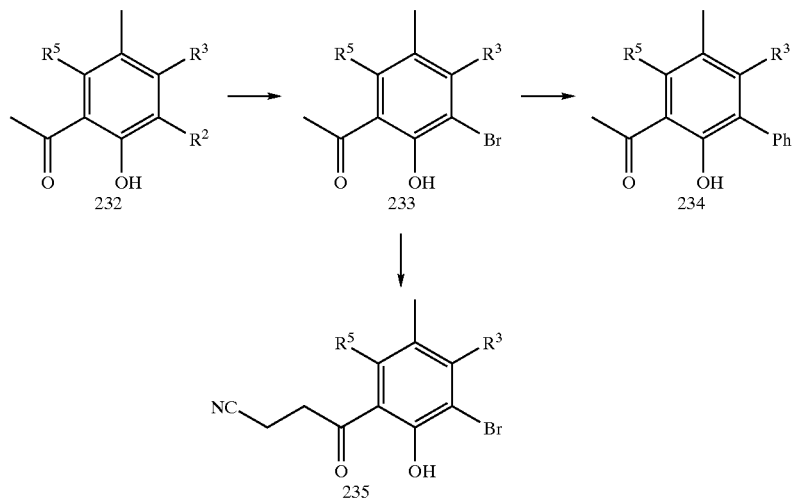

Scheme LVIII is a method that involves using a Suzuki coupling to generate substituted acetophenones (Example 519, Table IIIa).

The compound 2'-Hydroxy-3'-bromo-5'methylacetophenone 233 (Example 509, Table IIIa) is synthesized from the acetophenone using the bromination procedure in Scheme LII.

$^1$H NMR (DMSO-d$_6$) δ: 7.78 (d, 1H) 7.70 (d, 1H) 2.64 (s, 3 H) 2.26 (s, 3H).

2'-Hydroxy-3'-bromo-5'methylacetophenone 233 (0.46 g, 2 mmol) and phenylboronic acid (0.24 g, 1 eq.) are dissolved in DME (10 ml) and placed under a nitrogen atmosphere. Na$_2$CO$_3$ (0.50 g, 3 eq.) in water (10 ml) is added, followed by Pd(Ph$_3$)$_4$ (0.12 g, 0.05 eq.) and the reaction mixture heated to 75° C. for 12–18 h. Most of the DME is removed in vacuo and the reaction mixture is diluted with ether, washed with water, brine, and dried (MgSO4), and concentrated in vacuo to give an oil. Purification by flash chromatography (5/95 EtOAc/hexanes) afforded 2'-Hydroxy-3'-phenyl-5'methylacetophenone 234 as a yellow solid (0.32 g, 71% yield) (Example 519, Table IIIa).

$^1$H NMR (DMSO-d$_6$) δ: 7.79 (d, 1H) 7.53 (dd, 2H) 7.46–7.30 (m, 4H) 2.70 (s, 3H) 2.33 (s, 3H).

Alternatively 2'-Hydroxy-3'-bromo-5'methylacetophenone 233 can be treated as follows: LDA (20 mL, 1.5 M) is slowly added to a THF solution of 233 at about 0° and the reaction mixture is then cooled to about −78° followed by the addition of bromo acetonitrile (40 mmol). This resulting reaction mixture is stirred for 12–18 h at −78° and is then quenched with 1N HCl followed by extraction with ether. The ether layer is washed with water, dried (MgSO$_4$) and concentrated to yield an oil. This oil is purified by flash chromatography (4:1; hexanes:ethyl acetate) to yield 1 g of 235. (Example 517, Table IIIa)

$^1$H NMR (CDCl$_3$) δ ppm: 12.3 (s, 1H), 7.65 (s, 1H), 7.5 9s, 1H), 3.45 (t, 2H, J=7.14 Hz), 2.8 (t, 2H, J=7.3 Hz), 2.33 (s, 3H).

Scheme LVIX

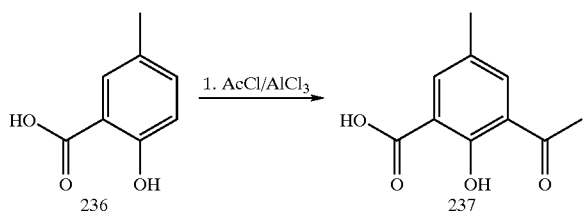

Acetyl chloride (14.7 ml, 5 eq.) is added slowly to an ice cooled suspension of AlCl$_3$ (27.7 g, 5 eq.) in dry CH$_2$Cl$_2$ (125 ml). The reaction is stirred until most of the solid is dissolved, then 5-methyl salicylic acid 236 (6.31 g, 41 mmol) is added. The reaction is stirred at 0° C. for 1.5 hr, then at room temperature for 1.5 hr. The reaction is poured onto ice, diluted with Et$_2$O, and washed with water, brine, dried (MgSO4). Concentration in vacuo afforded a slowly crystallizing oil. Recrystallization (CH$_2$Cl$_2$/hexanes) yielded pure 3-Acetyl-5-methyl salicylic acid (Example 529, Table IIIa) as 3.29 g of off white powder (41% recrystallized yield).

$^1$H NMR (CDCL$_3$) δ: 8.22 (d, J=1.88, 1H) 7.80 (d, J=1.98, 1H).

Aldehyde compounds useful in the synthesis of Indole based compounds of Formula I are commercially acailable. They can also be prepared by schemes LX(1) to LX(5) outlined below.

Scheme LX(1)

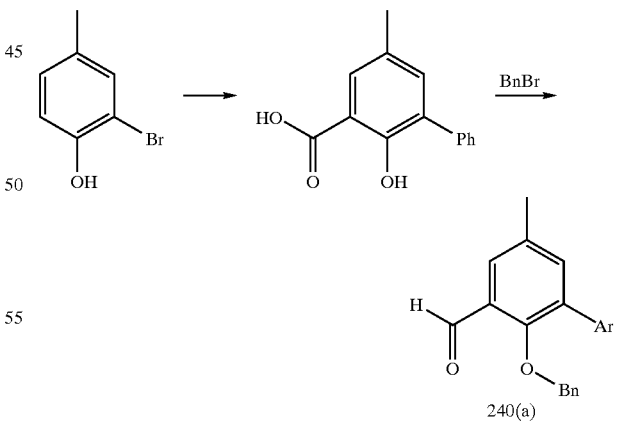

2-Hydroxy-5-methyl-biphenyl-3-carbaldehyde 240(a)

The above compound is prepared as outlined and discussed below:

3-Bromo-2-hydroxy-5-mothylbenzaldehyde.

A mixture of 2-bromo-4-methylphenol (5.0 g, 27 mmoles), chloroform (50 ml), water (10 ml) and NaOH (10 g) was refluxed for 3 hrs. The reaction mixture was cooled to ambient temperature, and then was acidified to pH=2 with conc. HCl, diluted with ether (300 ml) and washed with 1N HCl (200 ml). The organic layer was dried (MgSO4), filtered and concentrated to yield a residue which was purified using flash chromatography (10% ethyl acetate/hexanes) to yield 2.94 g (51%) of the title compound as a light yellow solid.

2-Hydroxy-5-methyl-biphenyl-3-carbaldehyde

A mixture of 3-bromo-2-hydroxy-5-methylbenzaldehyde (0.30 g, 1.40 mmoles), phenyl boronic acid (0.20 g, 1.67 mmoles) and tetrakis(triphenylphosphine)palladium(0) (81 mg, 0.07 mmoles) in toluene (10 ml) and 2M $K_2CO_3$ (3 ml) was heated to 80° C. for 2 hr. The reaction mixture was cooled to ambient temperature, diluted with ether (100 ml) and washed with $NaHCO_3$. The organic layer was dried (MgSO4), filtered and concentrated to yield a residue which was purified using flash chromatography (10% ethyl acetate/ hexanes) to yield 0.15 g (49%) of the title compound as a yellow oil.

The yellow oil then was treated with Benzyl bromide analogous to the procedure in Scheme VII above to yield the corresponding benzyl protected aldehyde.

Compounds analogous to 240(a) with different substituents can be prepared by following the procedure in Scheme LX(1) above.

Scheme LX(2)

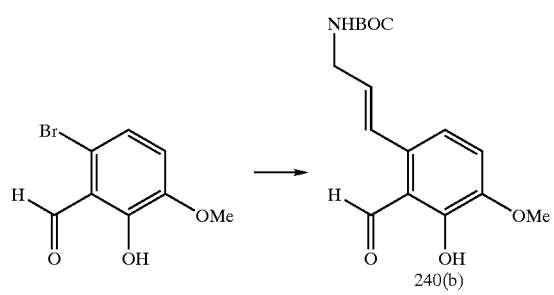

[3-(2-Formyl-3-hydroxy-4-methoxyphenyl)-prop-2-ynyl]-carbamic acid tert-butyl ester. 240(b)

A solution of 6-bromo-2-hydroxy-3-methoxybenzaldehyde (0.60 g, 2.6 mmoles) and prop-2-ynylcarbamic acid tert-butyl ester (0.44, 2.9 mmoles) in triethylamine (10 ml) was mixed with tetrakis(triphenylphosphine)palladium(0) (60 mg, 0.05 mmoles) and copper iodide (15 mg, 0.08 mmoles). The reaction mixture was refluxed for 30 minutes, cololed to ambient temperature, diluted (ethyl acetate 200 ml) and washed with 0.5N HCl (50 ml). The organic layer was dried (MgSO4), filtered and concentrated to yield a residue which was purified by flash chromatography (30% ethyl acetate/ hexanes) to yield 0.36 g (46%) of the title compound.

Compounds analogous to 240(b) with different substituents can be prepared by following the procedure in Scheme LX(2) above.

Scheme LX(3)

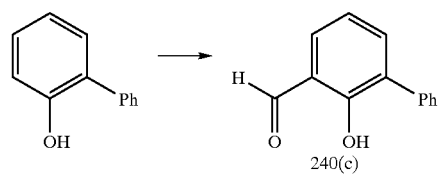

2-Hydroxy-biphenyl-3-carbaldehyde 240(c)

A solution of 2-Phenylphenol (300 mmol, 51 gr) and THF (400 mL) was mixed with triethylamine (3.5 eq, 145 ml) and magnesium dichloride (1.5 eq, 43 gm.). The preceeding mixture then was mixed with paraformaldehyde (6.0 eq, 54 gr) in portions over 10 min. to avoid vigorous exotherm forming a yellow mixtue. The yellow mixture then was refluxed gently for 1.5 hours. A Thin Layer Chromatography (TLC) indicated a clean conversion to the more hydrophobic desired product ($R_f$=0.44, 20% EtOAc/Hexane) and complete comsumption of the starting phenol. The reaction mixture was cooled in an ice bath and then diluted with 3N HCl to adjust the pH to about 5. The acidified mixture then was extracted with ether or ethyl acetate, the combined organic layers were washed with water, brine, and dried ($Na_2SO_4$). The dried organic phase was concentrated to yield the title compound as an oil (54.6 gm., 92%).

HPLC , 254 nm, r.t.=8.8 min, 1–90% $MeCN/H_2O$, 0.05%TFA) NMR (300 Mhz, $^1H$ $CDCl_3$): δ 11.6 ppm (s, 1H), 10.0 (s, 1H), 7.7 to 6.9 (m, 7H).

Compounds analogous to 240(c) with different substituents can be prepared by following the procedure in Scheme LX(3) above.

Scheme LX(4)

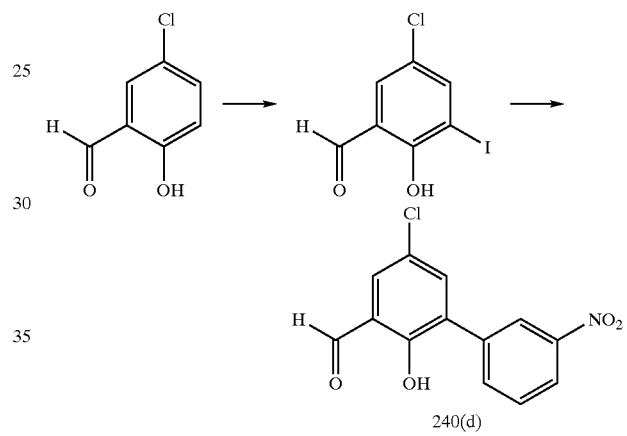

The aldehyde 240(d) was prepared using the procedure outlined in Scheme X above. Compounds analogous to 240(d) with different substituents can be prepared by following the procedure in Scheme LX(4) above.

Scheme LX(5)

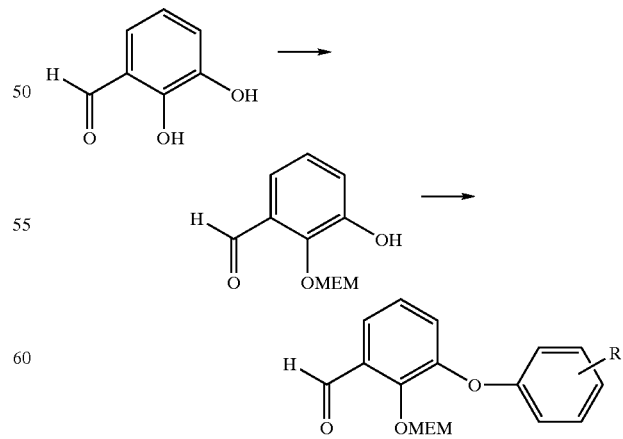

The 2,3-dihydroxy-benzaldehyde was treated with sodium hydride and MEM-chloride under conditions analogous to the benzylation procedure in Scheme VII to yield 250 mg, 1.1 mmol of the protected alcohol, which then was mixed with a DMF solution of Morpholino 4-chloro-3-nitro-benzenesulfoanmide (306 mg, 1 mmol) and the resulting mixture was heated for about 8–12 hours at about 80° C. The reaction mixture then was cooled to ambient temperature, diluted with ethyl actetae and washed with saturdated sodium hydrogen carbonate (2x) followed by brine (1x). The combined organic layers were dried over sodium sulfate, filtered and concentrated to yield a crude oily mixture. The crude was purfied by passing through over silica gel eluting with 30% ethyl acetate in hexanes to give the product (120 mg) 24%.

Compounds analogous to 240(e) with different substituents can be prepared by following the procedure in Scheme LX(5) above.

Table IIIa lists ketones, that can be used as precursors to make compounds of Formula I, as illustrated in Scheme LXII for the general Fischer-Indole synthesis below. It should be noted that $R^{20a}$ generally comprises an extra methylene group than $R^{20}$, thus one can represent $R^{20a}$ as $CH_2$—$R^{20}$.

TABLE IIIa

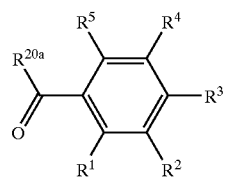

where $R^1$ represents OH, and $R^5$ represents H.

| EX. No. | Scheme | $R^2$ | $R^3$ | $R^4$ | $R^{20a}$ |
|---|---|---|---|---|---|
| 500 | LIII | Br | H | $CH_2COOH$ | $CH_2CH_2Ph$ |
| 501 | LII | Br | H | $CH_2CH_2COOH$ | $CH_2CH_2Ph$ |
| 502 | LV | Br | H | $CH_3$ | $CH_2CH_2$(p-nitro) Ph |
| 503 |  | Br | H | Br | $CH_2CH_2Ph$ |
| 504 | LVI | Cl | H | $CH_3$ | $CH_2CH_2Ph$ |
| 505 | LI | F | H | F | $CH_2CH_2Ph$ |
| 506 | LIII | Br | H | $CH_2COOH$ | $CH_3$ |
| 507 |  | H | H | Cl | $CH_2CH_2Ph$ |
| 508 | LIII | Br | H | $CH_2CN$ | $CH_3$ |
| 509 | LVII | Br | H | $CH_3$ | $CH_3$ |
| 510 | LVI | Cl | H | $CH_3$ | $CH_3$ |
| 511 | comm | Cl | H | Cl | $CH_3$ |
| 512 | LVII | Br | H | CN | $CH_3$ |
| 513 | LVII | $CH_3$ | H | $CH_3$ | $CH_2CH_2Ph$ |
| 514 | comm | F | H | F | H |
| 515 |  | Br | H | Br | $CH_2CH_3$ |
| 516 | LVII | 3-thio-phene | H | $CH_3$ | $CH_3$ |
| 517 | LVII | Br | H | $CH_3$ | $CH_2CH_2CN$ |
| 518 | comm | Br | H | Br | $CH_3$ |
| 519 | LVII | Ph | H | $CH_3$ | $CH_3$ |
| 520 | LIV | Ph | H | H | $CH_3$ |
| 521 | LVII | Cl | H | H | $CH_2CH_2Ph$ |
| 522 |  | Br | H | nitro | $CH_3$ |
| 523 | comm | H | H | H | $CH_2CH_2Ph$ |
| 524 | comm | H | H | Cl | $CH_3$ |
| 525 | LVI | $CH_3$ | H | $CH_3$ | $CH_3$ |
| 526 | LVII | p-toluyl | H | $CH_3$ | $CH_3$ |
| 527 | comm | H | H | Br | $CH_3$ |
| 528 | comm | H | H | $CH_3$ | $CH_3$ |
| 529 | LVIX | COOH | H | $CH_3$ | $CH_3$ |
| 530 | comm | H | H | H | $CH_3$ |
| 531 | comm | H | H | H | $CH_2CH_3$ |
| 532 | LVII | Br | H | $CH_3$ | $CH_2CH_2Ph$ |
| 533 | comm | Cl | H | Cl | $CH_3$ |
| 534 | LV | Br | H | Me | $CH_2CH_2$(m-nitro)Ph |
| 535 | comm | $OCH_2$—$R^3$ | $OCH_2$—$R^2$ | H | $CH_3$ |
| 535 | comm | Cl | H | H | $CH_3$ |

Synthesis of aryl hyrdazines which are useful in the preparation of indole based compounds of Formula I in the Fischer-Indole synthesis discussed below.

Most of the aryl hydrazines are prepared using the procedure of Castro et al., J. med. Chem., 1994, Vol. 37, No. 19, p 3030 from commercially available materials. In the case of the chloro substituted hydrazine used in the synthesis of Example 839, Table III the following scheme is used.

Scheme LXI

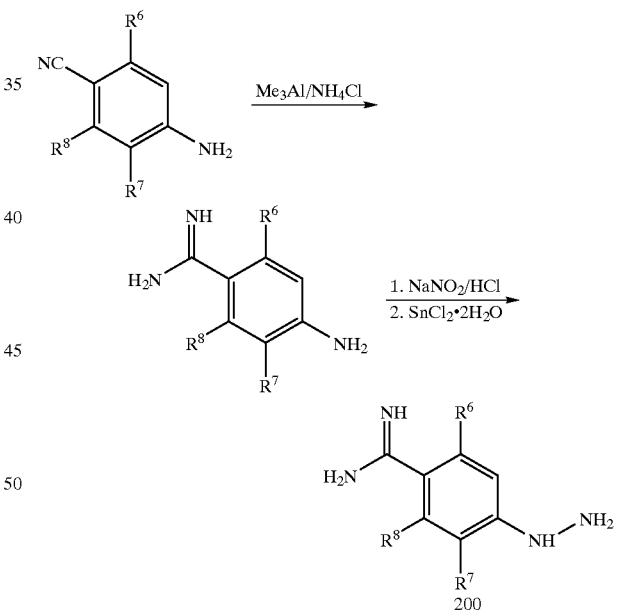

wherein $R^8$ is Cl; $R^6$ and $R^9$ are as defined in the detailed description.

To a p-xylenes solution of the nitrile 255 (0.5 g, 3.3 mmol) is added a freshly prepared solution of $Me_3Al/NH_4Cl$ (16 ml, 3 eq.). ($Me_3Al/NH_4Cl$ solution can be prepared by adding 5 g of ammonium chloride to p-xylenes (100 ml) at 0° C., then adding a 2M solution of trimethylaluminum in toluene (48 ml) over 10 min. This mixture is stirred for 12–18 h as it is warmed up to ambient temperature. This mixture is refluxed for 24 h, allowed to stand for 2 days and is then poured onto chloroform/silica gel. Filtration is followed by washing with 50% methanol/chloroform and then evaporation of the filtrates gives a yellow oil. Purification is performed using reverse phase HPLC to give the amidine. This compound is then subjected to the same general procedure as noted above for the preparation of hydrazines from anilines.

General Fisher-Indole Synthesis of Indoles in Table III

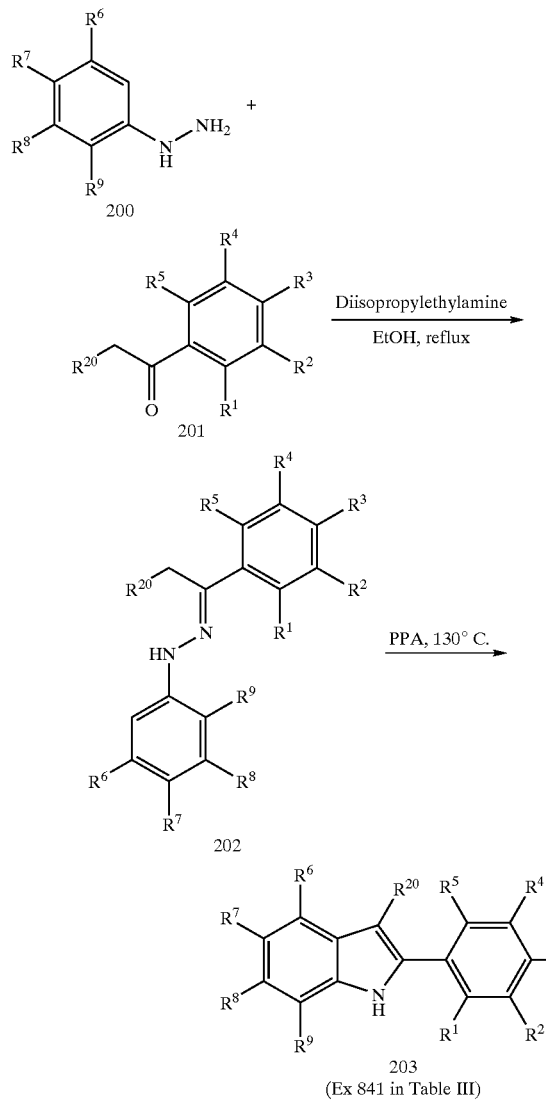

Compounds of Formula in which 'A' is optionally substituted 1H-indol-2-yl and 'B' is optionally substituted phenyl can be prepared by methods illustrated by Scheme LXII.

For example, a solution of 1-(3-bromo-2-hydroxy-5-methyl-phenyl)-3-(4-nitro-phenyl)-propan-1-one 201 (1.48 g, 0.004 mol), EtOH (30 mL), diisopropylethylamine (Hunigs base)(3 mL), and 4-Hydrazino-benzamidine 200 (0.93 g, 0.004 mol) is heated at reflux for 4 hr. (reaction times can vary between 2 h to 18 h). The solution is cooled to ambient temperature, filtered, washed with 6N HCl (2×25 mL), and dried for 12–18 h in a vacuum oven to give a 90% yield of 4-{N'-[1-(3-bromo-2-hydroxy-5-methyl-phenyl)-3-(4-nitro-phenyl)-propylidene]-hydrazino}-benzamidine 202 as an off-white solid (1.78 g, 0.0036 mol).

MS (ESI) Calc for $C_{23}H_{22}BrN_5O_3$: 495.1, Found: MH+ 496.1.

EXAMPLE 841

Table III

A mixture of 4-{N'-[1-(3-bromo-2-hydroxy-5-methyl-phenyl)-3-(4-nitro-phenyl)-propylidene]-hydrazino}-benzamidine 202 (0.30 g, 0.0006 mol) and PPA (5 mL) was heated at 130° C. (temperature may vary between 125–180° C.) for 30 min (reaction times may vary between 30 minutes–4 h). The reaction mixture was cooled to ambient temperature and cold $H_2O$ (5 mL) was added to produce a precipitate. The precipitate was washed and taken up in 9.1N HCl. Purification by reverse HPLC (0.01%HCl/acetonitrile) with a 2–90% gradient gave a 14% yield of 2-(3-bromo-2-hydroxy-5-methyl-phenyl)-3-(4-nitro-benzyl)-1H-indole-5-carboxamidine 203 as a white solid. (0.04 g, 0.08 mmol).

MS (ESI) Calc for $C_{23}H_{19}BrN_4O_3$: 478.08, Found: MH+ 479.4.

$^1$HNMR (300 MHz, DMSO-$d_6$) δ: 11.84 (s, 1H), 9.24 (s, 1H), 9.11 (s, 2H), 8.70 (s, 2H), 8.06 (d, 2H, J=7.6 Hz), 8.04 (s, 1H), 7.60–7.56 (m, 2H), 7.36 (s, 1H), 7.34 (d, 2H, J=7.6 Hz), 6.03 (s, 1H), 4.21 (s, 2H), 2.20 (s, 3H).

3-(4-amino-benzyl)-2-(3-bromo-2-hydroxy-5-methyl-phenyl)-1H-indole-5-carboxamidine (Example 803, Table III):

A mixture of 2-(3-bromo-2-hydroxy-5-methyl-phenyl)-3-(4-nitro-benzyl)-1H-indole-5-carboxamidine 203 (100 mgs, 0.2 mmol), $SnCl_2$ (100 mgs) and 6N HCl is heated at reflux for 1 hr. The reaction is cooled, let stand for 12–18 h, and the residue is isolated. The residue is taken up in 0.1N HCl and purified by reverse phase HPLC (0.01%HCl/acetonitrile) with a 2–90% gradient to yield 42% of 3-(4-amino-benzyl)-2-(3-bromo-2-hydroxy-5-methyl-phenyl)-1H-indole-5-carboxamidine as a white solid (38 mgs, 0.08 mmol).

MS (ESI) Calc for $C_{23}H_{21}BrN_4O$: 448.11, Found: MH+ 448.9.

$^1$HNMR (300 MHz, DMSO) δ: 11.77 (s, 1H), 9.24 (s, 1H), 9.14 (s, 2H), 8.75 (s , 2H), 8.05 (s, 1H), 7.56–7.52 (m, 2H), 7.44 (s, 1H), 7.04–7.15 (m, 5H), 4.07 (s, 2H), 2.2 (s, 3H).

Alternative Synthesis of Indoles

Compounds of Formula I having an indole nucleus can also be synthesized using the procedure discussed in Scheme LXIII below.

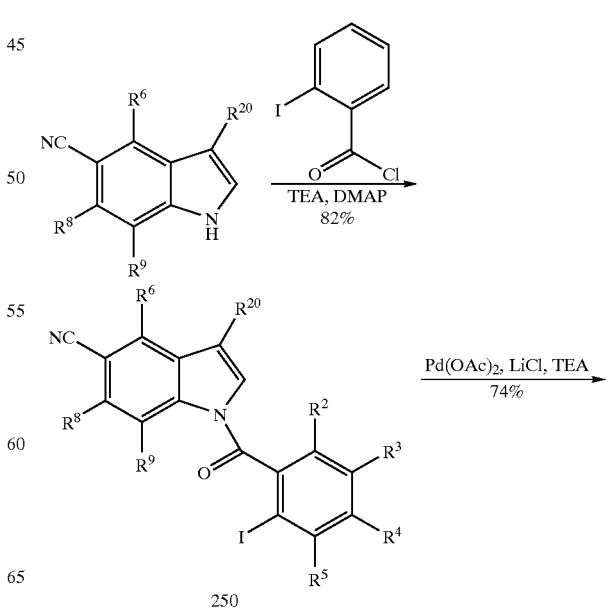

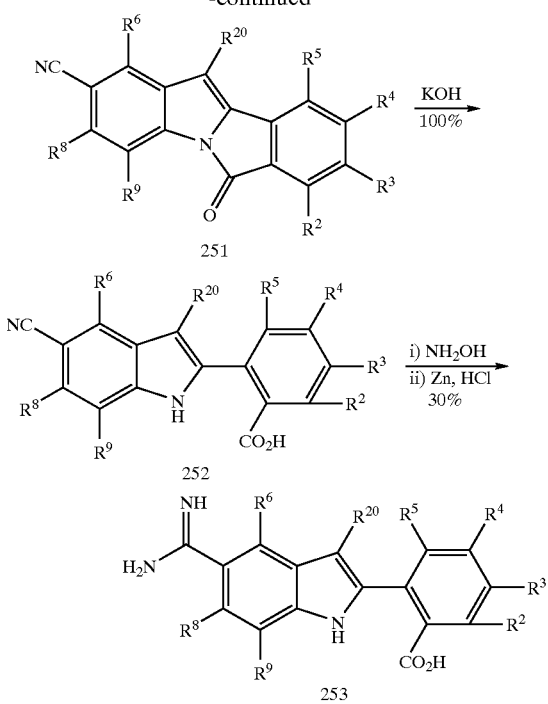

A solution of 2-iodo-benzoyl chloride (2.05 g, 7.7 mmol) in DCM (5.0 mL) is added over a period of 5 min to a stirring DCM solution containing 5-cyano-indole (1.0 g, 7.0 mmol), TEA (1.95 mL, 14 mmol), DMAP (100 mg, 0.8 mmol) at 0° C. The resulting solution is stirred for an additional 1 hZ at ambient temperature. The reaction mixture is then diluted with DCM (50 mL) and washed with $H_2O$ ('3), and sat. $NaHCO_3$ (×3). The organics were then dried ($Na_2SO_4$), and concentrated in vacuo. The residue is recrystallized (EtOAc/Hexanes) to provide 2.14 g (82%) of 5-cyano-1-(2-iodo(carboxyphenyl))indole 250 as a white solid.

$^1$H-NMR (300 MHz, $CDCl_3$) δ: 8.56 (d, 1H, J=4.5 Hz), 8.01 (d, 1H, J=8.1 Hz), 7.91 (s, 1H), 7.71 (d, 1H, J=8.1 Hz), 7.60 (t, 1H, J=7.5 Hz), 7.50 (d, 1H, J=7.5 Hz), 7.34 (t, 1H, J=7.8 Hz), 7.14 (d, 1H, J=3.6 Hz), 6.73 (d, 1H, J=3.6 Hz). MS (+CI, $CH_4$); m/z 373 (MH+), 245, 143.

A mixture of 5-cyano-1-(2-iodo(carboxyphenyl))indole 250 (1.0 g, 2.6 mmol), $Pd(OAc)_2$ (59 mg, 0.26 mmol), triphenylphosphine (120 mg, 0.52 mmol), $Et_3N$ (0.73 mL, 5.2 mmol), and LiCl (120 mg, 2.8 mmol), in $CH_3CN$ (20 mL) is refluxed under $N_2$ for 18 h. Upon cooling, 251 crystallizes out as yellow/green needles.

$^1$H-NMR (300 Mhz, DMSO-$d_6$) δ: 8.07 (s, 1H), 7.84 (d, 2H, J=8.1 Hz), 7.76 (d, 1H, J=7.2 Hz), 7.67 (t, 2H, J=7.2 Hz), 7.47 (t, 1H, J=7.5 Hz), 7.02 (s, 1H).

MS (+CI, $CH_4$); m/z 245 (MH+), 143.

Compound 251 (74 mg, 0.2 mmol) in MeOH (1.0 mL) is treated with KOH (1.0 mL, 40% aq) and heated to 60° C. for 30 min. The mixture is then cooled to ambient temperature and diluted with $H_2O$ (10 mL). The aqueous solution is then acidified with HCl (6 N) to pH=2.0. The resulting solid precipitate is isolated, washed with $H_2O$, and dried in vacuo to provide 70 mg of 252 (90%) as a white solid.

$^1$H-NMR (300 MHz, DMSO-$d_6$) δ: 8.05 (s, 1H), 7.80 (d, 1H), 7.65 (m, 2H), 7.55 (m, 2H), 7.44 (d, 1H), 6.65 (s, 1H).

MS (Bioion) m/z 261.6 (MH+), 168.9.

Compound 252 (35 mg, 0.13 mmol) in EtOH (2.0 mL) is treated with $NH_2OH$ (66 uL, 1.0 mmol, of a 50% soln. in $H_2O$) and refluxed for 16 h. The reaction mixture is concentrated in vacuo, and the residue is taken up in EtOH (4 mL). The ethanol solution is then treated with HCl (1.0 mL of a 4 N soln. in Dioxane) and heated to 60° C. At this point Zn dust (65 mg, 1.0 mmol) is added and the reaction mixture is allowed to stir for 16 h at 60° C. The resulting solution is then cooled and filtered. The filtrate is concentrated and purified by HPLC ($C_{18}$; $H_2O/CH_3CN$) to provide 15 mg (35%) of 253 (Example 836, Table III) as a white powder.

$^1$H-NMR (300 MHz, DMSO-$d_6$) δ: 11.99 (s, 1H), 9.18 (s, 2H), 8.80 (s, 2H), 8.12 (s, 1H), 7.77 (d, 1H), 7.63 (m, 2H), 7.53 (m, 3H), 6.67 (s, 1H).

MS (+ESI): calcd. for $C_{16}H_{14}N_3O_2$; Found: m/z 280.1 (MH+).

Compounds 253 where $R^1$ represents a protected hydroxy group or other appropriate $R^1$ substituents and $R^4$ represents OH can be derivatised at the $R^4$ position by converting the hydroxy group to an alkyl hydroxy group with or without a functional group, as indicated in Scheme LXX below:

Scheme LXX

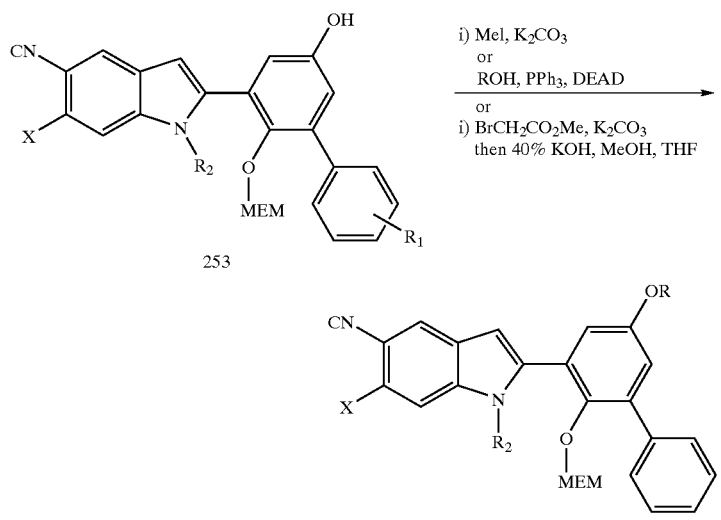

[5-(6-Chloro-5-cyano-1-methansulfonyl-1H-indol-2-yl)-6-(2-methoxyethoxymethoxy)biphenyl-3-yloxylacetic acid ethyl ester 260

A mixture of 6-chloro-2-[5-hydroxy-2-(2-methoxyethoxymethoxy)biphenyl-3-yl]-1-methansulfonyl-1H-indole-5-carbonitrile (7.0 g, 13 mmoles) and $K_2CO_3$ (5.5 g, 23 mmoles) in acetonitrile (200 ml), was mixed with NaI (0.5 g) and bromoethyl acetate (1.6 ml, 14 mmoles). The mixture was stirred for about 18 h at ambient temperature, concentrated, the residue was dissolved in ethyl acetate (400 ml) and washed with brine. The organic layer was dried (MgSO4), filtered and concentrated to afford 8.0 g (98%) of the title compound as a brown foam.

Removal of protecting mesyl group at teh $R^1$ position was accomplished by mehtods known to one skilled in the art. Compounds where $R^4$ represent a substituent comprising a carboxylic acid group can be converted to corresponding amides using the procedures outlined in of Scheme C above.

Compounds of Formula I wherein $R^1$ represents a halo group can be synthesized as outlined in Scheme LXXI below:

Scheme LXXI

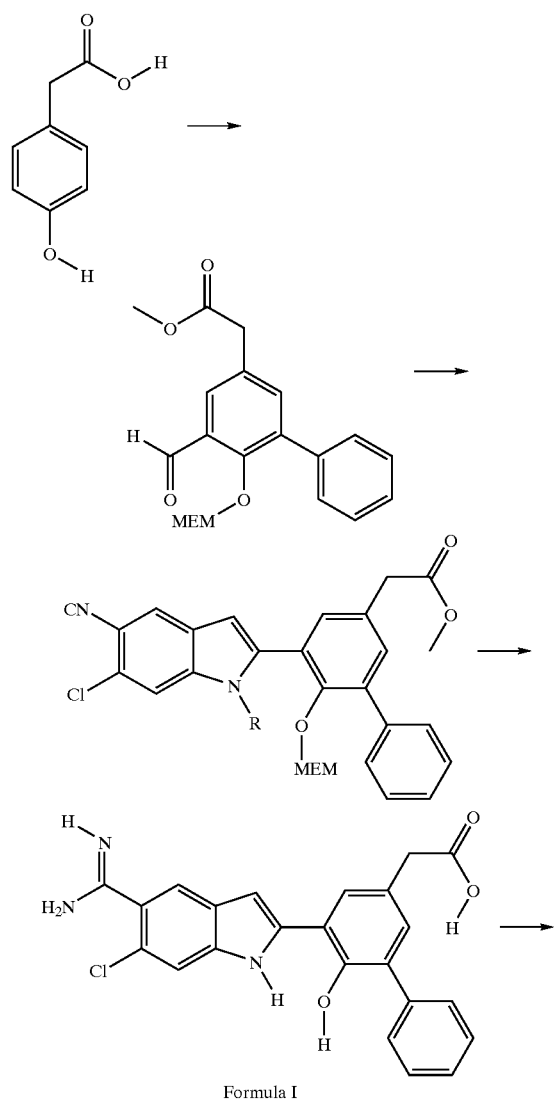

Formula I

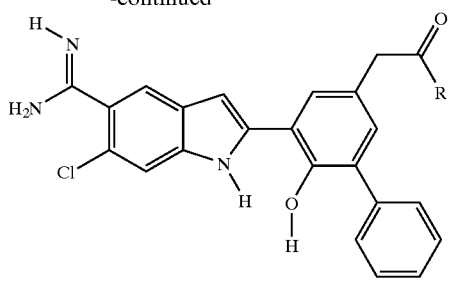

Formula I (4-Hydroxy-phenyl)-acetic acid methyl ester

4-Hydroxyphenylacetic acid (126 mmol, 19.2 g) was dissolved in MeOH (400 ml) and the resulting mixture was cooled in an ice bath (0° C.) under under $N_2$ atmosphere. The cooled reaction mixture was saturated with HCl (gas) and the reaction mixture then was refluxed for 2 h or until all the stating material was completely consumed. The reactin mixture was concentrated and the resulting residue was dissolved in ether, washed with water, brine, dried ($Na_2SO_4$) and concentrated to yield a light colored oil (24.7 g). The purity of this crude material was 95% by HPLC and underwent no further purification prior to the next step.

HPLC (254 nM, r.t.=7.1 min., 1–90% $MeCN/H_2O$, 0.05% TFA)

NMR ($^1$H-300 MHz, DMSO-$d_6$): δ 7.1 (d, 2H), 6.7 (d, 2H), 6.0 (bs, 1H), 3.7 (s, 3H), 3.5 (s, 2H).

(3-Formyl-4-hydroxy-phenyl)-acetic acid methyl ester (3)

The methyl ester from above (126 mmol, 21 g) was dissolved in acetonitrile (650 mL) to form a solution. This solution was mixed with triethylamine (3.4 eq, 60 ml), magnesium dichloride (1.6 eq, 19.7 g), paraformaldehyde in several portions (6.8 eq, 26 gr) to form a yellow mixture. The yellow mixture was refluxed for 3.5 hours at which time TLC revealed that all the starting material was consumed. The reaction mixture was acidified with 6 N HCl, concentrated and extracted with ether (3×150 ml). The ether extracts were washed with water, brine, dried ($Na_2SO_4$) and concentrated to yield 23.6 g (96%) of crude product.

NMR ($^1$H, DMSO-$d_6$): δ 10.6 (s, 1H), 10.4 (s, 1H), 7.5 (s, 1H), 7.4 (d, 1H), 6.9 (d, 1H), 3.62 (s, 2H), 3.59 (s, 3H).

(3-Bromo-5-formyl-4hydroxy-phenyl)-acetic acid methyl ester (4)

The salicylaldehyde from above (122 mmol, 23.6 g) was dissolved in 120 ml acetic acid. Bromine (1.9 eq, 12 ml) was added drop wise over 30 minutes and the dark solution stirred overnight under $N_2$. Volatiles were removed under reduced pressure, the residue dissolved in ether, washed with water followed by brine. The organic layer was dried ($Na_2SO_4$) and concentrated under reduced pressure to yield an oil (32.2 g) (97%).

NMR ($^1$H, DMSO): δ 11.1(bs, 1H), 10 (s, 1H), 7.8 (s, 1H), 7.6 (s, 1H), 3.7 (s, 2H), 3.6 (s, 3H).

[3-Bromo-5-formyl-4-(2-methoxy-ethoxymethoxy)-phenyl]-acetic acid methyl ester (5)

A solution of the aryl bromide (4) (118 mmol, 32.2 g) was dissolved in chloroform (550 mL) was mixed with DIPEA (2.35 eq, 48 ml) followed by rapid drop wise addition of MEM-Cl (2-Methoxy-ethoxymethyl chloride, 1.19 eq, 16 ml). The resulting reaciton mixture was stirred for 8–12 h. The reaction mixture was concentrated, and diluted with ether. The ether mixture was washed with 0.5 M $KHSO_4$ followed by saturated $NaHCO_3$ and brine. The organic phase was dried ($Na_2SO_4$ and concentrated to give a crude oil (43.2 g) 91% pure by HPLC, no further purification performed.

HPLC 254 nm, r.t.=8.0 min., 1–90% MeCN/H$_2$O, 0.05% TFA).

NMR ($^1$H, CDCl$_3$): δ 10.3 (s, 1H), 7.8 (s, 1H), 7.7 (s, 1H), 5.3 (s, 2H), 3.9 (d, 2H), 3.65 (s, 2H), 3.5 (d, 2H), 3.4 (s, 3H). [5-formyl-6-(2-methoxy-ethoxymethoxy)-biphenyl-3-yl]-acetic acid methyl ester (6)

The arylbromide (5) (118 mmol, 42.6 gr) was dissolved in about 430 ml of toluene in a 1 L flask to which 150 ml of 2M K$_2$CO$_3$ was added followed by 5.0 g (0.037 eq) of Pd(PPh$_3$)$_4$. After the addition of phenylboronic acid (2.0 eq, 29 gr) the flask was heated to 70° C. and the mixture stirred for 5 hours. HPLC of the reaction mixture indicated that the arylbromide had completely reacted and a dominant less polar moiety (89% pure, r.t.=8.5 min., 1–90% MeCN/H$_2$O, 0.1% TFA) was observed.

The organic layer from the reaction mixture was isolated, concentrated and diluted with ether. The ether mixture was washed with water, brine and dried with Na$_2$SO$_4$. The resulting organic layer was concentrated and the residue obtained was purified by silica gel column, 30% EtOAc/Hexane to yield 23.7 g, 66% of the title compound.

NMR ($^1$H, DMSO-d$_6$): δ 10.3 (s, 1H), 7.65 (s, 1H), 7.59 (s, 1H), 7.5–7.3 (m, 5H), 4.8 (s, 2H), 3.8 (s, 2H), 3.6 (s, 2H), 3.4 (d, 2H), 3.2 (d, 2H), 3.1 (s, 3H).

MS: (ESI, Sciex) m/z=357.4.

[5-(6-Chloro-5-cyano-1-methanesulfonyl-1H-indol-2-yl)-6-(2-methoxy-ethoxymethoxy)-biphenyl-3-yl]-acetic acid methyl ester (15)

See general Scheme X using the above aldehyde 6

NMR($^1$H, DMSO-d$_6$); δ 8.4 (s, 1H), 8.2 (s, 1H), 7.6–7.3 (m, 7H), 6.9 (s, 1H), 4.6 (s, 2H), 3.7 (s, 3H), 3.65 (s, 2H), 3.25 (s, 2H), 3.2 (s, 3H), 3.0 (b, 1H).

MS: (ESI, Sciex): m/z=579.

15-(6-Chloro-5-cyano-1-methanesulfonyl-1H-indol-2-yl)-6-hydroxy-biphenyl-3-yl]-acetic acid methyl ester (16)

The indole (15) was dissolved in 80 ml methanol treated with 80 ml of 4 N HCl/dioxane at ambient temperature for about 2 h. TLC analysis indicated that all the starting material was consumed and a new product had formed (R$_f$=0.30, 40% EtOAc/Hexane). Volatiles were removed by rotary evaporation, the residue was dissolved in ethyl acetate which was washed three times with water followed by brine. After drying with Na$_2$SO$_4$, concentration gave a crude residue of 3.8 g, 84% pure by HPLC (254 nm).

NMR ($^1$H, DMSO-d$_6$): δ 8.2 (s, 1H), 7.9 (s, 1H), 7.6–7.4 (m, 7H), 7.3 (s, 1H), 6.7 (s, 1H), 3.7 (s, 3H), 3.6 (s, 2H), 3.3 (s, 3H).

MS: (ESI, Sciex): M=495.

[5-(6-Chloro-5-cyano-1H-indol-2-yl)-6-hydroxy-biphenyl-3-yl]-acetic acid (17)

The phenol (16) (4.3 g, 8.7 mmol) was dissolved in 40 ml methanol and 15 ml water. To this was added 32 ml of 14 N NaOH (aq) and the solution was stirred for two hours at ambient temperature. HPLC indicated that all the starting material was consumed and a new moiety had formed. The reaction mixture was diluted water (50 mL), acidified with 6 N HCl and extracted with EtOAC. The organic layer was washed with water (2x), brine and then dried (Na$_2$SO$_4$) and concentrated to yield a yellow solid, 3.0 g, 87%.

HPLC r.t.=7.5 min. (1–90% MeCN/H$_2$O, 0.05% TFA).

MS: (ESI, Sciex): m/z=403.2 (MH+).

{5-[6-Chloro-5-(N-hydroxycarbamimidoyl)-1H-indol-2-yl]-6-hydroxy-biphenyl-3-yl}-acetic acid (18)

A solution of the cyano indole (17) (0.365 gr, 0.91 mmol) from above in dry EtOH (5 ml) was treated with an excess of Hydroxylamine (5 ml of 50 wt. % solution in water). The resulting reaction mixture was refluxed for 10 h. The solvent was removed by rotary evaporation, the residue was azeotroped with toluene to yield the title title compound (0.3–0.4 g).

HPLC r.t.=6.7 min., 1–90% MeCN/H$_2$O, 0.05% TFA).

MS: (ESI, Sciex): m/z=436 (MH+).

[5-(5-Carbamimidoyl-6-chloro-1H-indol-2-yl)-6-hydroxy-biphenyl-3-yl]-acetic acid (19)

Acetic anhydride (1.1 eq, 0.77 ml, in 7 ml of AcOH) was added drop wise to a stirring solution of 3 g of 18 in 34 ml of acetic acid at ambient temperature under N$_2$ over several minutes. HPLC 15 minutes thereafter indicated formation of a hydrophobic product. A catalytic amount of Pd/C (10% w/w) was added to the reaction mixture and teh reaction vessel then was charged with H$_2$ (atm.). The reaction mixture was agitated for about 1.5 h. The agitated reaction mixture was passed through a celite pad (rinsed with ACOH). The filtrate was diluted with ethyl acetate to yield a precipitate. The colid was isolated and dried in vacuo to yield 2.05 g of the crude amdidine.

MS: (ESI, Sciex): m/z=419.

2-[5-(5-Carbamimidoyl-6-chloro-1H-inol-2-yl)-6-hydroxy-biphenyl-3-yl]-N,N-dimethyl-acetamide The compound (19) from above (87 mg, 0.18 mmol) was combined with dimethylamine.HCl (82 mg, 1.9 eq), EDC (425 mg, 1.2 eq), HOBT.H$_2$O (300 mg, 1.2 eq) and DIPEA (0.45 ml, 1.4 eq) in 15 ml DMF. The reaction mixture was stirred overnight. A new moiety was observed by HPLC which LC.MS.ESI (Sciex) confirmed as the product having a mass of 447 A solution of 9:1 EtOAc/ether was added to the reaction kg mixture to afford a precipitate. The precipitated solid was isolated and purified by preparative HPLC (2–90% MeCN/H$_2$O in 40 min., 20 mM HCl) to yield the title compound (88 mg) (11% yield).

Another method to make compounds of Formula I listed in Table III is depicted in Scheme LXXIII below:

Scheme LXXIII

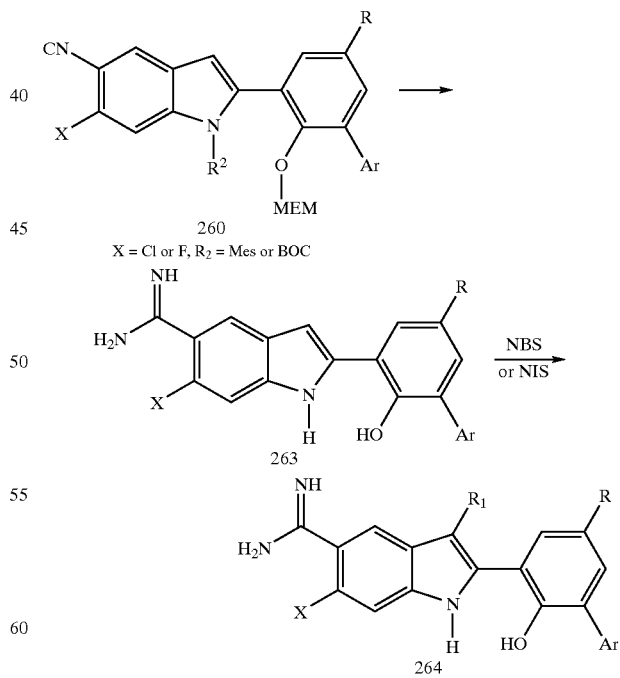

X = Cl or F, R$_2$ = Mes or BOC

6-Chloro-2-[2-(2-methoxy-ethoxymethoxy)-biphenyl-3-yl]-1H-indole-5-carboxamidine 260

The cyano-indole was dissolved in 300 ml dry EtOH in a 1 L flask fitted with a drying tube. Twenty (20) equivalents of hydroxylamine.HCl (54 g) and K$_2$CO$_3$ (107 g) were added and the mixture refluxed overnight. The product was observed by HPLC as was a significant amount of the starting indole. An additional 10 eq of both hydroxylamine-.HCl and K$_2$CO$_3$ were added and the reaction mixture refluxed for an additional 8–12 h. HPLC indicated the reaction had progressed, with about 5% of the starting material remaining. The solid was separated and the filtrate concentrated to yield residue. The residue was diluted with ethyl acetate, washed with water, the organic layer was dried (Na$_2$SO$_4$) and concentrated under reduced pressure to yield compound 260.

LC.MS.ESI (Sciex): m/z=466.

HPLC (r.t.=7.46 min, 254 nm, 1–90% MeCN/H$_2$O, 0.05% TFA).

6-Chloro-2-[2-(2-methoxy-ethoxymethoxy)-biphenyl-3-yl]-1H-indole-5-carboxamidine 262

Compound 260 was dissolved in ACOH (50 ml) and diluted with acetic anhydride. After about an hour the formation of compound 262 was observed. The reduction of the acetylated hydroxyamidine was performed in situ by addition of 2 g (0.05 eq) of Pd/C (palladium on activated carbon, 5% dry weight) and charging the flask with H$_2$ (1 atm). After six hours amidine formation was observed. The reaction mixture was passed through a celite pad, the clear filtrate concentrated to a residue which was purified by silica gel column (5% MeOH/2.5% AcOH/DCM to 10% MeOH/5% AcOH/DCM), the pure fractions concentrated to give 6.0 g (35%) of product 263.

6-Chloro-2-(2-hydroxy-biphenyl-3-yl)-1-indole-5-carboxamidine, 264

The product 263 (13.3 mmol) was dissolved in 50 ml of dry MeOH and 50 ml of anhydrous 4 M HCl/dioxane at r.t. under N$_2$. After agitating the reaction mixture for about an hour, the starting material was consumed and product formatin was observed by HPLC at r.t.=7.25 min (254 nm, 1–90% MeCN/H$_2$O, 0.05% TFA). The solvent was removed under reduced pressure, to yield a foamy oil. The foamy oil was diluted with 0.5 m HCl (aq) to from a precipitate. The precipitated solid was isolated and dried to yield the title compound (2.7 g).

TABLE III

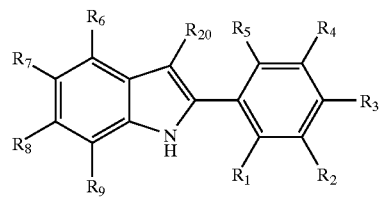

| EX. No. | R$^1$ | R$^2$ | R$^3$ | R$^4$ | R$^5$ | R$^6$ | R$^7$ | R$^8$ | R$^9$ | R$^{20}$ |
|---|---|---|---|---|---|---|---|---|---|---|
| 801 | OH | Br | H | CH$_2$COOH | H | H | C(=NH)NH$_2$ | H | H | benzyl |
| 802 | OH | Br | H | (CH$_2$)$_2$COOH | H | H | C(=NH)NH$_2$ | H | H | benzyl |
| 803 | OH | Br | H | CH$_3$ | H | H | C(=NH)NH$_2$ | H | H | 4-amino-benzyl |
| 804 | OH | Br | H | Br | H | H | C(=NH)NH$_2$ | H | H | benzyl |
| 805 | OH | Cl | H | CH$_3$ | H | H | C(=NH)NH$_2$ | H | H | benzyl |
| 806 | OH | F | H | F | H | H | C(=NH)NH$_2$ | H | H | benzyl |
| 807 | OH | Br | H | CH$_2$COOH | H | H | C(=NH)NH$_2$ | H | H | H |
| 808 | OH | H | H | Cl | H | H | C(=NH)NH$_2$ | H | H | benzyl |
| 809 | OH | Br | H | CH$_2$CONH$_2$ | H | H | C(=NH)NH$_2$ | H | H | H |
| 810 | OH | Br | H | CH$_3$ | H | H | C(=NH)NH$_2$ | H | H | H |
| 811 | OH | Cl | H | CH$_3$ | H | H | C(=NH)NH$_2$ | H | H | H |
| 812 | OH | Cl | H | Cl | H | H | C(=NH)NH$_2$ | H | H | H |
| 813 | OH | Br | H | CONH$_2$ | H | H | C(=NH)NH$_2$ | H | H | H |
| 814 | OH | CH$_3$ | H | CH$_3$ | H | H | C(=NH)NH$_2$ | H | H | benzyl |
| 815 | OH | F | H | F | H | H | C(=NH)NH$_2$ | H | H | H |
| 816 | OH | Br | H | Br | H | H | C(=NH)NH$_2$ | H | H | CH$_3$ |
| 817 | OH | thiophen-3-yl | H | CH$_3$ | H | H | C(=NH)NH$_2$ | H | H | H |
| 818 | OH | Br | H | CH$_3$ | H | H | C(=NH)NH$_2$ | H | H | CH$_2$CONH$_2$ |
| 819 | OH | Br | H | Br | H | H | C(=NH)NH$_2$ | H | H | H |
| 820 | OH | Ph | H | CH$_3$ | H | H | C(=NH)NH$_2$ | H | H | H |
| 821 | OH | Ph | H | H | H | H | C(=NH)NH$_2$ | H | H | H |
| 822 | OH | Cl | H | H | H | H | C(=NH)NH$_2$ | H | H | benzyl |
| 823 | OH | Br | H | nitro | H | H | C(=NH)NH$_2$ | H | H | H |
| 824 | OH | H | H | H | H | H | C(=NH)NH$_2$ | H | H | benzyl |
| 825 | OH | H | H | Cl | H | H | C(=NH)NH$_2$ | H | H | H |
| 826 | OH | Br | H | CH$_3$ | H | H | C(=NH)NH$_2$ | H | H | CH$_2$COOH |
| 827 | OH | CH$_3$ | H | CH$_3$ | H | H | C(=NH)NH$_2$ | H | H | H |
| 828 | OH | p-toluyl | H | methyl | H | H | C(=NH)NH$_2$ | H | H | H |
| 829 | OH | H | H | Br | H | H | C(=NH)NH$_2$ | H | H | H |
| 830 | OH | H | H | methyl | H | H | C(=NH)NH$_2$ | H | H | H |
| 831 | OH | COOH | H | methyl | H | H | C(=NH)NH$_2$ | H | H | H |
| 832 | OH | H | H | H | H | H | C(=NH)NH$_2$ | H | H | H |
| 833 | OH | H | H | H | H | H | C(=NH)NH$_2$ | H | H | methyl |
| 834 | COOH | OH | H | H | H | H | C(=NH)NH$_2$ | H | H | H |
| 835 | COOH | Ethoxy | H | H | H | H | C(=NH)NH$_2$ | H | H | H |
| 836 | COOH | H | H | H | H | H | C(=NH)NH$_2$ | H | H | H |
| 837 | OH | Br | H | CH$_3$ | H | H | C(=NH)NH$_2$ | H | H | benzyl |
| 838 | OH | Cl | H | Cl | H | Cl | C(=NH)NH$_2$ | H | H | H |
| 839 | OH | Cl | H | Cl | H | H | C(=NH)NH$_2$ | Cl | H | H |

TABLE III-continued

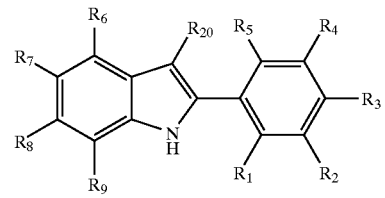

| EX. No. | $R^1$ | $R^2$ | $R^3$ | $R^4$ | $R^5$ | $R^6$ | $R^7$ | $R^8$ | $R^9$ | $R^{20}$ |
|---|---|---|---|---|---|---|---|---|---|---|
| 840 | OH | Ph | H | H | H | H | NHC(=NH)NH$_2$ | H | H | H |
| 841 | OH | Br | H | Me | H | H | C(=NH)NH$_2$ | H | H | p-nitrobenzyl |
| 842 | OH | Br | H | Me | H | H | C(=NH)NH$_2$ | H | H | m-nitrobenzyl |
| 843 | OH | O—CH$_2$—CH$_2$—O | | H | H | | C(=NH)NH$_2$ | H | H | H |
| 844 | H | H | 4-yloxy-benzamidine | H | H | H | C(=NH)NH$_2$ | H | H | H |
| 845 | OH | Br | H | Me | H | H | H | C(=NH)NH$_2$ | H | H |
| 846 | OH | Ph | CH$_2$COOH | H | H | H | C(=NH)NH$_2$ | Cl | H | H |
| 847 | OH | Ph | H | 2-Piperidin-1-yl-ethylcarbamoyl)-methyl | H | H | C(=NH)NH$_2$ | Cl | H | H |
| 848 | OH | Ph | H | Benzylcarbamoyl-methl-yl | H | H | C(=NH)NH$_2$ | Cl | H | H |
| 849 | OH | Ph | H | 2-Morpholin-4-yl-ethylcarbamoyl)-methyl | H | H | C(=NH)NH$_2$ | Cl | H | H |
| 850 | OH | Ph | H | 2-Propionylamino-succinic acid-1-yl | H | H | C(=NH)NH$_2$ | Cl | H | H |
| 851 | OH | Ph | H | CH$_2$CON(C$_3$)$_5$ | H | H | C(=NH)NH$_2$ | Cl | H | H |
| 852 | OH | Ph | H | CH$_2$CONH(CH$_2$)$_3$—OMe | H | H | C(=NH)NH$_2$ | Cl | H | H |
| 853 | OH | Ph | H | 2-(5-Amino-1-carboxy-pentyl-carbamoyl)-ethylamino | H | H | C(=NH)NH$_2$ | Cl | H | H |
| 854 | OH | Ph | H | CH$_2$CONH$_2$ | H | H | C(=NH)NH$_2$ | Cl | H | H |
| 855 | OH | Ph | H | [Bis-(2-methoxy-ethyl)-carbamoyl]-methyl | H | H | C(=NH)NH$_2$ | Cl | H | H |
| 856 | OH | Ph | H | 2-Hydroxymethyl-pyrrolidin-1-yl-2-oxo-eth-1-yl | H | H | C(=NH)NH$_2$ | Cl | H | H |
| 857 | OH | Ph | H | CH$_2$CONH—CH$_2$—CF$_3$ | H | H | C(=NH)NH$_2$ | Cl | H | H |
| 858 | OH | Ph | H | Furan-2-ylmethyl-carbamoyl-meth-1-yl | H | H | C(=NH)NH$_2$ | Cl | H | H |
| 859 | OH | Ph | H | Tetrahydro-furan-2-ylmethyl)-carbamoyl]-meth-1-yl | H | H | C(=NH)NH$_2$ | Cl | H | H |
| 860 | OH | Ph | H | (1,1-Dioxo-1-thiomorpholin-4-yl)-2-oxo-eth-1-yl | H | H | C(=NH)NH$_2$ | Cl | H | H |
| 861 | OH | Ph | H | [(Benzo[1,3]dioxol-5-ylmethyl)-carbamoyl]-meth-1-yl | H | H | C(=NH)NH$_2$ | Cl | H | H |
| 862 | OH | Ph | H | [2-(3H-Imidazol-4-yl)-ethyl-carbamoyl]-meth-1-yl | H | H | C(=NH)NH$_2$ | Cl | H | H |
| 863 | OH | Ph | H | (2-Methoxy-1-methyl-ethyl-carbamoyl)-meth-1-yl | H | H | C(=NH)NH$_2$ | Cl | H | H |
| 864 | OH | Ph | H | thiophen-2-ylcarbamoylmethyl | H | H | C(=NH)NH$_2$ | Cl | H | H |
| 865 | OH | Ph | H | 2-(4-Methyl-piperazin-1-yl)-2-oxo-ethyl | H | H | C(=NH)NH$_2$ | Cl | H | H |
| 866 | OH | Ph | H | [(Pyridin-3-ylmethyl)-carbamoyl]-methyl | H | H | C(=NH)NH$_2$ | Cl | H | H |
| 867 | OH | Ph | H | H | H | H | C(=NH)NH$_2$ | Cl | H | H |
| 868 | OH | Ph | H | Br | H | H | C(=NH)NH$_2$ | Cl | H | H |
| 869 | OH | Ph | H | o-cyclohexyl | H | H | C(=NH)NH$_2$ | Cl | H | H |
| 870 | OH | Ph | H | OMe | H | H | C(=NH)NH$_2$ | Cl | H | H |
| 871 | OH | Ph | H | OCH$_2$COOH | H | H | C(=NH)NH$_2$ | Cl | H | H |
| 872 | OH | Ph | H | Cl | H | H | C(=NH)NH$_2$ | Cl | H | H |
| 873 | OH | Ph | H | OCH$_3$CH$_2$NH-acetyl | H | H | C(=NH)NH$_2$ | Cl | H | H |
| 874 | OH | Ph | H | OH | H | H | C(=NH)NH$_2$ | Cl | H | H |
| 875 | OH | Ph | H | OCH$_3$CH$_3$COOH | H | H | C(=NH)NH$_2$ | Cl | H | H |
| 876 | OH | Ph | H | OCH$_2$CH$_2$OH | H | H | C(=NH)NH$_2$ | Cl | H | H |
| 877 | OH | Ph | H | H | H | H | C(=NH)NH$_2$ | F | H | H |
| 878 | OH | Ph | H | OCH$_3$COOH | H | H | C(=NH)NH$_2$ | F | H | H |
| 879 | OH | 2-Methyl-cyclohexyloxy | H | | H | H | C(=NH)NH$_2$ | F | H | H |
| 879 | OH | 2-Methyl-cyclohexyloxy | H | | H | H | C(=NH)NH$_2$ | F | H | H |
| 879 | OH | 2-Methyl-cyclohexyloxy | H | | H | H | C(=NH)NH$_2$ | F | H | H |
| 879 | OH | 2-Methyl-cyclohexyloxy | H | | H | H | C(=NH)NH$_2$ | F | H | H |
| 879 | OH | 2-Methyl-cyclohexyloxy | H | H | H | H | C(=NH)NH$_2$ | F | H | H |

TABLE III-continued

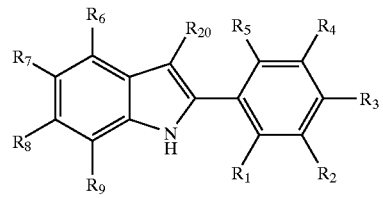

| EX. No. | R¹ | R² | R³ | R⁴ | R⁵ | R⁶ | R⁷ | R⁸ | R⁹ | R²⁰ |
|---|---|---|---|---|---|---|---|---|---|---|
| 880 | OH | 2-Methyl-cyclohexyloxy | H | $CH_2COOH$ | H | H | $C(=NH)NH_2$ | F | H | H |
| 881 | OH | 2-Methyl-cyclohexyloxy | H | $CH_2CON(Me)_2$ | H | H | $C(=NH)NH_2$ | F | H | H |
| 882 | OH | 2-Methyl-cyclohexyloxy | H | [bis-(2-methoxy-ethyl)-carbamoyl]-methyl | H | H | $C(=NH)NH_2$ | F | H | H |
| 883 | OH | 2-Methyl-cyclohexyloxy | H | morpholine-4-carbonyl | H | H | $C(=NH)NH_2$ | F | H | H |
| 884 | OH | 2-Methyl-cyclohexyloxy | H | (2-Methoxy-ethylcarbamoyl)-methyl | H | H | $C(=NH)NH_2$ | F | H | H |
| 885 | OH | 2-Methyl-cyclohexyloxy | H | $CH_2$—CONH—Me | H | H | $C(=NH)NH_2$ | F | H | H |
| 886 | OH | 2-Methyl-cyclohexyloxy | H | $CH_2$—CONH—$CH_2CH_2OH$ | H | H | $C(=NH)NH_2$ | F | H | H |
| 887 | OH | 2-Methyl-cyclohexyloxy | H | $CH_2$—CON—$(CH_2CH_2OH)_2$ | H | H | $C(=NH)NH_2$ | F | H | H |
| 888 | OH | 2-Methyl-cyclohexyloxy | H | 4-hydroxy-piperidine-1-carbonyl | H | H | $C(=NH)NH_2$ | F | H | H |
| 889 | OH | 2-Methyl-cyclohexyloxy | H | thiomorpholine-4-carbonyl | H | H | $C(=NH)NH_2$ | F | H | H |
| 890 | OH | Ph | H | methanesulfonylamino-methoxy | H | H | $C(=NH)NH_2$ | Cl | H | H |
| 891 | OH | Ph | H | benzoylamino-methoxy | H | H | $C(=NH)NH_2$ | Cl | H | H |
| 892 | OH | Ph | H | [(thiophene-2-carbonyl)-amino]-methoxy | H | H | $C(=NH)NH_2$ | Cl | H | H |
| 893 | OH | Ph | H | [(morpholine-4-carbonyl)-amino]-methoxy | H | H | $C(=NH)NH_2$ | Cl | H | H |
| 894 | OH | Ph | H | (4-chloro-benzenesulfonylamino)-methoxy | H | H | $C(=NH)NH_2$ | Cl | H | H |
| 895 | OH | Ph | H | $OCH_2COOH$ | H | H | $C(=NH)NH_2$ | Cl | H | H |
| 896 | OH | Ph | H | $OCH_2COOEt$ | H | H | $C(=NH)NH_2$ | Cl | H | H |
| 897 | OH | Ph | H | 2-methoxy-ethoxycarbonylmethoxy | H | H | $C(=NH)NH_2$ | Cl | H | H |
| 898 | OH | Ph | H | $OCH_2CON(Me)_2$ | H | H | $C(=NH)NH_2$ | Cl | H | H |
| 899 | OH | Ph | H | 2-morpholin-4-yl-2-oxy-ethoxy | H | H | $C(=NH)NH_2$ | Cl | H | H |
| 900 | OH | Ph | H | 2-(4-hydroxy-piperidin-1-yl)-2-oxo-ethoxy | H | H | $C(=NH)NH_2$ | Cl | H | H |
| 901 | OH | Ph | H | (1,2-dihydroxy-ethylcarbamoyl)-methoxy | H | H | $C(=NH)NH_2$ | Cl | H | H |
| 902 | OH | Ph | H | 3-Hydroxy-1-(2-hydroxy-ethyl)-propylcarbamoyl | H | H | $C(=NH)NH_2$ | Cl | H | H |

Ex. 801

$^1$H-NMR ($d_6$-dmso) δ: 3.5 vbn3 9s, 2H), 4.04 (s, 2H), 7.05–7.22 (m, 7H), 7.49–7.55 (m, 2H), 8.15 (s, 1H), 8.77 (s, 2H), 9.21 (s, 2H), 9.42 (s, 1H), 11.75 (s, 1H), 12.33 (br.s, 1H).

Mass (ESI) M⁺+1: Calculated: 477.8, Obs.: 478.3.

Ex. 802

$^1$H-NMR ($d_6$-dmso) δ: 9.32 (s, 1H), 9.14 (s, 2H), 8.74 (s, 2H), 8.08 (s, 1H), 7.5 (m, 4H), 7.11 (m, 6H), 4.09 (s, 2H), 2.69 (t, 2H, J=7.4 Hz), 2.48 (t, 2H, J=7.4 Hz).

Mass (LRMS) M⁺+1: Calculated: 491.08; Obs.: 492.7.

Ex. 803

$^1$HNMR (300 MHz, DMSO-$d_6$) δ: 11.77 (s, 1H), 9.24 (s, 1H), 9.14 (s, 2H), 8.75 (s , 2H), 8.05 (s, 1H), 7.56–7.52 (m, 2H), 7.44 (s, 1H), 7.04–7.15 (m, 5H), 4.07 (s, 2 H), 2.2 (s, 3H).

MS (ESI) Calc for $C_{23}H_{21}BrN_4O$: 448.11, Found: MH+ 448.9.

Ex. 804

$^1$H-NMR ($d_6$-dmso) δ: 8.1 (s, 1H), 7.8 (d, 1H, J=2.41 hz), 7.58 (d, 1H, J=10.18 Hz), 7.52 (d, 1H, J=10.2 Hz), 7.32 (d, 1H, J=2.41 Hz), 7.2–7.0 (m, 5H), 4.1 (s, 2H).

Mass (ESI) M⁺+1: Calculated: 497.01, Obs.: 499.9.

Ex. 805

$^1$H-NMR ($d_6$-dmso) δ: 11.7 (s, 1H), 9.4 (s, 1H), 9.2 (s, 2H), 8.7 (s, 2H), 8.06 (br.s, 1H), 7.55 (dd, 1H, J=8.57 Hz), 7.50 (d, 1H, J=8.59 Hz), 7.28 (d, 1H, J=1.52 Hz), 7.2–7.05 (m, 5H), 6.98 (d, 1H, J=1.55 hz), 4.1 (s, 2H), 2.2 (s, 3H).

Mass (ESI) M⁺+1: Calculated: 389.88, Obs.: 390.1.

Ex. 807

$^1$H-NMR ($d_6$-dmso) δ: 3.52 (s, 2H), 7.11 (s, 1H), 7.47–7.62 (d, 4H), 8.79 (s, 2H), 9.15 (s, 2H), 9.60 (br.s, 1H), 11.86 (s, 1H).

Mass (ESI) M⁺+1: Calculated: 387.6, Obs.: 388.2.

Ex. 808

¹H-NMR (d₆-dmso) δ: 8.05 (s, 1H), 7.6–6.9 (m, 10H), 4.1 (s, 2H).

Mass (ESI) M⁺+1: Calculated: 375.11, Obs.: 375.9.

Ex. 809

¹H-NMR (d₆-dmso) δ: 3.38 (s, 2H), 6.96 (s, 1H), 7.45–7.64 (m, 4H), 8.18 9s, 1H), 8.83 (s, 2H), 4.20 (s, 2H), 9.58 (br.s), 11.91 (s, 1H).

Mass (ESI) M⁺+1: Calculated: 387.2, Obs.: 386.9.

Ex. 810

2-(3-Bromo-2-hydroxy-5-methyl-phenyl)-1H-indole-5-carboxamidine

¹H NMR (DMSO-d₆) δ: 9.16 (s, 2H), 8.70 (s, 2H), 8.14 (s, 1H), 7.61 (d, 1H, J=8.66 Hz), 7.58 (d, 1H, J=1.49 Hz), 7.54 (dd, 1H, J=8.66 Hz), 7.41 9d, 1H, J=1.24 Hz), 7.14 (s, 1H), 2.30 (s, 3H).

MS: 343.03(calc); 344 (obs.).

Ex. 811

¹H-NMR (d₆-dmso) δ: 11.8 (s, 1H), 9.7 (s, 1H), 9.2 (s, 2H), 8.8 (s, 2H), 8.12 (s, 1H), 7.6 (d, 1H, J=8.62 Hz), 7.57 (br.s, 1H), 7.52 (d, 1H, J=8.73 Hz), 7.24 (br.s, 1H), 7.16 (s, 1H), 2.3 (s, 3H).

Mass. (M⁺+1): Calculated: 299.08; Observed: 279.8.

EX. 812

2-(3,5-Dichloro-2-hydroxy-phenyl)-1H-indole-5-carboxamidine

¹H NMR (CD₃OD) δ: 8.14 (d, 1H, J=1.7 Hz), 7.74 (d, 1H, J=2.7 Hz), 7.63 (d, 1H, J=8.1 Hz), 7.57 (dd, 1H, J=1.7, 8.1 Hz), 7.4 (d, 1H, J=2.7 Hz), 7.25 (s, 1H).

MS: 319.0 (calc.); 319.7 (obs.).

Ex. 813

¹H-NMR (d₆-dmso) δ: 12.1 (s, 1H), 10.21 (s, 1H), 9.2 (s, 2H), 8.8 (s, 2H), 8.32 (s, 1H), 8.2 (s, 1H), 8.1 (d, 1H, J=1.98 Hz)8.05 (s, 1H), 7.6 (d, 1H), J=8.56 Hz), 7.55 (dd, 1H, J=8.67 Hz), 7.46 (s, 1H), 7.2 (s, 1H).

Mass (ESI) M⁺+1: Calculated: 372.04, Obs.: 372.8.

Ex. 814

¹H-NMR (d₆-dmso) δ: 11.7 (s, 1H), 9.1 (s, 2H), 8.69 (s, 2H), 8.49 (s, 1H), 8.0 (s, 1H), 7.6–7.4 (m, 2H), 7.2–7.0 (m, 5H), 6.99 (d, 1H, J=0.5 Hz), 6.86 (d, 1H, J=1.32 Hz), 4.1 (s, 2H), 2.25 (s, 3H), 2.15 (s, 3H).

Mass (ESI) M⁺+1: Calculated: 369.46, Obs.: 370.1.

EX. 815

2-(3,5-Difluoro-2-hydroxy-phenyl)-1H-indole-5-carboxamidine

MS: 287.1 (calc.); 287.8 (obs.).

Ex. 816

¹H-NMR (d₆-dmso) δ: 11.7 (s, 1H), 9.75 (s, 1H), 9.15 (s, 2H), 8.69 (s, 2H), 8.19 (s, 1H), 7.82 (s, 1H), 7.57 (d, 1H, J=8.57 Hz), 7.55–7.4 (m, 2H), 2.25 (s, 2H).

Mass (ESI) M⁺+1: Calculated: 420.98, Obs.: 424.6.

Ex. 817

2-(2-Hydroxy-5-methyl-3-thiophen-2-yl-phenyl)-1H-indole-5-carboxamidin

¹H NMR (DMSO-d₆): δ 9.12 (s, 2H), 8.70 (s, 2H), 8.11 (d, 1H, J=1.68 Hz), 7.70–7.77 (m, 1H), 7.63–7.46 (m, 5H), 7.24 (d, 2H, J=Hz), 7.09 (s, 1H), 2.32 (s, 3H).

MS: 347.11(calc); 348.0 (obs.).

Ex. 818

¹H-NMR (d₆-dmso) δ: 11.8 (s, 1H), 9.9 (s, 1H), 9.2 (s, 2H), 8.7 (s, 2H), 8.2 (s, 1H), 8.0–7.4 (m, 3H), 7.2 (s, 1H), 3.5 (s, 2H), 2.2 (s, 3H).

Mass (ESI) M⁺+1: Calculated: 369.18, Obs.: 400.9.

Ex. 819

¹H-NMR (d₆-dmso) δ: 12.0 (s, 1H), 10.0 (s, 1H), 8.8 (s, 2H), 8.15 (s, 1H), 7.95 (d, 1H, 2.38 Hz), 7.76 (d, 1H, J=2.33 Hz), 7.60 (d, 1H, J=8.44 Hz), 7.55 (d, 1H, J=8.47 hz), 7.24 (s, 1H).

Mass (ESI) M⁺+1: Calculated: 406.97, Obs.: 409.8.

Ex. 821

2-(2-hydroxybiphen-3-yl)-5-amidinoindole hydrochloride

¹H NMR (DMSO-d₆) δ: 11.6 (s, 1H), 9.16 (s, 2H), 8.96 (s, 1H), 8.15 (s, 1H), 7.74 (dd, 1H, J=7.67 Hz), 7.64 (d, 1H, J=8.66 hz), 7.57–7.35 (m, 5H), 7.25 (dd, 1H, J=7.67 Hz), 7.12 (s, 1H), 7.11 (t, 1H, J=7.67 Hz).

MS: 327.14(calc.); 327.7 (obs.).

Ex. 822

¹H-NMR (d₆-dmso) δ: 11.7 (s, 1H), 10.3 (s, 1H), 9.1 (s, 2H), 8.65 (s, 2H), 8.05 (s, 1H), 7.53 (m, 1H), 7.3–7.0 (m, 9H), 4.1 (s, 2H).

Mass (ESI) M⁺+1: Calculated: 375.11, Obs.: 376.0.

Ex. 823

¹H-NMR (d₆-dmso) δ: 7.28 (s, 1H), 7.57 (d, 1H, J=8.4 Hz), 7.62 (d, 1H, J=8.4 Hz), 8.19 (s, 1H), 8.39 (d, 1H, J=1.2 Hz), 8.61 (d, 1H, J=1 Hz), 8.84 (s, 2H), 9.21 9s, 2H), 12.3 (s, 1H).

Mass (ESI) M⁺+1: Calculated: 375.2, Obs.: 375.6.

Ex. 825

¹H-NMR (d₆-dmso) δ: 11.8 (s, 1H), 9.15 (s, 2H), 8.8 (s, 2H), 8.1 (s, 1H), 7.85 (d, 1H, J=1.64 Hz), 7.62 (d, 1H, J=8.51 Hz), 7.52 (d, 1H, J=8.45 hz), 7.25 (s, 1H), 7.3–7.2 (m, 1H), 7.05 (d, 1H, J=8.73 Hz).

Mass (ESI) M⁺+1: Calculated: 265.12, Obs.: 285.8.

Ex. 826

¹H-NMR (d₆-dmso) δ: 11.8 (s, 1H), 9.2 (s, 2H), 8.7 (s, 2H), 8.2(s, 1H), 8.0–7.4 (m, 3H), 7.2 (s, 1H), 3.6 (s, 2H), 2.2 (s, 3H).

Mass (ESI) M⁺+1: Calculated: 401.06, Obs.: 401.9.

Ex. 827

¹H-NMR (d₆-dmso) δ: 11.8 (s, 1H), 9.16 (s, 2H), 8.85 (s, 2H), 8.1 (s, 1H), 7.6 (d, 8.58, J=8.58 Hz), 7.5 (d, 1H, J=8.64 Hz), 7.4 (s, 1H), 7.1 (s, 1H), 6.9 (s, 1H), 2.24 (s, 3H).

Mass.: Calc. 279.14; Obs.: 279.8.

Ex. 828

2-(2-Hydroxy-5,4'-dimethyl-biphenyl-3-yl)-1H-indole-5-carboxamidine $^1$H NMR (DMSO-d$_6$) δ: 9.15 (s, 2H), 8.75 (s, 2H), 8.65 (s, 1H), 8.21 9s, 1H), 8.13 (s, 1H), 7.63 (d, 1H, J=8.66 Hz), 7.54–7.51 (m, 2H), 7.43 (d, 2H, 2H), 7.27 (d, 2H, J=7.67 Hz), 7.11 (s, 1H), 7.04 (d, 1H, J=1.73 Hz), 2.36 (s, 3H), 2.33 (s, 3H).

MS: 355.17(calc.); 356.1 (obs.).

Ex. 829

$^1$H NMR (D$_6$-DMSO) δ: 7.03 (d, 1H, J=8.75), 7.25 (s, 1H), 7.34 (dd, 1H, J=8.75, 2.3), 7.54 (dd, 1H, J=8.59), 7.63 (d, 1H, J=8.59), 7.98 (d, 1H, J=2.3), 8.13 (s, 1H), 8.86 (s, 2H), 9.18 (s, 2H), 10.76 (s, 1H), 11.84 (s, 1H).

Mass Bioion (M+H$^+$): Calculated: 329.02; Obs.: 330.5.

Ex. 830

$^1$H-NMR (d$_6$-dmso) δ: 11.7 (s, 1H), 10.1 (s, 1H), 9.15 (s, 2H), 8.7 (s, 2H), 8.1 (s, 1H), 7.62 (d, 1H, J=8.65 Hz), 7.60 (s, 1H), 7.5 (d, 1H, J=8.64 Hz), 7.1 (s, 1H), 7.0 (d, 1H, J=8.46 Hz), 6.9 (d, 1H, 8.0 hz), 2.25 (s, 3H).

Mass (ESI) M$^+$+1: Calculated: 265.12; Obs.: 265.9.

Ex. 836

$^1$H-NMR (300 MHz, DMSO-d$_6$) δ: 11.99 (s, 1H), 9.18 (s, 2H), 8.80 (s, 2H), 8.12 (s, 1H), 7.77 (d, 1H, J=7.5 Hz), 7.63 (m, 2H), 7.53 (m, 3H), 6.67 (s, 1H). MS (+ESI); m/z 280.1 (MH+). calcd. for C$_{16}$H$_{14}$N$_3$O$_2$; m/z 280.1.

Ex. 837

$^1$H-NMR (d$_6$-dmso) δ: 11.8 (s, 1H), 9.25 (s, 1H), 9.15 (s, 2H), 8.7 (s, 2H), 8.08 (s, 1H), 7.57 (d, 1H, J=8.46 Hz), 7.51 (d, 1H, J=8.57 Hz), 7.44 (d, 1H, J=1.25 Hz), 7.25–7.05 (m, 5), 7.0 (d, 1H, J=1.51 Hz), 4.1 (s, 2H), 2.22 (s, 3H).

Mass (ESI) M$^+$+1: Calculated: 433.10, Obs.: 434.0.

Ex. 841

3-(4-nitro-benzyl)-2-(3-bromo-2-hydroxy-5-methyl-phenyl)-1H-indole-5-carboxamidine $^1$HNMR (300 MHz, DMSO) δ: 11.84 (s, 1H), 9.24 (s, 1H), 9.11 (s, 2H), 8.70 (s, 2H), 8.06 (d, 2H, J=7.6 Hz), 8.04 (s, 1H), 7.60–7.56 (m, 2H), 7.36 (s, 1H), 7.34 (d, 2H, J=7.6 Hz), 6.03 (s, 1H), 4.21 (s, 2H), 2.20 (s, 3H).

MS (ESI) Calc for C$_{23}$H$_{19}$BrN$_4$O$_3$: 478.08, Found: MH+ 479.4.

Ex. 843

Mass (ESI) M$^+$+1: Calculated; 309.1; Obs.: 309.7.

Utility

Compounds of the present invention are useful as inhibitors of proteases, which play a significant role in the progression of cancer. Their inhibitory activity includes inhibition of urokinase (uPA) which has been postulated to have therapeutic value in treating cancer.

The compounds of this invention are also useful as anticoagulants for the treatment or prevention of thromboembolic disorders in mammals. The term "thromboembolic disorders" as used herein includes arterial or venous cardiovascular or cerebrovascular thromboembolic disorders, including, for example unstable angina, first or recurrent ischemic attack, stroke, atherosclerosis, venous thrombosis, deep vein thrombosis, thrombophlebitis, arterial embolism, kidney embolisms, and pulmonary embolisms. The anticoagulant effect of compounds of the present invention is believed to be due to the inhibition of Factor Xa (FXa), Factor VIIa (FVIIa), and thrombin.

Some of the compounds of the present invention show selectivity between uPA and FXa, with respect to their inhibitory properties. The effectiveness of compounds of the present invention as inhibitors of Urokinase and Factor Xa is determined using synthetic substrates and purified Urokinase and purified human Factor Xa respectively.

The rates of hydrolysis by the chromagenic substrates were measured both in the absence and presence of compounds of the present invention. Hydrolysis of the substrates result in the release of the -pNA moiety, which is monitored spectrophotometrically by measuring the increase in absorbance at 405 nano meter (nm). A decrease in the rate of absorbance change at 405 nm in the presence of a inhibitor is indicative of enzyme inhibition. The results of this assay are expressed as the inhibitory constant, Ki app.

Factor Xa determinations were made in 50 mM Tris buffer, pH 7.5, containing 1M NaCl, 5 mM CaCl2, 0.05% Tween-20, and 1.5 mM EDTA. Values of Ki app. were determined by allowing 2–3 nM human Factor Xa (Haematologic Technologies, VT, USA) to react with the substrate (1 mM) in the presence of an inhibitor. Hydrolysis of the chromogenic substrate is followed spectrophotometrically at 405 nm for five minutes. The enzyme assay routinely yielded linear progression curves under these conditions. Initial velocity measurements calculated from the progress curves by a kinetic analysis program (Batch Ki; Peter Kuzmic, BioKin, Ltd., Madison, Wis.) were used to determine Ki app.

Urokinase inhibition determinations were made in 50 mM Tris (pH7.5), 150 mM NaCl, 0.05% Tween-20, 0.002% antifoam, and 1 mM EDTA. human Urokinase (from American Diagnostica, CT, USA). Values of Ki app. were determined by allowing 20 nM human Urokinase to react with the Pefachrome substrate (0.3 mM, Centerchem, Conn., USA) in the presence of an inhibitor. Hydrolysis of the chromogenic substrate is followed spectrophotometrically at 405 ram for five minutes. The enzyme assay routinely yielded linear progression curves under these conditions. Initial velocity measurements calculated from the progress curves by a kinetic analysis program (Batch Ki; Peter Kuzmic, BioKin, Ltd., Madison, Wis.) were used to determine Ki app.

Table IV lists inhibition constants (Ki app.) for representative compounds of the present invention. These values are for uPA and FXa.

TABLE IV

| Ex. | uPA Ki μM | FXa Ki μM |
|---|---|---|
| 110 | 0.51 | |
| 116 | 0.651 | |
| 258 | | 0.46 |
| 291 | 0.85 | 0.85 |
| 802 | 0.26 | 0.000618 |
| 820 | 0.065 | 0.298 |
| 877 | 2.5 | 0.033 |
| 860 | 0.004 | 5.4 |

Definitions

The compounds of the present invention may have asymmetric centers. Compounds of the present invention containing an asymmetrically substituted atom may be isolated in optically active or racemic forms. It is well known in the art how to prepare optically active forms, such as by resolution of materials. Many geometric isomers of olefins, C=N double bonds, and the like can be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure (representing a compound of Formula I) are intended, unless the specific stereochemistry or isomeric form is specifically indicated.

As used herein, the following terms and abbreviations have the following meaning, unless indicated otherwise.

The term "prodrug" is intended to represent covalently bonded carriers which are capable of releasing the active ingredient of Formula I, when the prodrug is administered to a mammalian subject. Release of the active ingredient occurs in viva. Prodrugs can be prepared by techniques known to one skilled in the art. These techniques generally modify appropriate functional groups in a given compound. These modified functional groups however regenerate original functional groups by routine manipulation or in vivo. Prodrugs of compounds of Formula I include compounds wherein a hydroxy, amidino, guanidino, amino, carboxylic or a similar group is modified.

"Pharmaceutically acceptable salts" is as understood by one skilled in the art. Thus a pharmaceutically acceptable salt includes acid or base salts of compounds of Formula I. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in *Remington's Pharmaceutical Sciences*, 17th ed., Mack Publishing Company, Easton, Pa., 1985, which is incorporated herein by reference.

"Optional" or "optionally" means that the subsequently described event or circumstance may or may not occur, and that the description includes instances where the event or circumstance occurs and instances in which it does not. For example, the phrase "optionally is substituted with one to three substituents" means that the group referred to may or may not be substituted in order to fall within the scope of the invention. Thus the term "optionally substituted" is intended to mean that any one or more hydrogens on a designated atom can be replaced with a selection from the indicated group, provided that the designated atom's normal valence is not exceeded, and that the substitution results in a stable compound. When the substituent is keto (=O) then 2 hydrogens on the atom are replaced. "Optional substituents", unless otherwise indicated, are independently selected from a group consisting of H; $N(R^{10})_2$; $NO_2$; halogen; aryl; O—$C_{5-10}$ cyclo alkyl substituted with $R^{10}$; guanidino; urea; thio urea; amidino; para or meta phenoxy; piperidin-4-yloxy; 4-amino-cyclohexyloxy; 1-(1-Imino-ethyl)-piperidin-4-yloxy; 1-(1-Imino-ethyl)-pyrrolidin-3-yloxy; 2-Amino-3-methyl-butyryl; 4-Acetimidoylamino-cyclohexyloxy; 1-(1-Imino-ethyl)-pyrrolidin-2-ylmethoxy; 2-(2-Hydroxycarbonimidoyl-pyridin-3-yloxy)-ethoxy; 3,4-Dicyano-phenoxy; $SC_{1-4}$ alkyl, S-aryl, O—$C_{1-4}$ alkyl, $COOR^{10}$, C(O)-pyrrolidine; C(O)CH(NH$_2$)CH$_2$OH; C(O)CH(NH$_2$)CH$_2$Ph; C(O)CH(NH$_2$)CH$_2$COOH; O-pyrrolidine; C(O)—(CH$_2$)$_{1-3}$-imidazole; SO$_2$—N(alkyl)$_2$; C(=N)—$C_3$; O-piperidine; 2-aminothiazol-5-ylmethoxy; O—CH$_2$—COOH; pyrrolidine-2-ylmethoxy; 2,4,6-triamino pyrimidin-5-ylmethoxy; NH—SO$_2$-alkyl; NHC$_1$–C$_4$ alkyl; N(C$_1$–C$_4$)$_2$ alkyl; CF$_3$; C$_{2-10}$ alkenyl and C$_{1-10}$ alkyl.

The term "alkyl", as used herein, is intended to A include branched and straight chain saturated aliphatic hydrocarbon groups having from 1 to 14 or the specified number of carbon atoms, illustrative examples of which include, but are not limited to, methyl, ethyl, n-propyl, i-propyl, n-butyl, i-butyl, sec-butyl, t-butyl, n-pentyl, and n-hexyl. "Alkenyl" is intended to include a branched or straight chain hydrocarbon group having one or more unsaturated carbon-carbon bonds which may occur in any stable point along the chain, such as ethenyl, propenyl, and the like. The term "alkelene" represents an alkyl group, as defined above, except that it has at least one center of unsaturation, i.e., a double bond. Illustrative examples are butene, propene, and pentene. The term "cycloalkyl", "cycloalkyl ring", "cycloalkyl radical" or "cyclic hydrocarbon" indicates a saturated or partially unsaturated three to fourteen carbon monocyclic or bicyclic hydrocarbon moiety which is optionally substituted with an alkyl group. Illustrative examples include cyclo propyl, cyclo hexyl, cyclo pentyl, and cyclo butyl. The term "alkoxy" as used herein represents —OC$_{1-6}$ alkyl.

The terms "Ar" and "aryl", as used herein, are intended to represent a stable substituted or unsubstituted (collectively also referred to as 'optionally substituted') six to fourteen membered mono-, bi- or tri-cyclic hydrocarbon radical comprising carbon and hydrogen atoms. Illustrative examples are phenyl (Ph), naphthyl, anthracyl groups, and piperanyl. It is also intended that the terms "carbocycle" and "carbocyclic" include "Ar", "ary" as well as "cyclo alkyl" groups, which are defined above. "Halogen" or "halo", as used herein, represents Cl, Br, F or I.

As used herein the term "bicyclic heterocyclic ring structure" is intended to represent a stable 7 to 10 membered bicyclic heterocyclic ring which is partially unsaturated or unsaturated (aromatic, i.e., heteroaryl) and which consists of carbon atoms and from 1 to 3 hetero atoms selected from S, O, and N, preferably nitrogen atoms. The nitrogen and sulfur atoms can exist in their respective oxidized states, while the nitrogen atom can also exist in its quaternized form. Illustrative examples of the bicyclic heterocyclic ring structure are 3H-imidazo[4,5-c]pyridine-2-yl, 1H-imidazo[4,5-c]pyridine-2-yl, 3H-pyrrolo[3,2-c]pyridine-2-yl, 3H-pyrrolo[3,2-c]pyrimidine-2-yl, thiazolo[5,4-c]pyridine-2-yl, oxazolo[5,4-c]pyridine-2-yl, 4H-thiopyrano[4,3-d]oxazole, 1H-indole-2-yl, 1H-benzimidazole-2-yl, 2,3-dihydro, 1H-indole-2-yl, 2,5-dihydro-thiopyrano[2,3-b]pyrrole, thieno[2,3-c]pyridine, 4,5-dihydro-1H-benzoimidazole-2-yl, 1H-pyrrolo[2,3c]pyridine, benzooxazole, 4H-thiopyrano[4,3-b]furan, 4,5-dihydrofuro[3,2-b]pyridine, 1,7-dihydro-thiopyrano-[2,3-b]pyrrole-2-yl, 1,4-dihydro-thiopyrano-[3,4-d]imidazole-2-yl, and 1,5-dihydro pyrano[2,3-d]imidazole-2-yl. It is preferred that when the total number of hetero atoms in the heterocycle exceeds 1, then the heteroatoms are not adjacent to one another. Preferred bicyclic heterocyclic ring structures comprise 9 to 10 membered bicyclic heterocyclic ring structures comprising a six membered ring and a five membered ring fused together such that the two rings have two common atoms. Illustrative examples of the preferred bicyclic heterocyclic ring structures are 1H-indole-2-yl, 1H-benzimidazole-2-yl.

The term "heteroaryl" is intended to represent a stable 5 to 10 membered aryl group ("aryl" as defined above), wherein one or more of the carbon atoms is replaced by a hetero atom selected from N, O, and S. The hetero atoms can exist in their chemically allowed oxidation states. Thus a Sulfur (S) atom can exist as a sulfide, sulfoxide, or sulfone. Preferred heteroaryl groups are six membered ring systems comprising not more than 2 hetero atoms. Illustrative examples of preferred heteroaryl groups are thienyl, N-substituted succinimide, 3-(alkyl amino)-5,5-dialkyl-2-cyclohexen-1-one, methyl pyridyl, alkyl theophylline, furyl, pyrrolyl, indolyl, pyrimidinyl, isoxazolyl, purinyl, imidazolyl, pyridyl, pyrazolyl, quinolyl, and pyrazinyl. The term "heterocycloalkyl" means a stable cyclo alkyl group containing from 5 to 14 carbon atoms wherein one or more of the carbon atoms is replaced by a hetero atom chosen from N, O and S. The hetero atoms can exist in their chemically allowed oxidation states. Thus Sulfur (S) can exist as a sulfide, sulfoxide, or sulfone. The heterocycloalkyl group can be completely saturated or partially unsaturated. Illustrative examples are piperidine, 1,4-dioxane, and morpholine.

As used herein the terms "heterocyclyl", "heterocyclic" and/or "het" are intended to represent a stable 5- to 7-membered monocyclic or 7- to 10-membered bicyclic heterocyclic ring which is saturated, partially unsaturated, or unsaturated (aromatic), which consists of carbon atoms and from one to 4 hetero atoms independently selected from a group consisting of N, O and S. The nitrogen and the sulfur hetero atoms can exist in their respective oxidized states. The heterocyclic ring may be attached to its pendent group at any heteroatom or carbon atom which results in a stable structure. The heterocyclic rings described herein may be substituted on a carbon or a nitrogen atom if the resulting compound is stable. The nitrogen in the heterocycle can exist in its quaternized form. It is preferred that when the total number of hetero atoms in the heterocycle exceeds 1, then the heteroatoms are not adjacent to one another. It is understood that the terms "heterocyclyl", "heterocyclic", and "het" include the terms. "heteroaryl", "heterocycloalkyl" and "bicyclic heterocyclic ring structure" as described above.

Preferred "heterocyclyl", "heterocyclic" and/or "het" groups are selected from 1-(2,Hydroxymethyl-pyrrolidin-1-yl)-2,3-dimethyl-butan-1-one, 3-Pyridin-2-yl-propan-1-ol, N-(2,3-Dimethoxy-benzyl)-2-hydroxy-acetamide, 1-Methyl-2-m-tolyl-1H-benzoimidazole-5-carboxamidine, 2-Methyl-3,4,6,7-tetrahydro-imidazo[4,5-c]pyridine-5-carboxamidine, 2-Amino-3-hydroxy-1-(2-methyl-3,4,6,7-tetrahydro-imidazo[4,5-c]pyridin-5-yl)-propan-1-one, 2-Amino-1-(2-methyl-3,4,6,7-tetrahydro-imidazo[4,5-c]pyridin-5-yl)-ethanone, 2-Methyl-4,5,6,7-tetrahydro-3H-imidazo[4,5-c]pyridine, N-o-Tolyl-methanesulfonamide, 2-Methyl-benzothiazole, 3-Amino-1-(2-hydroxymethyl-pyrrolidin-1-yl)-propan-1-one, 2-Hydroxy-1-(2-hydroxymethyl-pyrrolidin-1-yl)-ethanone, 2-(2-Hydroxy-ethyl)-indan-1,3-dione, 5-Fluoro-2-methyl-1H-benzoimidazole, 2-Methyl-1H-imidazo[4,5-c]pyridine, 2-Hydroxy-N-(2-morpholin-4-yl-ethyl)-acetamide, 2-Methyl-1H-imidazo[4,5-b]pyridine, 2-Amino-1-(3-methyl-piperidin-1-yl)-ethanone, 2-Methyl-1H-benzoimidazol-4-ol, 2-Pyridin-2-yl-ethanol, N-(3-Hydroxy-propyl)-2-phenyl-acetamide, N-(3-Hydroxy-propyl)-3-phenyl-propionamide, N-(3-Hydroxy-propyl)-benzamide, N-(2-Hydroxy-ethyl)-2-phenyl-acetamide, (4-Hydroxy-butyl)-carbamic acid tert-butyl ester, (2-Hydroxy-ethyl)-carbamic acid benzyl ester, (4-Hydroxy-piperidin-1-yl)-phenyl-methanone, 4-Bromo-2-methoxy-benzylamine, 3-Methoxy-5-trifluoromethyl-benzylamine, N-(3,5-Dimethoxy-benzyl)-acetamide, 2-Methyl-1H-benzoimidazole-5-carboxamidine, and 2-Hydroxy-N-naphthalen-1-yl-acetamide.

The following structural representations further illustrate the term "het":

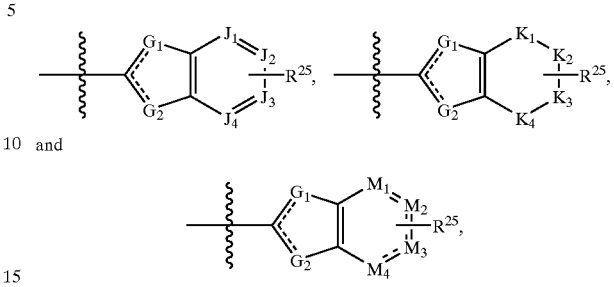

and wherein $G_1$ and $G_2$ independently at each occurance represent $S(O)_{0-2}$, NH, N—$R^{24}$, O, $CR^{10}$, or $CHR^{10}$; $J_1, J_2, J_3$, and $J_4$ independently represent $CR^{10}$ or N, wherein at least two of $J_1, J_2, J_3$ and $J_4$ represent CH; $K_1, K_2, K_3$, and $K_4$ independently represent —$NHR^{10}$, —$NHR^{24}$, —$CHR^{10}$, —CH—C(=NH)—$NH_2$, or N—C(=NH)—$NH_2$ wherein at least two of $K_1, K_2, K_3$ and $K_4$ represent $CH_2$; $M_1, M_2, M_3$ and $M_4$ independently represent —$NHR^{10}$, —$NHR^{24}$, —$CHR^{10}$, —CH—C(=NH)—$NH_2$, or N—C(=NH)—$NH_2$, wherein at least two of $M_1, M_2, M_3$ and $M_4$ represent CH or $CH_2$; and $R^{25}$ represents H, halogen, —$C_{1-6}$ alkyl, —$NO_2$, $NHR^{10}$, NH—$SO_2$—$R^{10}$, —OH, $C_{1-6}$ alkoxy, amidino, guanidino, —$COOR^{10}$, or —$CONHR^{10}$, The variables $R^{10}$ and $R^{24}$ are as defined earlier. The dashed lines indicate optional unsaturation without violating the valency rules.

The term "basic group" as used under $R^7$ and $R^8$, defined earlier, is intended to represent amidino, guanidino, —C(=NH)N($R^{10}$)$_2$, 2-imidazoline, —N-amidinomorpholine, N-amidino piperidine, 4-hydroxy-N-amidino piperidine, N-amidino pyrrolidine, tetrahydro pyrimidine, and thiazolidin-3-yl-methylideneamine. The compounds of the present invention were named using the "Autonom", a Beilstein Commander 2.1 Application, distributed by Beilstein.

The term "natural amino acid", as used herein is intended to represent the twenty naturally occurring amino acids in their 'L' form, which are some times also referred as 'common amino acids', a list of which can be found in Biochemistry, Harper & Row Publishers, Inc. (1983). The term "unnatural amino acid", as used herein, is intended to represent the 'D' form of the twenty naturally occurring amino acids described above. It is further understood that the term unnatural amino acid includes homologues of the natural amino acids, and synthetically modified form of the natural amino acids. The synthetically modified forms include amino acids having alkylene chains shortened or lengthened by up to two carbon atoms, amino acids comprising optionally substituted aryl groups, and amino acids comprised halogenated groups, preferably halogenated alkyl and aryl groups.

The term "natural amino acid side chain" is intended to represent a natural amino acid ("natural amino acid" as dfined above) wherein a keto (C=O) group replaces the carboxylic acid group in the amino acid. Thus, for example, an alanine side chain is C(=O)—CH($NH_2$)—$CH_3$; a valine side chain is C(=O)—CH($NH_2$)—CH($CH_3$)$_2$; and a cysteine side chain is C(=O)—CH($NH_2$)—$CH_2$—SH. The term "unnatural amino acid side chain" is intended to represent an unnatural amino acid ("unnatural amino acid" as defined above) wherein a keto (C=O) group replaces the carboxylic acid group forming unnatural amino acid side chains similar to ones illustrated under the definition of "natural amino acid side chain" above.

It thus follows that a "N-natural amino acid side chain" substituent and "N-unnatural amino acid side chain" substituent, which can represent Q, $Q^1$, $Q^2$, $Q^3$, $L^1$, $L^2$, $L^3$ and $L^4$, is a group wherein the nitrogen atom (N) is the annular ring atom substituted with a natural or unnatural amino acid side chain (natural or unatural amino acid side chain is a defined above). The point of attachment between the nitrogen atom and the natural or unnatural amino acid side chain is at the keto (C=O) group of the respective amino acids. Thus a N-natural amino acid, i.e., N-cysteine, is N—C(=O)—CH(NH$_2$)—CH$_2$—SH.

What is claimed is:

1. A compound of Formula I:

A—B or pharmaceutically acceptable salts thereof, wherein

A represents

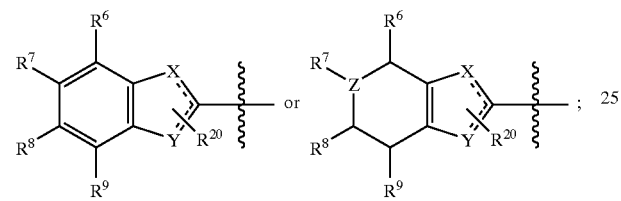

B represents

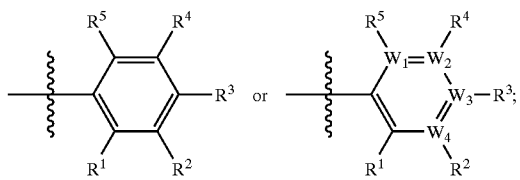

X and Y independently at each occurrence are selected from NH, N, C, or CH, such that at least one of X and Y always represents N or NH; and Z represents C or N; provided that, (i) when Z represents N, $R^7$ represents H or C(=NH)NH$_2$;

$R^1$ represents OH, halogen, COOH, COO—$C_{1-4}$ alkyl, O—(CH$_2$)$_{0-1}$—Ph, CH$_2$OR$^{10}$, $C_{1-6}$ halogenated alkyl, O—(CH$_2$)$_{1-4}$—CO—N(R$^{10}$)$_2$, SC$_{1-4}$ alkyl, NHSO$_2$C$_{1-4}$alkyl, SO$_2$—OH, O—SO$_2$—OH, O—SO$_2$—O—C$_{1-4}$ alkyl, OP(O)(OH)$_2$, or OP(O)(OH)OC$_{1-4}$ alkyl;

$R^2$, $R^3$, $R^4$ and $R^5$ independently at each occurance occurrence represent H, SH, OR$^{10}$, halogen, COOR$^{10}$, CONR$^{11}$R$^{12}$, optionally substituted aryl, optionally substituted heterocyclyl, $C_{4-14}$ cycloalkyl-$C_{1-4}$ alkyl, $C_{1-4}$ alkyl aryl, optionally substituted $C_{1-4}$ straight chain, branched or cyclo alkyl, O—(CH$_2$)$_{2-6}$—NR$^{10}$—(CH$_2$)$_{0-3}$—R$^{24}$, NR$^{10}$R$^{24}$, (CH$_2$)$_{1-4}$—NR$^{33}$R$^{34}$, (CH$_2$)$_{1-4}$—COOR$^{33}$, O—(CH$_2$)$_{1-3}$—CO-het, O—(CH$_2$)$_{1-2}$—NH—CO-aryl, O—(CH$_2$)$_{1-2}$—NR$^{10}$—CO—NR$^{10}$R$^{33}$, O—(CH$_2$)$_{0-2}$—C(O)—NR$^{33}$R$^{34}$, O—(CH$_2$)$_{1-4}$—COOR$^{10}$, O—(CH$_2$)$_{1-3}$-het-R$^{32}$, O-optionally substituted cycloalkyl, O—(CH$_2$)$_{1-4}$—NR$^{10}$—COO-t-butyl, O—(CH$_2$)$_{1-4}$-NR$^{10}$R$^{33}$, O—(CH$_2$)$_{1-4}$—NR$^{10}$—C(O)—C$_{0-3}$-alkyl-optionally substituted aryl, O-substituted cycloalkyl, O—(CH$_2$)$_{0-6}$-optionally substituted aryl, (CH$_2$)$_{1-4}$—NH—C(O)O—(CH$_2$)$_{1-4}$—PhR$^{13}$R$^{14}$, NO$_2$, O—(CH$_2$)$_{0-4}$—C(O)—NH-tetrahydro carboline, NR$^{10}$R$^{28}$, O—(CH$_2$)$_{1-3}$-optionally substituted het, CH$_2$COOCH$_3$, CH=CH—COOCH$_3$, 5-amidino benzimidazole,

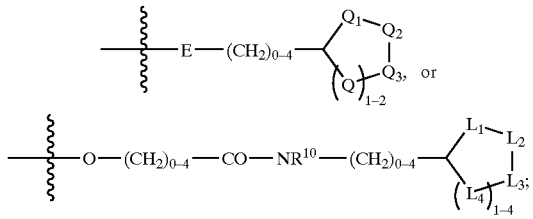

alternatively $R^2$ and $R^3$ taken together form

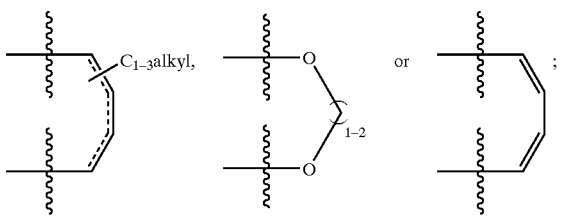

$R^6$ and $R^9$ independently at each occurrence represents H, halogen, cyano, $C_{1-4}$ alkyl, $C_{1-4}$ halogenated alkyl, NO$_2$, O-aryl or OR$^{11}$;

$R^7$ and $R^8$ independently at each occurrence represent OH, CF$_3$, H, NO$_2$, $C_{1-4}$ alkyl, OC$_{1-4}$ alkyl, O-aryl, halogen, or cyano, or a basic group selected from guanidino, C(=NH)N(R$_{10}$)$_2$, C(=NH)—NH—NH$_2$, C(=O)NH$_2$, 2-imidazoline, N-amidinomorpholine, N-amidino piperidine, 4-hydroxy-N-amidino piperidine, N-amidino pyrrolidine, tetrahydro pyrimidine, and thiazolidin-3-yl-methylideneamine; with the proviso that one, but not both, of $R^7$ and $R^8$ represents a basic group;

$R^{10}$ independently at each occurrence represents H, (CH$_2$)$_{0-2}$-aryl, $C_{1-4}$ halo alkyl, or $C_{1-14}$ straight chain, branched or cyclo alkyl, and alternatively, when one atom is substituted with two $R^{10}$ groups, the atom along with the $R^{10}$ groups can form a five to 10 membered ring structure;

$R^{11}$ and $R^{12}$ independently at each occurrence represent H or $C_{1-4}$ alkyl;

$R^{20}$ represents $R^{24}$, $C_{1-4}$-alkyl, (CH$_2$)$_{1-3}$-biphenyl, (CH$_2$)$_{1-4}$—Ph—N(SO$_2$—C$_{1-2}$-alkyl)$_2$, (CH$_2$)$_{1-4}$—NH—C(O)—R$^{24}$, (CH$_2$)$_{1-4}$—NH—SO$_2$—R$_{24}$, halogen, COOR$^{10}$, (CH$_2$)$_{1-4}$—Ph—N(SO$_2$—C$_{1-2}$ alkyl), (CH$_2$)$_{1-4}$—NR$^{10}$—C(O)—R$^{24}$, (CH$_2$)$_{1-4}$—NR$^{10}$—SO$_2$—R$^{24}$, (CH$_2$)$_{1-4}$-het, (CH$_2$)$_{1-4}$—CON(R$^{10}$)$_2$, (CH$_2$)$_{1-4}$—N(R$^{10}$)—C(O)—NR$^{10}$R$^{24}$, (CH$_2$)$_{1-4}$—N(R$^{10}$)—C(S)—NR$^{10}$R$^{24}$, or (CH$_2$)$_{1-3}$—COOH;

$R^{24}$ represents $R^{10}$, (CH$_2$)$_{1-4}$-optionally substituted aryl, (CH$_2$)$_{0-4}$R$^{10}$, CO—(CH$_2$)$_{1-2}$—N(R$_{10}$)$_2$, CO(CH$_2$)$_{1-4}$—OR$^{10}$, (CH$_2$)$_{1-4}$—COOR$^{10}$, (CH$_2$)$_{0-4}$—N(R$^{10}$)$_2$, SO$_2$R$^{10}$, COR$^{10}$, CON(R$^{10}$)$_2$, (CH$_2$)$_{0-4}$-aryl-COOR$^{10}$, (CH$_2$)$_{0-4}$-aryl-N(R$^{10}$)$_2$, or (CH$_2$)$_{1-4}$-het-aryl;

$R^{28}$ represents (CH$_2$)$_{1-2}$—Ph—O—(CH$_2$)$_{0-2}$-het-R$^{30}$, C(O)-het, CH$_2$—Ph—CH$_2$-het-(R$^{30}$)$_{1-3}$; (CH$_2$)$_{1-4}$-cyclohexyl-R$^{31}$, CH$_2$—Ph—O—Ph—(R$^{30}$)$_{1-2}$, CH$_2$—(CH$_2$OH)-het-R$^{30}$, CH$_2$—Ph—O-cycloalkyl- R³¹, CH₂-het-C(O)—CH₂-het-R³⁰, or CH₂—Ph—O—(CH₂)—O-het-R³⁰;

R³⁰ represents SO₂N(R¹⁰)₂, H, NHOH, amidino, or C(=NH)CH₃;

R³¹ represents R³⁰, amino-amidino, NH—C(=NH) CH₃ or R¹⁰;

R³² represents H, C(O)—CH₂—NH₂, or C(O)—CH(CH(CH₃)₂)—NH₂;

R³³ and R³⁴ independently at each occurrence represent R¹⁰, (CH₂)₀₋₄—Ar, optionally substituted aryl, (CH₂)₀₋₄ optionally substituted heteroaryl, (CH₂)₁₋₄—CN, (CH₂)₁₋₄—N(R¹⁰)₂, (CH₂)₁₋₄—OH, (CH₂)₁₋₄—SO₂—N(R¹⁰)₂; alternatively, R³³ and R³⁴ along with the nitrogen atom that they are attached form a 4 to 14 atom ring structure selected from tetrahydro-1H-carboline; 6,7-dialkoxyoxy-2-substituted 1,2,3,4-tetrahydro-isoquinoline,

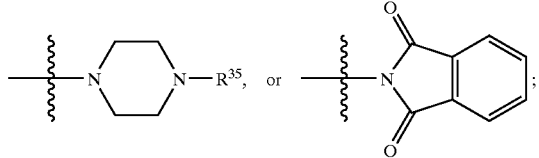

R³⁵ represents R¹⁰, SO₂—R¹⁰, COR¹⁰, or CONHR¹⁰;

E represents a bond, S(O)₀₋₂, O or NR¹⁰;

W₁, W₂, W₃ and W₄ independently represent C or N; and

Q, Q¹, Q², Q³, L¹, L², L³ and L⁴ independently at each occurrence represent N-natural or unnatural amino acid side chain, CHR¹⁰, O, NH, S(O)₀₋₂, N—C(O)—NHR¹⁰, SO₂—N(R¹⁰)₂, N—C(O)—NH—(CH₂)₁₋₄—R²⁶, NR¹⁰, N-heteroaryl, N—C(=NH)—NHR¹⁰, or N—C(=NH)C₁₋₄ alkyl;

R²⁶ represents OH, NH₂, or SH;

provided that, (i) when R¹=OH; R⁷=amidine; R², R⁶, R⁸, R⁹ and R²⁰ each represent H; and R³, R⁴, R⁵ are independently chosen from H, CH₃ and halogen, then only one of R³, R⁴, and R⁵ represents H; (ii) when R¹=OH; R⁷=amidine; R², R³, R⁴, R⁵ and R²⁰ each represent H; and R⁶, R⁸, R⁹ are independently chosen from H, CH₃, and halogen, then only one of R⁶, R⁸, and R⁹ represents H; (iii) at least two of W₁, W₂, W₃ and W₄ represent C and at least one of W₁, W₂, W₃ and W₄ represent N; and (iv) when R¹=OH; R⁷=amidine; and R², R³, R⁴, R⁵, R⁶, R⁸ and R⁹, represent H, R²⁰ cannot be CH₃.

2. A compound of claim 1 wherein

R¹ represents OH, O—Ph, COOH or P(O)(OH)₂;

R⁷ represents CONH₂, CN, C(=NH)—NH—NH₂, NH—C(=NH)—NH₂ or C(=NH)—NH₂;

R²⁰ represents H, C₁₋₂ alkyl, (CH₂)₁₋₄-optionally substituted aryl, (CH₂)₁₋₄-het; (CH₂)₁₋₄—N(R¹⁰)₂, (CH₂)₁₋₄—CON(R¹⁰)₂, (CH₂)₁₋₄—NR¹⁰—C(O)—R²⁴, (CH₂)₁₋₄—NR¹⁰—SO₂—R²⁴, or (CH₂)₁₋₃—COOH.

3. A compound of claim 2 wherein

A represents

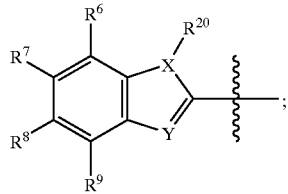

B represents

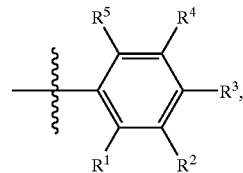

X and Y represent N; and

R⁷ represents —CONH₂ or C(=NH)—NH₂.

4. A compound of claim 3 wherein

R¹ represents OH, —COOH, or O—P(O)(OH)₂;

R² and R³ independently represent halogen, H, C₁₋₄ alkyl, Ph, toluyl, OH, O—(CH₂)₁₋₂—C(O)—NH—(CH₂)₁₋₂—CN, O—(CH₂)₁₋₃—Ph-p-OCH₃, O—CH₂—C(O)—NH—(CH₂)₁₋₂—CH—(CH₃)₂, O—CH₂—C(O)—NH—(CH₂)—Ph, O—CH₂—C(O)—NH—(CH₂)—Ph-pCH₃, O—C₁₋₃ alkyl, O—(CH₂)₀₋₂—Ph—R¹⁰, O—CH₂—C(O)—NH—(CH₂)₂—H, Ph—C₁₋₃ alkyl, Ph—N(R¹⁰)₂, O—(CH₂)₁₋₃-het, O—(CH₂)₁₋₃—Ph-halo, O—(CH₂)₁₋₃—NHSO₂Ph—R¹⁰, O—(CH₂)₁₋₃—NHCO—(CH₂)₀₋₂—Ph, O—CH₂—C(O)—NH—CH₂—COO—C(CH₃)₃, O—(CH₂)₂—NHC(O)—CH₂—NH₂, —OPh, O—(CH₂)₁₋₃—NH-het, O—(CH₂)₂—NH—C(O)-pyridyl, O—(CH₂)₂—NH—C(O)—NH-benzyl, O—(CH₂)₂-cyclohexyl, O—(CH₂)₂—NH—C(O)—(CH₂)₂—CONH₂, O—(CH₂)₂—NH—C(O)—CH₂—OCH₃, thiophene, pyridyl or O—(CH₂)₂-pyridyl;

alternatively R² and R³ taken together form

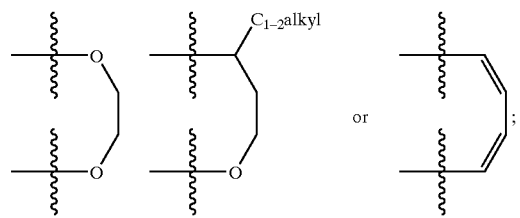

R⁴ represents halogen, H, NO₂, C₁₋₂-alkyl, CH=CH—COOCH₃, NHSO₂C₁₋₂ alkyl, NHCO-het, (CH₂)₁₋₃—COOR¹⁰, (CH₂)₁₋₃—CONH—(CH₂)₁₋₃-pyridyl, or (CH₂)₁₋₃—CONH—(CH₂)₁₋₃-dichlorophenyl;

R⁵ represents H;

R⁶ represents H;

R⁷ represents C(=NH)—NH₂ or NH(=NH)NH₂;

R⁸ represents H, halogen, OR¹⁰, CF₃, or C(=NH)—NH₂;

R⁹ represents H or halogen; and

R²⁰ represents H.

5. A compound of claim 4 wherein

R¹ represents OH, or COOH;

R² represents H, halogen, OH, phenyl, O—(CH₂)₁₋₃—Ph, imidazolyl, 5-amidino benzimidazolyl, O—(CH₂)₁₋₂—C(O)—NH—C₁₋₆ alkyl, or O—CH₂—C(O)—NH—CH₂—Ph;

R³ represents H, O—CH₂—COOH, O—CH₂—C(O)O—C₂H₅, O—CH₂—C(O)—NH—(CH₂)₁₋₄-aryl, O—(CH₂)₁₋₄—NH—C(O)-naphthyl, CONH₂, O—(CH₂)₁₋₂—C(O)N(R¹⁰)—(CH₂)₁₋₃—Ph—R¹³R¹⁴, O—CH₂—C(O)—N(R¹⁰)—CH₂-piperanyl, O—CH₂—C(O)—NH—CH₂-indoyl, (CH₂)₀₋₄-aryl, $R^4$ represents H, —CH$_3$, halogen, —OCH$_3$,—(CH$_2$)$_{1-2}$COOR$^{10}$, —COOH, —NO$_2$, —OH, aryl, $R^5$ represents H;
$R^6$ represents H;
$R^7$ represents —C(O)—NH$_2$ or —C(=NH)—NH$_2$;
$R^8$ represents H, Cl, F, OH or OCH$_3$;
$R^9$ represents H; and
$R^{13}$ and $R^{14}$ independently at each occurrence represents H, halogen, —OC$_{1-2}$ alkyl, —CF$_3$, or —C$_{1-4}$ alkyl; and
$R^{15}$ represents H, $R^{20}$ represents H or —CH$_2$—Ph.

6. A compound selected from
3-[3-Bromo-5-(6-carbamimidoyl-1H-benzoimidazol-2-yl)-4hydroxy-phenyl]-N-phenethyl-propionamide;
3-[4-(6-Carbamimidoyl-1H-benzoimidazol-2-yl)-3-hydroxy-phenyl]-N-(2,3-dichloro-benzyl)-propionamide;
2-[4(6-Carbamimidoyl-1H-benzoimidazol-2-yl)-3-hydroxy-phenoxy]-N-(2,3-dichloro-benzyl)-acetamide;
3-[3-Bromo-5-(6-carbamimidoyl-1H-benzoimidazol-2-yl)-4-hydroxy-phenyl]-N-[2-(2,4-dichloro-phenyl)-ethyl]-propionamide;
3-[3-Bromo-5-(6-carbamimidoyl-1H-benzoimidazol-2-yl)-4-hydroxy-phenyl]-N-(2-pyridin-2-yl-ethyl)-propionamide;
3-[3-Bromo-5-(6-carbamimidoyl-1H-benzoimidazol-2-yl)-4-hydroxy-phenyl]-N-(3-phenyl-propyl)-propionamide;

2-[4-(6-Carbamimidoyl-1H-benzoimidazol-2-yl)-3-hydroxy-phenoxy]-N-naphthalen-1-ylmethyl-acetamide;

2-(3'-Amino-5-chloro-2-hydroxy-biphenyl-3-yl)-3H-benzoimidazole-5-carboxamidine;

3-[3-Bromo-5-(6-carbamimidoyl-1H-benzoimidazol-2-yl)-4-hydroxy-phenyl]-propionic acid;

2-(3,5-Bis-hydroperoxy-2-hydroxy-phenyl)-3H-benzoimidazole-5-carboxamidine;

2-[4-(5-Carbamimidoyl-1H-benzoimidazol-2-yl)-3-hydroxy-phenoxy]-N-(3-chloro-benzyl)-acetamide;

N-Benzyl-3-[3-bromo-5-(6-carbamimidoyl-1H-benzoimidazol-2-yl)-4-hydroxy-phenyl]-propionamide;

2-(3,5-Dibromo-2,4-dihydroxy-phenyl)-3H-benzoimidazole-5-carboxamidine;

2-(2-Hydroxy-biphenyl-3-yl)-3H-benzoimidazole-5-carboxamidine;

2-(5-Chloro-2-hydroxy-biphenyl-3-yl)-3H-benzoimidazole-5-carboxamidine;

2-(2-Hydroxy-3-phenethyloxy-phenyl)-3H-benzoimidazole-5-carboxamidine;

N-(3-Bromo-benzyl)-2-[4-(5-carbamimidoyl-1H-benzoimidazol-2-yl)-3-hydroxy-phenoxy]-acetamide;

2-{3-[1-(3-Amino-propionyl)-pyrrolidin-2-ylmethoxy]-2-hydroxy-phenyl}-3H-benzoimidazole-5-carboxamidine;

2-(5-Chloro-2-hydroxy-3-pyridin-3-yl-phenyl)-1H-benzoimidazole-5-carboxamidine;

2-[3-(5-Carbamimidoyl-1H-benzoimidazol-2-yl)-2-hydroxy-phenyl]-3,4,6,7-tetrahydro-imidazo[4,5-c]pyridine-5-carboxamidine;

2-[3-(1-Aminoacetyl-pyrrolidin-2-ylmethoxy)-2-hydroxy-phenyl]-3H-benzoimidazole-5-carboxamidine;

2-(2-Hydroxy-3-phenoxy-phenyl)-3H-benzoimidazole-5-carboxamidine;

2-[2-Hydroxy-3-(1-methyl-1H-benzoimidazol-2-yl)-phenyl]-1H-benzoimidazole-5-carboxamidine;

2-[3-(1-Aminoacetyl-piperidin-3-ylmethoxy)-2-hydroxy-phenyl]-1H-benzoimidazole-5-carboxamidine;

2-{3-[1-(2-Amino-3-methyl-butyryl)-pyrrolidin-2-ylmethoxy]-2-hydroxy-phenyl}-1H-benzoimidazole-5-carboxamidine;

2-[2-Hydroxy-3-(1-hydroxyacetyl-pyrrolidin-2-ylmethoxy)-phenyl]-1H-benzoimidazole-5-carboxamidine;

2-(2-Hydroxy-5-iodo-3-methoxy-phenyl)-1H-benzoimidazole-5-carboxamidine;

2-{3-[1-(2-Amino-3-methyl-butyryl)-pyrrolidin-2-ylmethoxy]-2-hydroxy-phenyl}-3H-benzoimidazole-5-carboxamidine;

2-(2-Hydroxy-5-{4-[1-(1-imino-ethyl)-piperidin-4-yloxy]-benzylamino}-phenyl)-3H-benzoimidazole-5-carboxamidine; compound with methane;

2-(2-Hydroxy-5-{4-[1-(1-imino-ethyl)-piperidin-3-ylmethoxy]-benzylamino}-phenyl)-3H-benzoimidazole-5-carboxamidine;

2-(3-Bromo-2-hydroxy-5-methyl-phenyl)-3H-benzoimidazole-5-carboxamidine;

3-[2,6-Dibromo-4-(6-carbamimidoyl-1H-benzoimidazol-2-yl)-3-hydroxy-phenoxy]-propionic acid;

3-[2,6-Dibromo-4-(6-carbamimidoyl-1H-benzoimidazol-2-yl)-3-hydroxy-phenoxy]-propionic acid ethyl ester; and 2-[3-Bromo-2-hydroxy-5-(3-methoxy-but-3-enyl)-phenyl]-3H-benzoimidazole-5-carboxamidine;

or a stereoisomer or pharmaceutically acceptable salt form thereof.

7. A compound of claim 1 wherein A represents

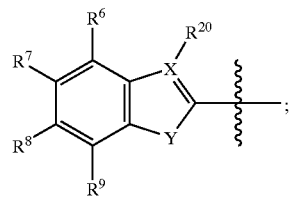

B represents

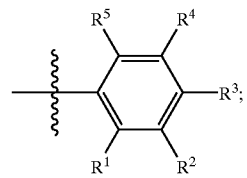

X represents C; and
Y represents NH.

8. A compound of claim 7 wherein $R^1$ represents —OH, —COOH, or P(O)(OH)$_2$;

$R^2$ represents H, halogen, $R^{10}$, -aryl, heteroaryl, —$C_{1-2}$-alkyl, COOH, —O$C_{1-2}$-alkyl or —O—(CH$_2$)$_{0-2}$-aryl;

$R^3$ represents H or —O—(CH$_2$)$_{1-3}$—COOH;

alternatively $R^2$ and $R^3$ taken together represent

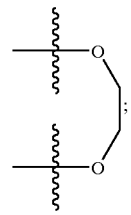

$R^4$ represents H, $C_{1-4}$ alkyl, —(CH$_2$)$_{1-4}$—COOH, —(CH$_2$)$_{1-4}$—COO$C_{1-2}$-alkyl, halogen, —(CH$_2$)$_{1-2}$—CONH$_2$, —CONH$_2$, —NO$_2$, —O—$C_{1-2}$ alkyl, or —OH;

$R^5$ represents H, $C_{1-3}$ alkyl or —COOH;

$R^6$ represents H, halogen, or —$C_{1-3}$ alkyl;

$R^7$ represents —C(O)—NH$_2$, —C(=NH)—NH—NH$_2$, or amidino;

$R^8$ represents H, or halogen; and $R^{20}$ represents H, —(CH$_2$)$_{1-4}$—Ph—N(SO$_2$—$C_{1-2}$alkyl), —(CH$_2$)$_{1-4}$—NR$^{10}$—C(O)—R$^{24}$, —(CH$_2$)$_{1-4}$—NR$^{10}$—SO$_2$—R$^{24}$, —(CH$_2$)$_{1-4}$-het, —(CH$_2$)$_{1-4}$—CON(R$^{10}$)$_2$, —(CH$_2$)$_{1-4}$—N(R$^{10}$)—C(O—NR$^{10}$R$^{24}$, —(CH$_2$)$_{1-4}$—N(R$^{10}$)—C(S)—NR$^{10}$R$^{24}$, —$C_{1-2}$-alkyl, —(CH$_2$)$_{1-4}$-optionally substituted aryl, —(CH$_2$)$_{1-4}$-het; —(CH$_2$)$_{1-3}$—N(R$^{10}$)$_2$; —(CH$_2$)$_{1-4}$—CON(R$^{10}$)$_2$, or —(CH$_2$)$_{1-3}$—COOH.

9. A compound of claim 8 wherein the compound is selected from

3-Benzyl-2-(3-chloro-2-hydroxy-phenyl)-1H-indole-5-carboxamidine;

3-[3-(3-Benzyl-5-carbamimidoyl-1H-indol-2-yl)-5-bromo-4-hydroxy-phenyl]-propionic acid;

[3-(3-Benzyl-5-carbamimidoyl-1H-indol-2-yl)-5-bromo-4-hydroxy-phenyl]-acetic acid;

6-Chloro-2-(3,5-dichloro-2-hydroxy-phenyl)-1H-indole-5-carboxamidine;

3-Bromo-5-(5-carbamimidoyl-1H-indol-2-yl)-4-hydroxy-benzamide;

2-(3,5-Dichloro-2-hydroxy-phenyl)-1H-indole-5carboxamidine;

3-(4-Amino-benzyl)-2-(3-bromo-2-hydroxy-5-methyl-phenyl)-1H-indole-5-carboxamidine;

2-(2-Hydroxy-biphenyl-3-yl)-1H-indole-5-carboxamidine;

2-(3-Bromo-2-hydroxy-5-nitro-phenyl)-1H-indole-5-carboxamidine;

2-(5-Hydroxy-2,3-dihydro-benzo[1,4]dioxin-6-yl)-1H-indole-5-carboxamidine;

3-Benzyl-2-(2-hydroxy-phenyl)-1H-indole-5-carboxamidine;

3-Benzyl-2-(3,5-difluoro-2-hydroxy-phenyl)-1H-indole-5-carboxamidine;

3-Benzyl-2-(3,5-dibromo-2-hydroxy-phenyl)-1H-indole-5-carboxamidine;

[3-Bromo-5-(5-carbamimidoyl-1H-indol-2-yl)-4-hydroxy-phenyl]-acetic acid;

3-Benzyl-2-(5-chloro-2-hydroxy-phenyl)-1H-indole-5-carboxamidine;

2-[3-Bromo-5-(5-carbamimidoyl-1H-indol-2-yl)-4-hydroxy-phenyl]-acetamide;

2-(3,5-Difluoro-2-hydroxy-phenyl)-1H-indole-5-carboxamidine;

2-(3,5-Dibromo-2-hydroxy-phenyl)-1H-indole-5-carboxamidine;

2-(2-Hydroxy-5-methyl-biphenyl-3-yl)-1H-indole-5-carboxamidine;

2-(2-Hydroxy-5,4'-dimethyl-biphenyl-3-yl)-1H-indole-5-carboxamidine;

2-(3-Bromo-2-hydroxy-5-methyl-phenyl)-1H-indole-5-carboxamidine;

3-Benzyl-2-(3-bromo-2-hydroxy-5-methyl-phenyl)-1H-indole-5-carboxamidine;

3-Benzyl-2-(3-chloro-2-hydroxy-5-methyl-phenyl)-1H-indole-5-carboxamidine;

3-Benzyl-2-(2-hydroxy-3,5-dimethyl-phenyl)-1H-indole-5-carboxamidine;

2-(3,5-Dibromo-2-hydroxy-phenyl)-3-methyl-1H-indole-5-carboxamidine;

2-(2-Hydroxy-5-methyl-3-thiophen-2-yl-phenyl)-1H-indole-5-carboxamidine;

2-[2-(3-Bromo-2-hydroxy-5-methyl-phenyl)-5-carbamimidoyl-1H-indol-3-yl]-acetamide;

[3-(3-Benzyl-5-carbamimidoyl-1H-indol-2-yl)-5-bromo-4-hydroxy-phenyl]-acetic acid methyl ester;

3-[3-(3-Benzyl-5-carbamimidoyl-1H-indol-2-yl)-5-bromo-4-hydroxy-phenyl]-propionic acid methyl ester;

3-(3-Amino-benzyl)-2-(3-bromo-2-hydroxy-5-methyl-phenyl)-1H-indole-5-carboxamidine;

2-(3-Bromo-2-hydroxy-5-methyl-phenyl)-3-(3-nitro-benzyl)-1H-indole-5-carboxamidine;

3-(3-Amino-benzyl)-2-(2-hydroxy-5-methyl-phenyl)-1H-indole-5-carboxamidine;

3-Benzyl-2-(3-chloro-2-hydroxy-5-methyl-phenyl)-1H-indole-5-carboxamidine;

6-Chloro-2-{5-[2-(1,1-dioxo-1-thiomorpholin-4-yl)-2-oxo-ethyl]-2-hydroxy-biphenyl-3-yl}-1H-indole-5-carboxamidine;

2-[5-(5-Carbamimidoyl-6-chloro-1H-indol-2-yl)-6-hydroxy-biphenyl-3-yl]-N-(2-piperidin-1-yl-ethyl)-acetamide;

6-Chloro-2-{2-hydroxy-5-[2-(2-methoxymethyl-pyrrolidin-1-yl)-2-oxo-ethyl]-biphenyl-3-yl}-1H-indole-5-carboxamidine;

6-Chloro-2-{2-hydroxy-5-[2-oxo-3-(tetrahydro-furan-2-yl)-propyl]-biphenyl-3-yl}-1H-indole-5-carboxamidine;

2-[5-(5-Carbamimidoyl-6-chloro-1H-indol-2-yl)-6-hydroxy-biphenyl-3-yl]-N-(tetrahydro-furan-2-ylmethyl)-acetamide;

2-[5-(5-Carbamimidoyl-6-chloro-1H-indol-2-yl)-6-hydroxy-biphenyl-3-yl]-N-(3-methoxy-propyl)-acetamide;

Morpholine-4-carboxylic acid {2-[5-(5-carbamimidoyl-6-chloro-1H-indol-2-yl)-6-hydroxy-biphenyl-3-yloxy]-ethyl}-amide;

Phosphoric acid mono-{2-[3-(3-benzyl-5-carbamidoyl-1H-indol-2-yl)-5-bromo-4-hydroxy-phenyl]-ethyl} ester;

2-[3-(3-Benzyl-5-carbamimidoyl-1H-indol-2-yl)-5-bromo-4-hydroxy-phenyl]-N-{4-[1-(1-imino-ethyl)-piperidin-4-yloxy]-phenyl}-acetamide;

4-[3-(3-Benzyl-5-carbamimidoyl-1H-indol-2-yl)-5-bromo-4-hydroxy-phenyl]-butyric acid;

2-[3-(3-Benzyl-5-carbamimidoyl-1H-indol-2-yl)-5-bromo4-hydroxy-phenyl]-acetamide;

2-[3-(3-Benzyl-5-carbamimidoyl-1H-indol-2-yl)-5-bromo-4-hydroxy-phenyl]-N,N-dimethyl-acetamide;

[3-(3-Benzyl-5-carbamimidoyl-1H-indol-2-yl)-5-bromo-4-hydroxy-phenyl]-acetic acid;

3-[3-(3-Benzyl-5-carbamimidoyl-1H-indol-2-yl)-5-bromo-4-hydroxy-phenyl]-pentanedioic acid bis-[(2-morpholin-4-yl-ethyl)-amide];

3-[3-(3-Benzyl-5-carbamimidoyl-1H-indol-2-yl)-5-bromo-4-hydroxy-phenyl]-propionamide; and 2-(3-Bromo-2-hydroxy-5-methyl-phenyl)-3-(4-nitro-benzyl)-1H-indole-5-carboxamidine;

or a stereoisomer or pharmaceutically acceptable salt form thereof.

10. A pharmaceutical composition comprising a pharmaceutically acceptable carrier and a therapeutically effective amount of a compound according to claim 1 or a pharmaceutically acceptable salt thereof.

11. A pharmaceutical composition comprising a pharmaceutically acceptable carrier and a therapeutically effective amount of a compound according to claim 7 or a pharmaceutically acceptable salt thereof.

12. A method for treating or preventing a arterial thromboembolism, comprising administering to a patient in need thereof a therapeutically effective amount of a compound having the formula:

A—B or pharmaceutically acceptable salts thereof, wherein
A represents

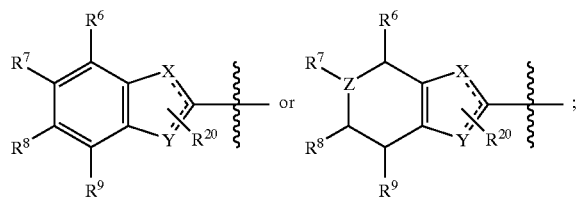

B represents

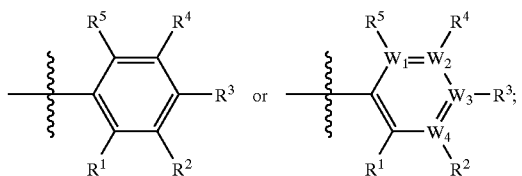

X and Y independently at each occurrence are selected from NH, N, C, or CH, such that at least one of X and Y always represents N or NH; and Z represents C or N; provided that, (i) when Z represents N, $R^7$ represents H or C(=NH)NH$_2$;

$R^1$ represents OH, halogen, COOH, COO—O$_{1-4}$ alkyl, O—(CH$_2$)$_{0-1}$—Ph, N(R$^{10}$)$_2$, CH$_2$OR$^{10}$, C$_{1-6}$-halogenated alkyl, O—(CH$_2$)$_{1-4}$—CO—N(R$^{10}$)$_2$, SC$_{1-4}$ alkyl, NHSO$_2$C$_{1-4}$alkyl, SO$_2$—OH, O—SO$_2$—OH, O—SO$_2$—O—C$_{1-4}$ alkyl, OP(O)(OH)$_2$, or OP(O)(OH) OC$_{1-4}$ alkyl;

$R^2$, $R^3$, $R^4$, and $R^5$ independently at each occurrence represent H, SH, OR$^{10}$, halogen, COOR$^{10}$, CONR$^{11}$R$^{12}$, optionally substituted aryl, optionally substituted heterocyclyl, C$_{4-14}$ cycloalkyl-C$_{1-4}$ alkyl, C$_{1-4}$ alkyl aryl, optionally substituted C$_{1-14}$ straight chain, branched or cyclo alkyl, O—(CH$_2$)$_{2-6}$—NR$^{10}$—(CH$_2$)$_{0-3}$—R$^{24}$, NR$^{10}$R$^{24}$, (CH$_2$)$_{1-4}$—NR$^{33}$R$^{34}$, (CH$_2$)$_{1-4}$—COOR$^{33}$, O—(CH$_2$)$_{1-3}$—N—CO-het, O—(CH$_2$)$_{1-2}$—NH—CO-aryl, O—(CH$_2$)$_{1-2}$—NR$^{10}$—CO—NR$^{10}$R$^{33}$, O—(CH$_2$)$_{0-2}$—C(O)—NR$^{33}$R$^{34}$, O—(CH$_2$)$_{1-4}$—COOR$^{10}$, O—(CH$_2$)$_{1-3}$-het—R$^{32}$, O-optionally substituted cycloalkyl, O—(CH$_2$)$_{1-4}$—NR$^{10}$—COO-t-butyl, O—(CH$_2$)$_{1-4}$—NR$^{10}$R$^{33}$, O—(CH$_2$)$_{1-4}$—NR$^{10}$—C(O)—C$_{0-3}$-alkyl-optionally substituted aryl, O-substituted cycloalkyl, O—(CH$_2$)$_{0-6}$-optionally substituted aryl, (CH$_2$)$_{1-4}$—NH—C(O)O—(CH$_2$)$_{1-4}$—PhR$^{13}$R$^{14}$, NO$_2$, O—(CH$_2$)$_{0-4}$—C (O)—NH-tetrahydro carboline, NR$^{10}$R$^{28}$, O—(CH$_2$)$_{1-3}$-optionally substituted het, CH$_2$COOCH$_3$, CH=CH—COOCH$_3$, 5-amidino benzimidazole,

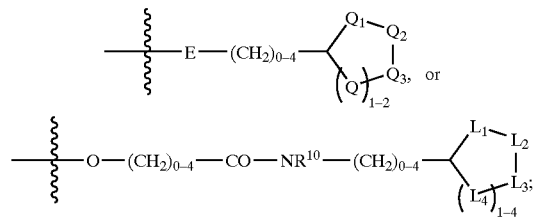

alternatively $R^2$ and $R^3$ taken together form

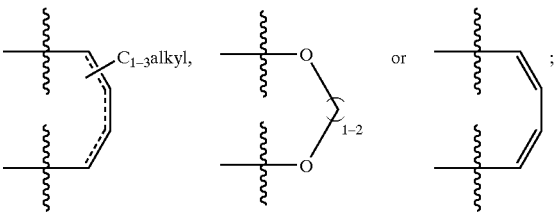

$R^6$ and $R^9$ independently at each occurrence represents H, halogen, cyano, C$_{1-4}$ alkyl, C$_{1-4}$ halogenated alkyl, NO$_2$, O-aryl or OR$^{11}$;

$R^7$ and $R^8$ independently at each occurrence represent OH, CF$_3$, H, NO$_2$, C$_{1-4}$ alkyl, OC$_{1-4}$ alkyl, O-aryl, halogen, or cyano, or a basic group selected from guanidino, C(=NH)N(R$^{10}$)$_2$, C(=NH)—NH—NH$_2$, C(=O)NH$_2$, 2-imidazoline, N-amidinomorpholine, N-amidino piperidine, 4-hydroxy-N-amidino piperidine, N-amidino pyrrolidine, tetrahydro pyrimidine, and thiazolidin-3-yl-methylideneamine; with the proviso that one, but not both, of $R^7$ and $R^8$ represents a basic group;

$R^{10}$ independently at each occurrence represents H, (CH$_2$)$_{0-2}$-aryl, C$_{1-4}$ halo alkyl, or C$_{1-14}$ straight chain, branched or cyclo alkyl, and alternatively, when one atom is substituted with two R$^{10}$ groups, the atom alone with the R$^{10}$ groups can form a five to 10 membered rind structure;

$R^{11}$ and $R^{12}$ independently at each occurrence represent H or C$_{1-4}$ alkyl;

$R^{20}$ represents R$^{24}$, C$_{1-4}$-alkyl, (CH$_2$)$_{1-3}$-biphenyl, (CH$_2$)$_{1-4}$—Ph—N(SO$_2$—C$_{1-2}$-alkyl)$_2$, (CH$_2$)$_{1-4}$—NH—C(O)—R$^{24}$, (CH$_2$)$_{1-4}$—NH—SO$_2$—R$^{24}$, halogen, COOR$^{10}$, (CH$_2$)$_{1-4}$—Ph—N(SO$_2$—C$_{1-2}$ alkyl), (CH$_2$)$_{1-4}$—NR$^{10}$—C(O)—R$^{24}$, (CH$_2$)$_{1-4}$—NR$^{10}$—SO$_2$—R$^{24}$, (CH$_2$)$_{1-4}$-het, (CH$_2$)$_{1-4}$—CON (R$^{10}$)$_2$, (CH$_2$)$_{1-4}$—N(R$^{10}$)—C(O)—NR$^{10}$R$^{24}$, (CH$_2$)$_{1-4}$—N(R$^{10}$)—C(S)—NR$^{10}$R$^{24}$, or (CH$_2$)$_{1-3}$—COOH;

$R^{24}$ represents R$^{10}$, (CH$_2$)$_{1-4}$-optionally substituted aryl, (CH$_2$)$_{0-4}$OR$^{10}$, CO—(CH$_2$)$_{1-2}$—N(R$^{10}$)$_2$, CO(CH$_2$)$_{1-4}$—OR$^{10}$, (CH$_2$)$_{1-4}$—COOR$^{10}$, (CH$_2$)$_{0-4}$—N(R$^{10}$)$_2$, SO$_2$R$^{10}$, COR$^{10}$, CON(R$^{10}$)$_2$, (CH$_2$)$_{0-4}$-aryl-COOR$^{10}$, (CH$_2$)$_{0-4}$-aryl-N(R$^{10}$)$^2$, or (CH$_2$)$_{1-4}$-het-aryl;

$R^{28}$ represents (CH$_2$)$_{1-2}$—Ph—O—CH$_2$)$_{0-2}$-het—R$^{30}$, C(O)-het, CH$_2$—Ph—CH$_2$-het-(R$^{30}$)$_{1-3}$; (CH$_2$)$_{1-4}$-cyclohexyl-R$^{31}$, CH$_2$—Ph—O—Ph—(R$^{30}$)$_{1-2}$, CH$_2$—(CH$_2$OH)-het—R$^{30}$, CH$_2$—Ph—O-cycloalkyl-R$^{31}$, CH$_2$-het-C(O)—CH$_2$-het-R$^{30}$, or CH$_2$—Ph—O—(CH$_2$)—O-het-R$^{30}$;

$R^{30}$ represents SO$_2$N(R$^{10}$)$_2$, H, NHOH, amidino, or C(=NH)CH$_3$;

$R^{31}$ represents R$^{30}$, amino-amidino, NH—C(=NH)CH$_3$ or R$^{10}$;

$R^{32}$ represents H, C(O)—CH$_2$—NH$_2$, or C(O)—CH(CH (CH$_3$)$_2$)—NH$_2$;

$R^{33}$ and $R^{34}$ independently at each occurrence represent R$^{10}$, (CH$_2$)$_{0-4}$—Ar, optionally substituted aryl, (CH$_2$)$_{0-4}$ optionally substituted heteroaryl, (CH$_2$)$_{1-4}$—CN, (CH$_2$)$_{1-4}$—N(R$^{10}$)$_2$, (CH$_2$)$_{1-4}$—OH, (CH$_2$)$_{1-4}$—SO—N(R$^{10}$)$_2$; alternatively, $R^{33}$ and $R^{34}$ along with the nitrogen atom that they are attached form a 4 to 14 atom ring structure selected from tetrahydro-1H-carboline; 6,7-dialkoxyoxy-2-substituted 1,2,3,4-tetrahydro-isoquinoline,

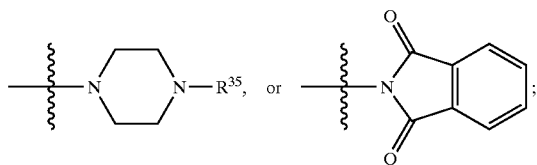

$R^{35}$ represents $R^{10}$, $SO_2$—$R^{10}$, $COR^{10}$, or $CONHR^{10}$;

E represents a bond, $S(O)_{0-2}$, O or $NR^{10}$;

$W_1$, $W_2$, $W_3$ and $W_4$ independently represent C or N; and

Q, $Q^1$, $Q^2$, $Q^3$, $L^1$, $L^2$, $L^3$ and $L^4$ independently at each occurrence represent N-natural or unnatural amino acid side chain, $CHR^{10}$, O, NH, $S(O)_{0-2}$, N—C(O)—$NHR^{10}$, $SO_2$—$N(R^{10})_2$, N—C(O)—NH—$(CH_2)_{1-4}$—$R^{26}$, $NR^{10}$, N-heteroarl, N—C(=NH)—$NHR^{10}$, or N—C(=NH)$C_{1-4}$ alkyl;

$R^{26}$ represents OH, $NH_2$, or SH;

provided that, (i) when $R^1$=OH; $R^7$=amidine; $R^2$, $R^6$, $R^8$, $R^9$, and $R^{20}$ each represent H; and $R^3$, $R^4$, $R^5$ are independently chosen from H, $CH_3$, and halogen, then only one of $R^3$, $R^4$, and $R^5$ represents H; (ii) when $R^1$=OH; $R^7$=amidine; $R^2$, $R^3$, $R^4$, $R^5$, and $R^{20}$ each represent H; and $R^6$, $R^8$, $R^9$ are independently chosen from H, $CH_3$, and halogen, then only one of $R^6$, $R^8$, and $R^9$ represents H; (iii) at least two of $W_1$, $W_2$, $W_3$ and $W_4$ represent C and at least one of $W_1$, $W_2$, $W_3$ and $W_4$ represent N; and (iv) when $R^1$=OH; $R^7$=amidine; and $R^2$, $R^3$, $R^4$, $R^5$, $R^6$, $R^8$, and $R^9$, represent H, $R^{20}$ cannot be $CH_3$, or a pharmaceutically acceptable salt thereof.

13. The method of claim 12 wherein A represents

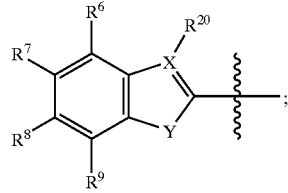

B represents

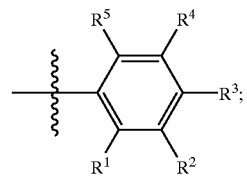

X represents C; and

Y represents NH.

* * * * *